US011141536B2

(12) United States Patent
Moser et al.

(10) Patent No.: US 11,141,536 B2
(45) Date of Patent: Oct. 12, 2021

(54) INJECTION DEVICE WITH DOSING CONTROL MEANS

(71) Applicant: Ypsomed AG, Burgdorf (CH)

(72) Inventors: Ulrich Moser, Heimiswil (CH); Jürg Hirschel, Bern (CH); Markus Tschirren, Burgdorf (CH); Philipp Wälchli, Oschwand (CH); Peter Stettler, Ersigen (CH); Patrick Sackermann, Bern (CH); Christian Schrul, Lyssach (CH); Martin Berger, Gurmels (CH); Nicolas Binggeli, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 295 days.

(21) Appl. No.: 16/182,179

(22) Filed: Nov. 6, 2018

(65) Prior Publication Data
US 2019/0134315 A1 May 9, 2019

Related U.S. Application Data

(63) Continuation of application No. 14/664,536, filed on Mar. 20, 2015, now Pat. No. 10,149,945, which is a
(Continued)

(30) Foreign Application Priority Data
Oct. 8, 2012 (CH) .................... 01875/12

(51) Int. Cl.
A61M 5/315 (2006.01)
A61M 5/28 (2006.01)
(Continued)

(52) U.S. Cl.
CPC .......... A61M 5/31536 (2013.01); A61M 5/28 (2013.01); A61M 5/3146 (2013.01);
(Continued)

(58) Field of Classification Search
CPC .............. A61M 5/3243; A61M 5/3246; A61M 5/3257; A61M 5/3271; A61M 5/3272;
(Continued)

(56) References Cited

U.S. PATENT DOCUMENTS

2004/0193110 A1* 9/2004 Giambattista ....... A61M 5/3202
604/110
2006/0129122 A1 6/2006 Wyrick
(Continued)

FOREIGN PATENT DOCUMENTS

EP 0927058 B1 7/1999
EP 1185322 B1 12/2005
(Continued)

OTHER PUBLICATIONS

"International Preliminary Report on Patentability", dated Apr. 8, 2015, for International Patent Application PCT/EP2013/060673, 12 pages.

Primary Examiner — Emily L Schmidt
Assistant Examiner — Leah J Swanson
(74) Attorney, Agent, or Firm — Dorsey & Whitney LLP

(57) ABSTRACT

An injection device provides a casing which accommodates or forms a reservoir for a liquid drug; a plunger rod which can move relative to the casing in an axially forward direction to deliver the drug; a dosing means which can move in the forward direction relative to the casing to prime the reservoir and which can rotate relative to the casing for selecting a dose to be injected, wherein rotation of the dosing means relative to the casing is prevented until a priming operation for priming the reservoir is completed; d) wherein the dosing means comprises a dosing control means which is configured to enable rotation of the dosing means at the end of the priming stroke for selecting the dose and to prevent a rotation of the dosing means back into the position
(Continued)

which the dosing means had at the end of the priming stroke relative to the casing.

27 Claims, 24 Drawing Sheets

Related U.S. Application Data continuation of application No. PCT/EP2013/060673, filed on May 13, 2013.

(51) Int. Cl.
*A61M 5/31* (2006.01)
*A61M 5/32* (2006.01)
*A61M 5/50* (2006.01)

(52) U.S. Cl.
CPC ........ *A61M 5/3155* (2013.01); *A61M 5/3202* (2013.01); *A61M 5/3204* (2013.01); *A61M 5/326* (2013.01); *A61M 5/3243* (2013.01); *A61M 5/502* (2013.01); *A61M 2005/3142* (2013.01); *A61M 2005/3143* (2013.01); *A61M 2005/3247* (2013.01); *Y10T 29/49826* (2015.01)

(58) Field of Classification Search
CPC .. A61M 2005/3247; A61M 2005/3252; A61M 2005/3258; A61M 2005/3267; A61M 2005/3268; A61M 5/31525; A61M 5/31528; A61M 5/3153; A61M 5/31533; A61M 5/31535; A61M 5/31536; A61M 5/31538; A61M 5/31541; A61M 5/31545; A61M 5/31548; A61M 5/3155; A61M 5/31551; A61M 5/31553; A61M 5/31555; A61M 5/31556; A61M 5/31558; A61M 5/3156; A61M 5/31561; A61M 5/31563; A61M 5/3146; A61M 2005/3154; A61M 5/3205; A61M 5/321; A61M 5/3245; A61M 5/326; A61M 5/3269; A61M 5/3275

See application file for complete search history.

(56) References Cited

U.S. PATENT DOCUMENTS

| | | |
|---|---|---|
| 2008/0077094 A1 | 3/2008 | Burren et al. |
| 2008/0132838 A1 | 6/2008 | Wyrick |
| 2008/0183138 A1 | 7/2008 | Moser et al. |
| 2009/0024093 A1* | 1/2009 | Carrel .................. A61M 5/326 |
| | | 604/198 |
| 2010/0010454 A1 | 1/2010 | Marshall et al. |
| 2013/0211338 A1* | 8/2013 | Roberts ............... A61M 5/3287 |
| | | 604/198 |

FOREIGN PATENT DOCUMENTS

| | | |
|---|---|---|
| WO | 2007086152 A1 | 8/2007 |
| WO | 2012118687 A1 | 9/2012 |

* cited by examiner

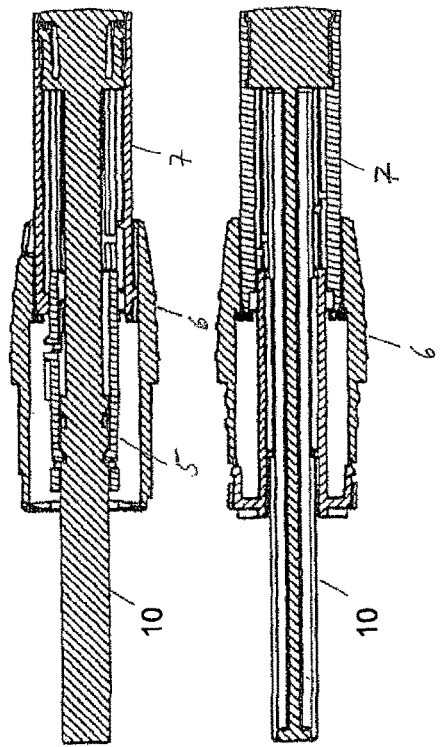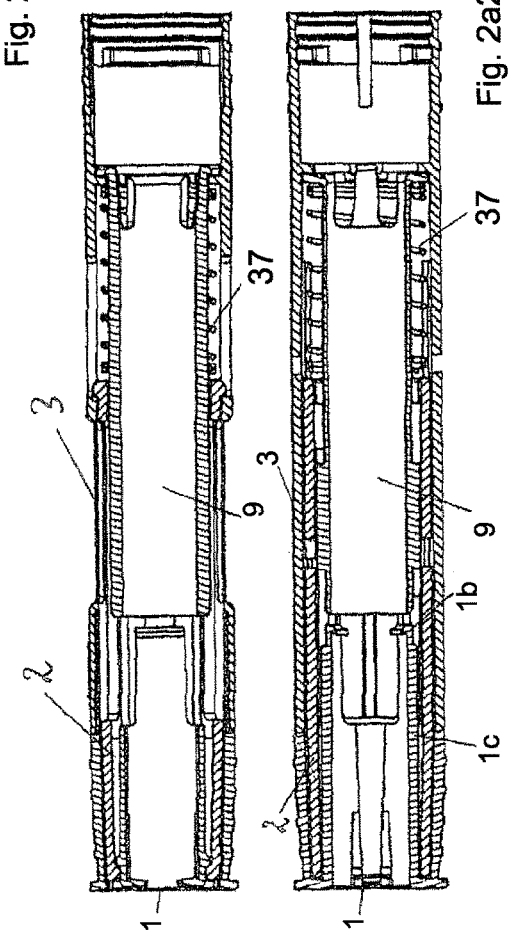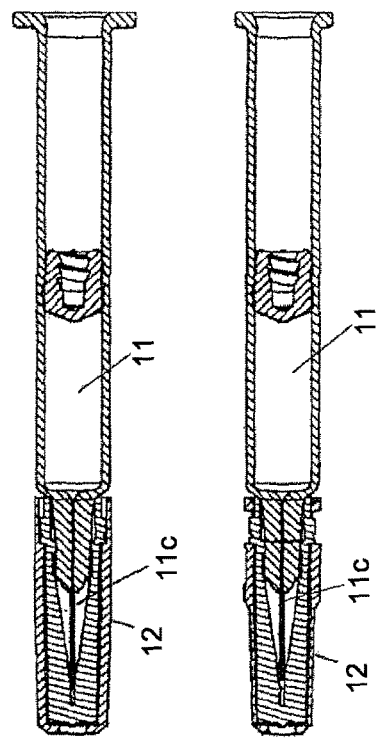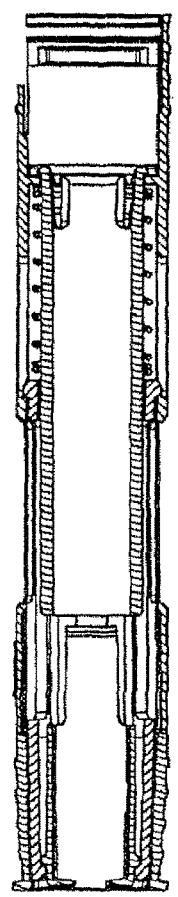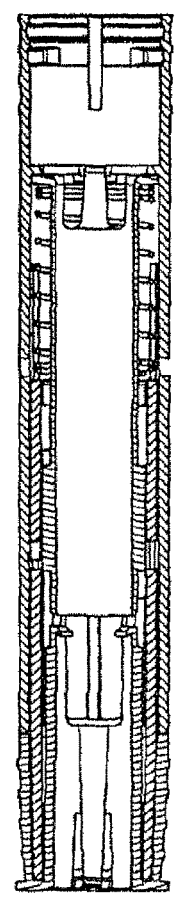
Fig. 2a1  Fig. 2a2  Fig. 2b1  Fig. 2b2

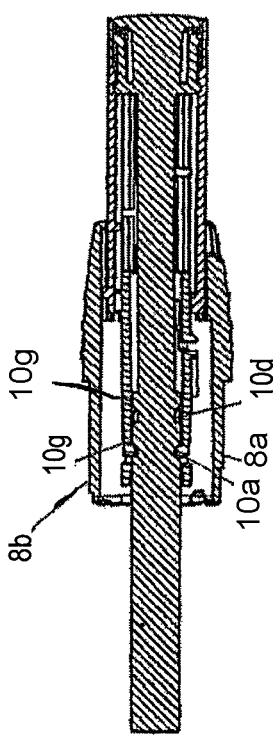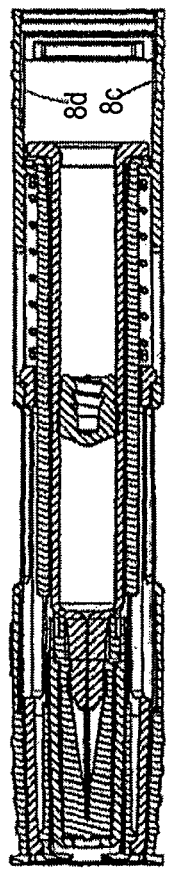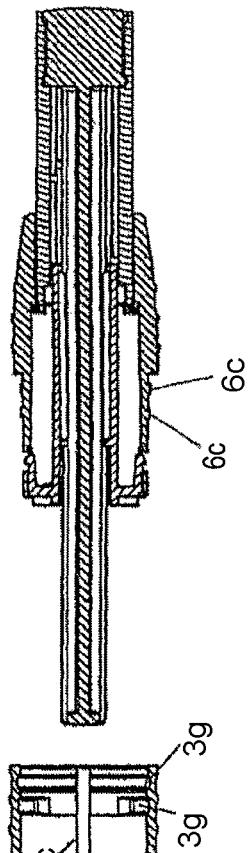
Fig. 2c1
Fig. 2c2

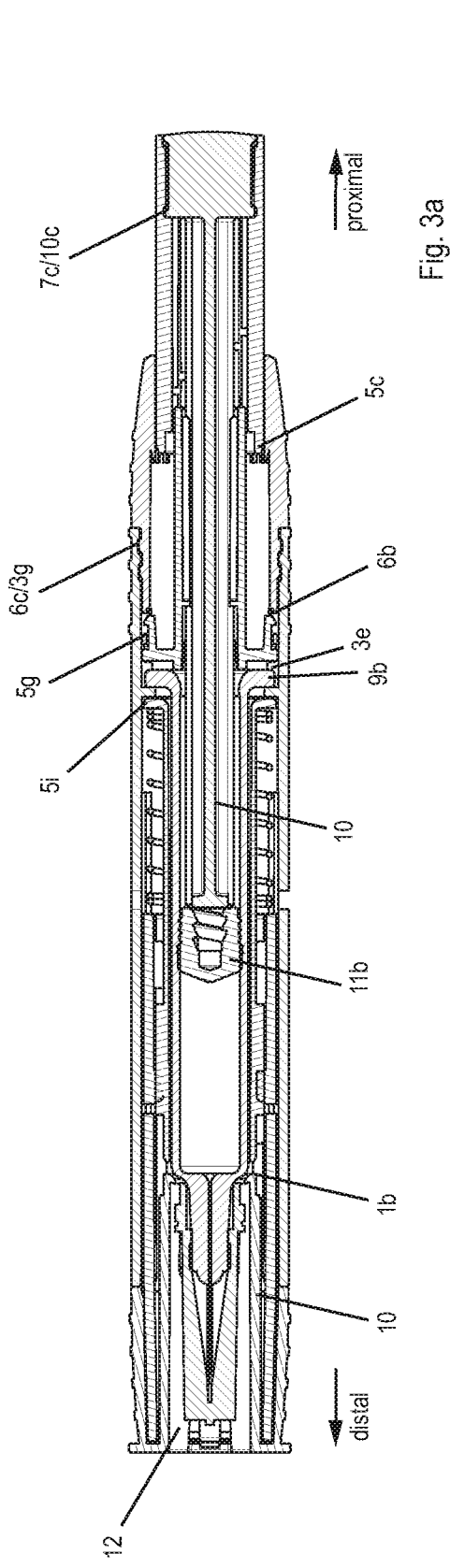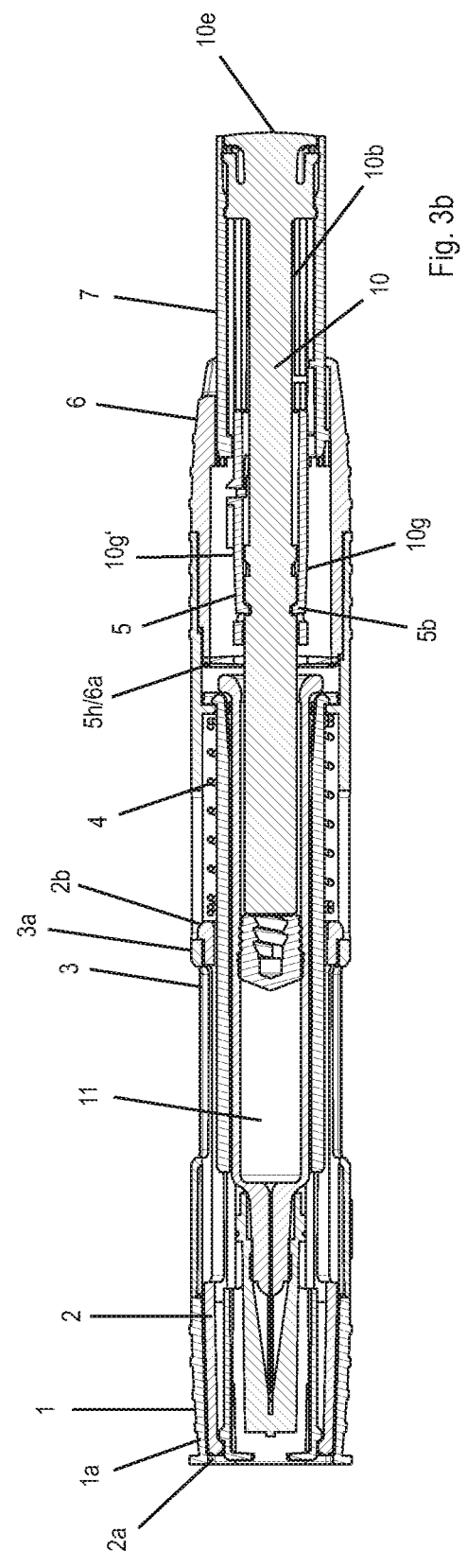

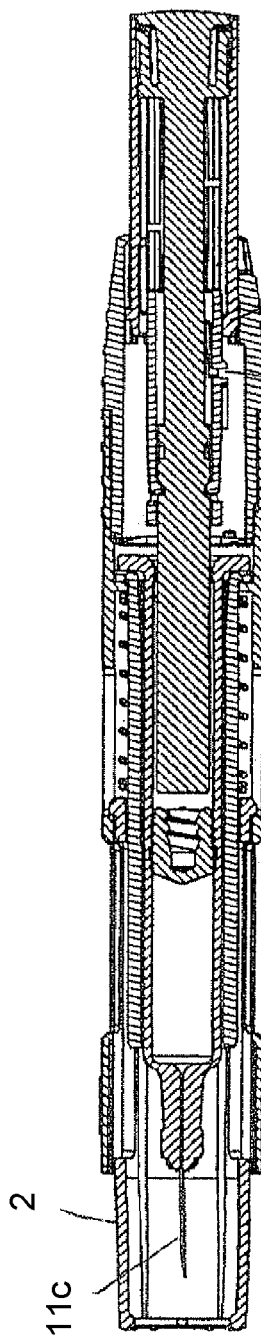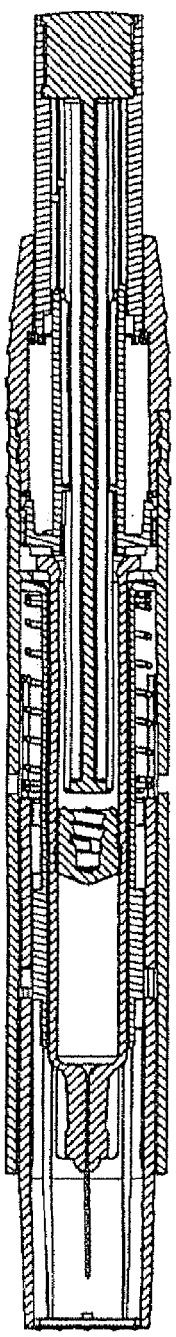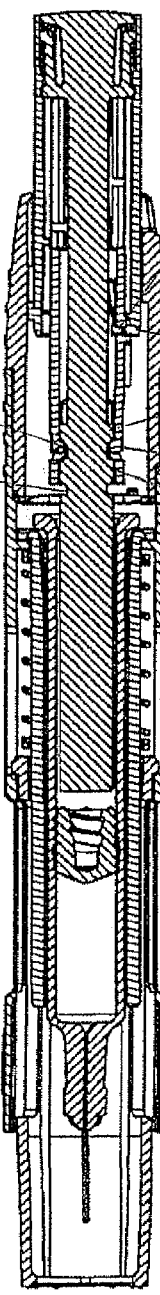

Fig. 5c1 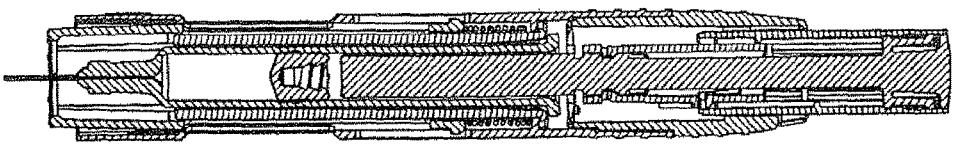
Fig. 5c1' 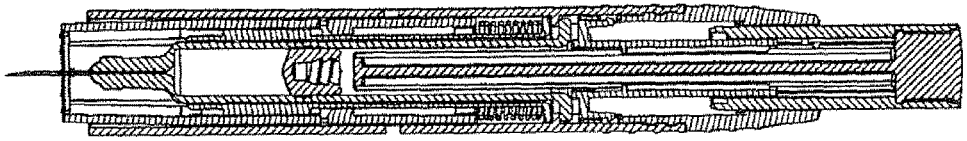
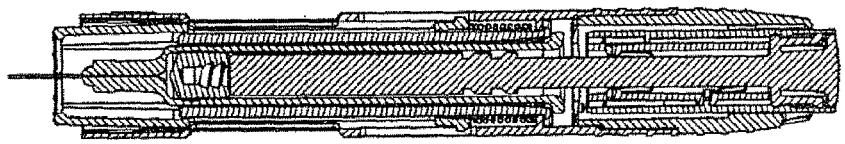 Fig. 5c2
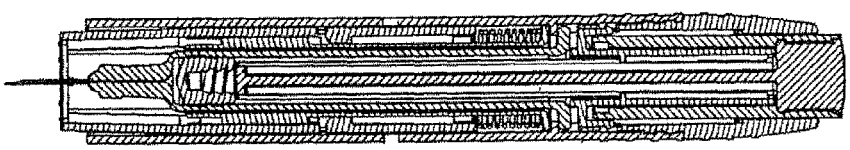 Fig. 5c2'
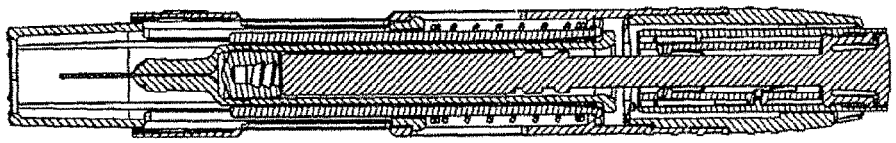 Fig. 5c3
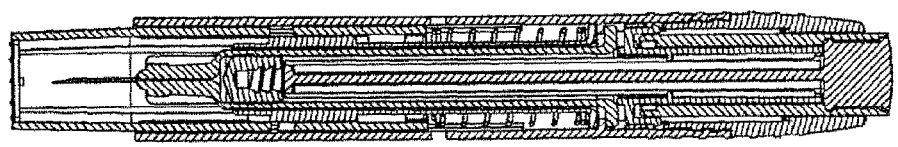 Fig. 5c3'
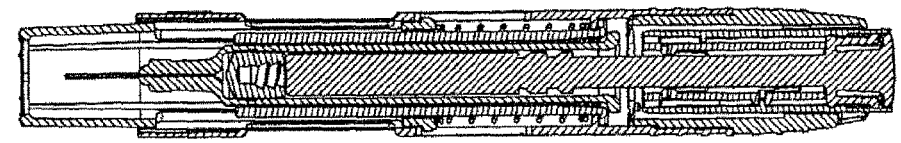 Fig. 5c4
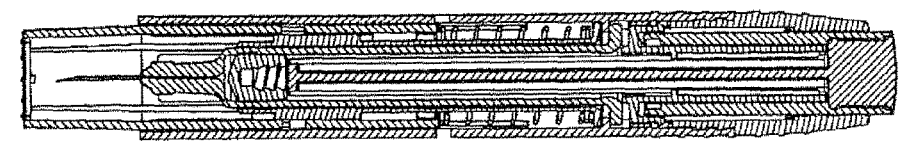 Fig. 5c4'

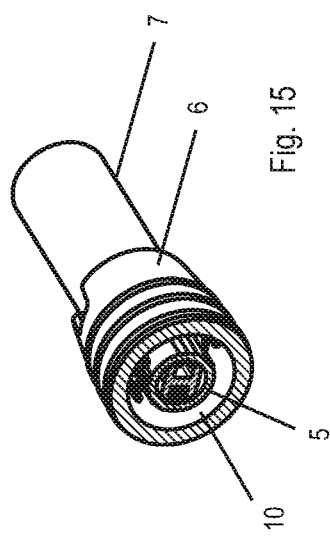
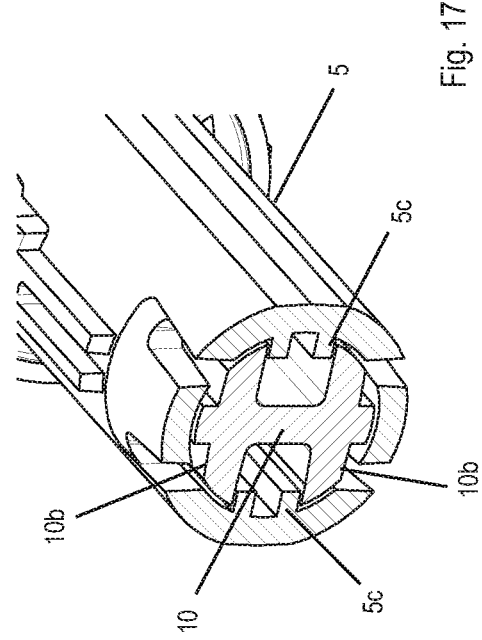
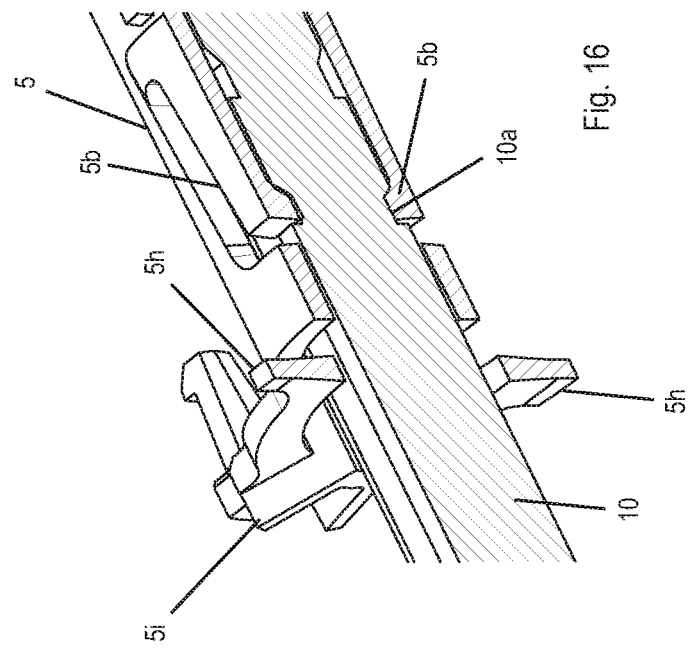

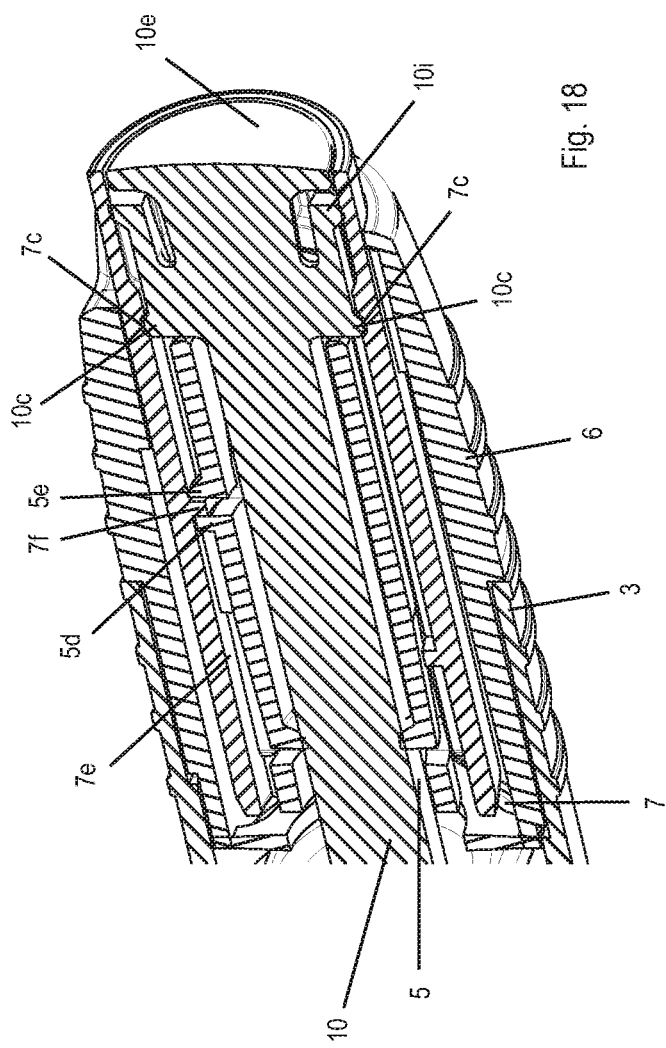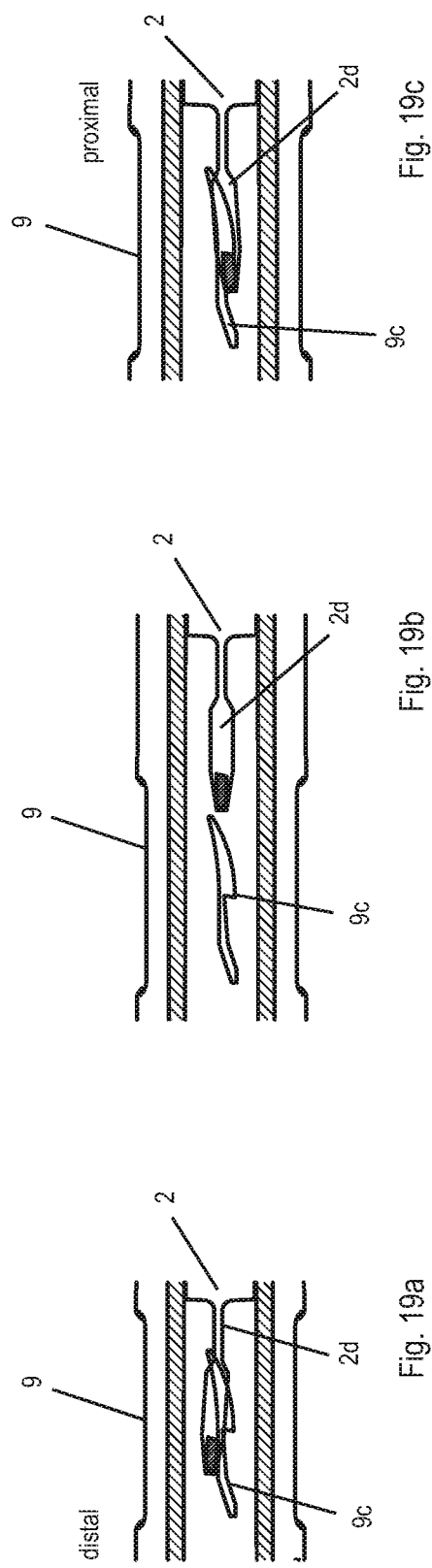

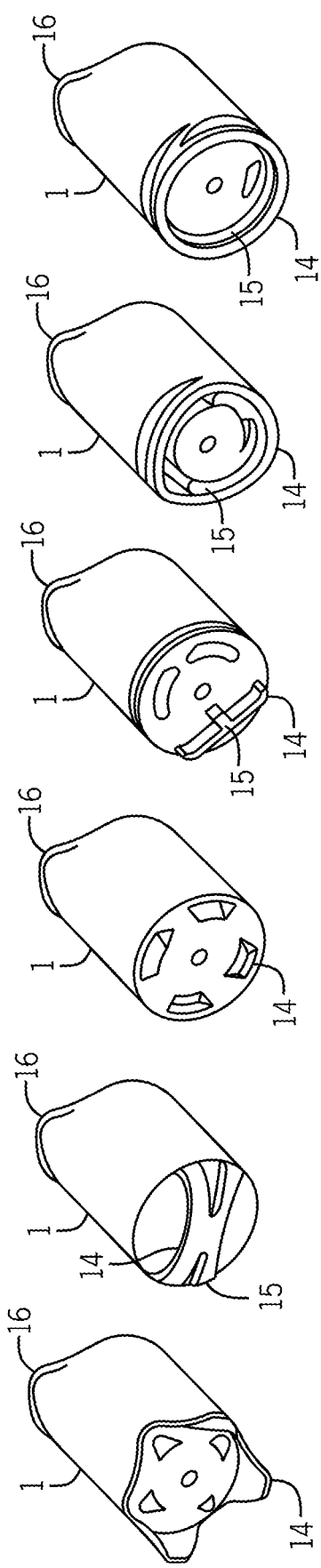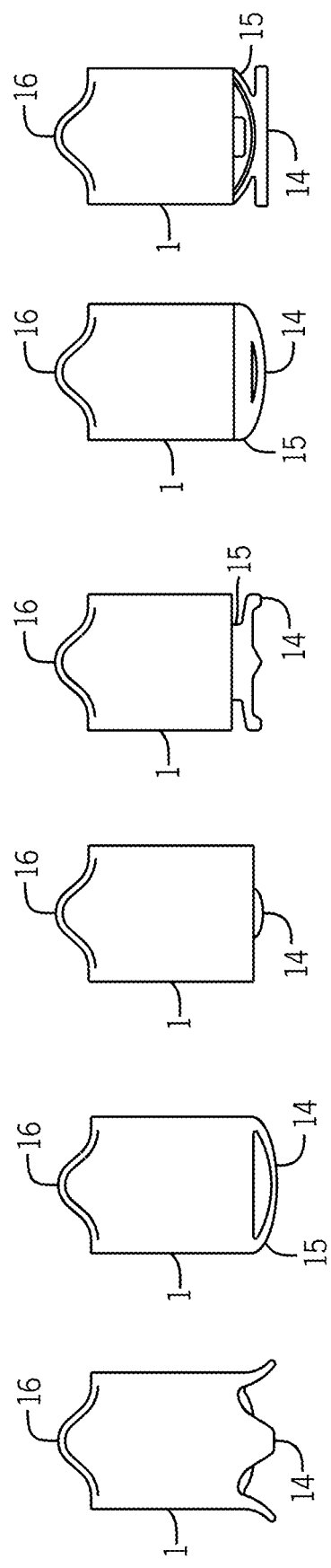

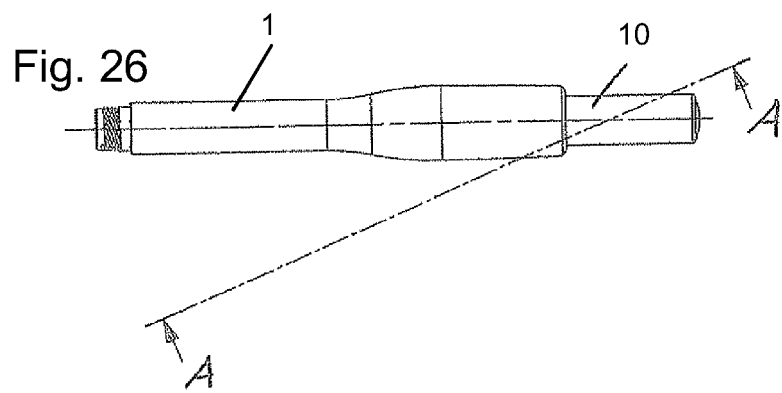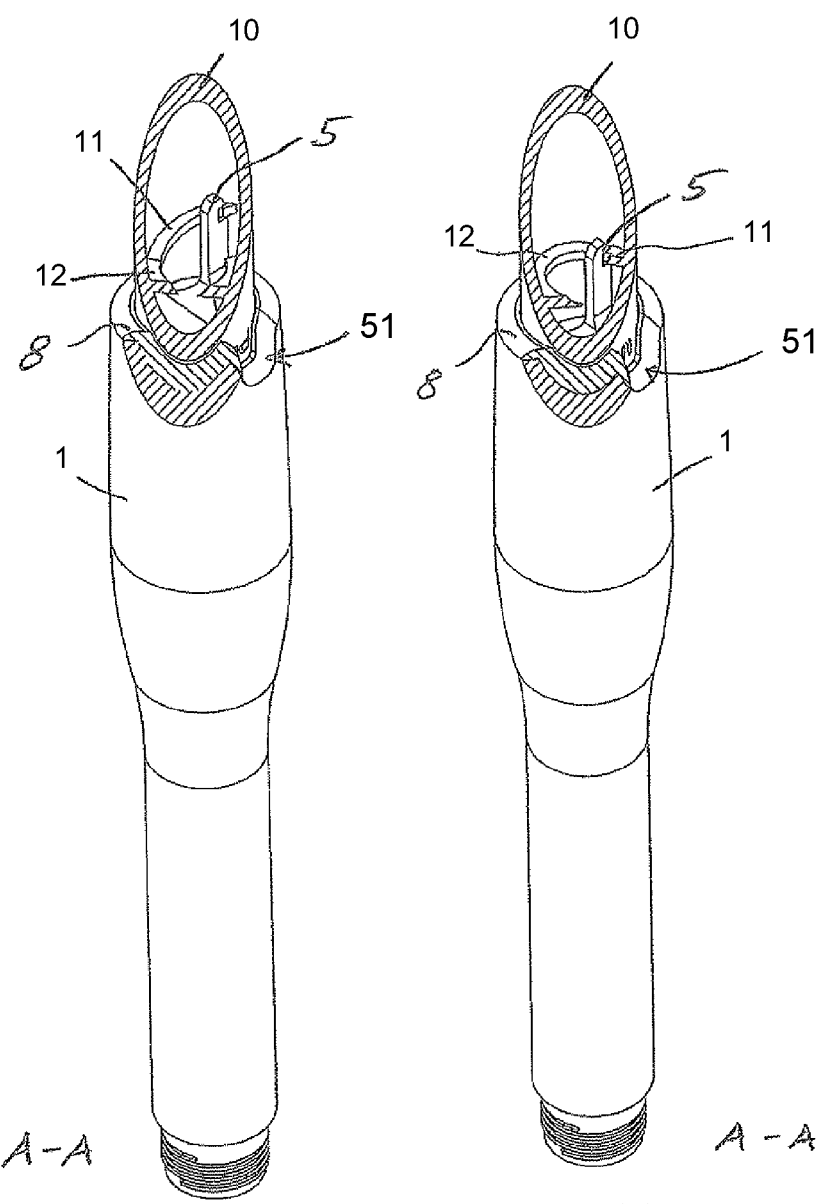

Fig. 31
Fig. 32
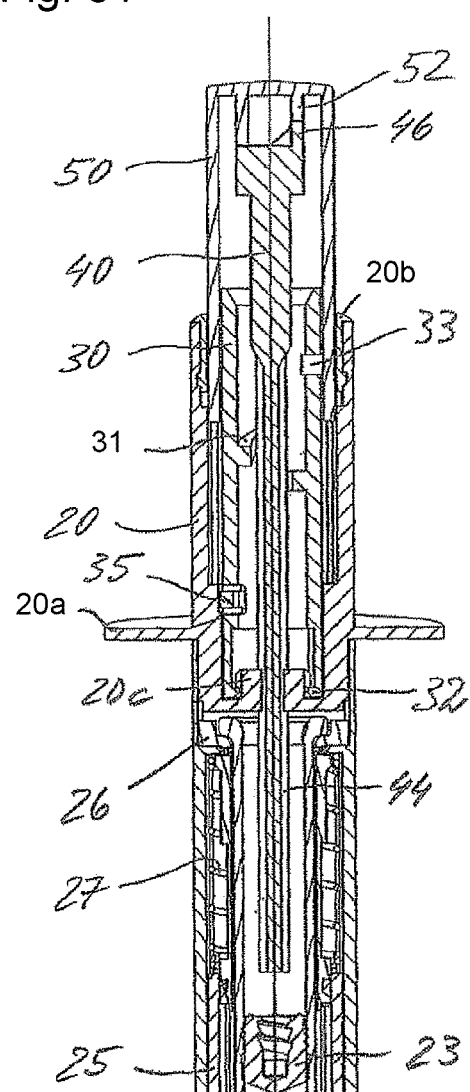
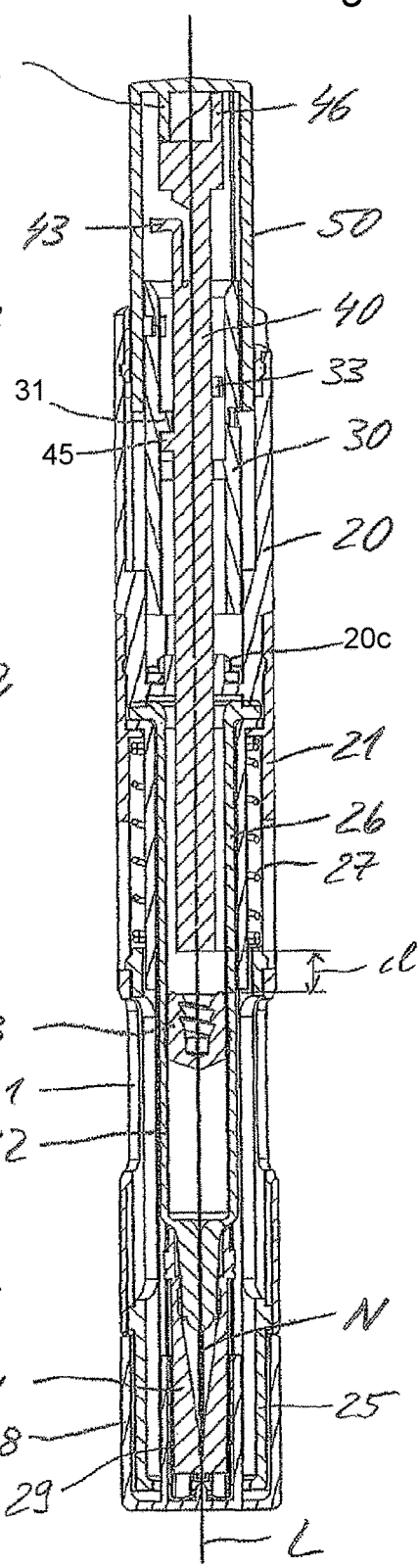
Fig. 30
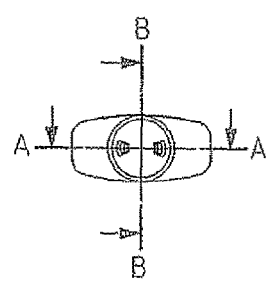
A-A    B-B

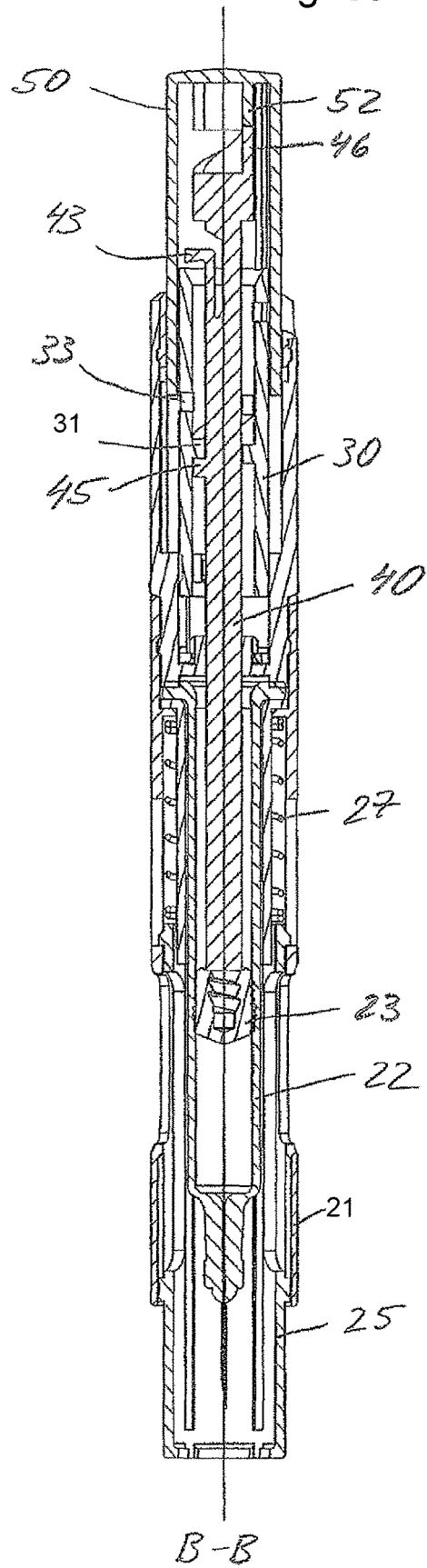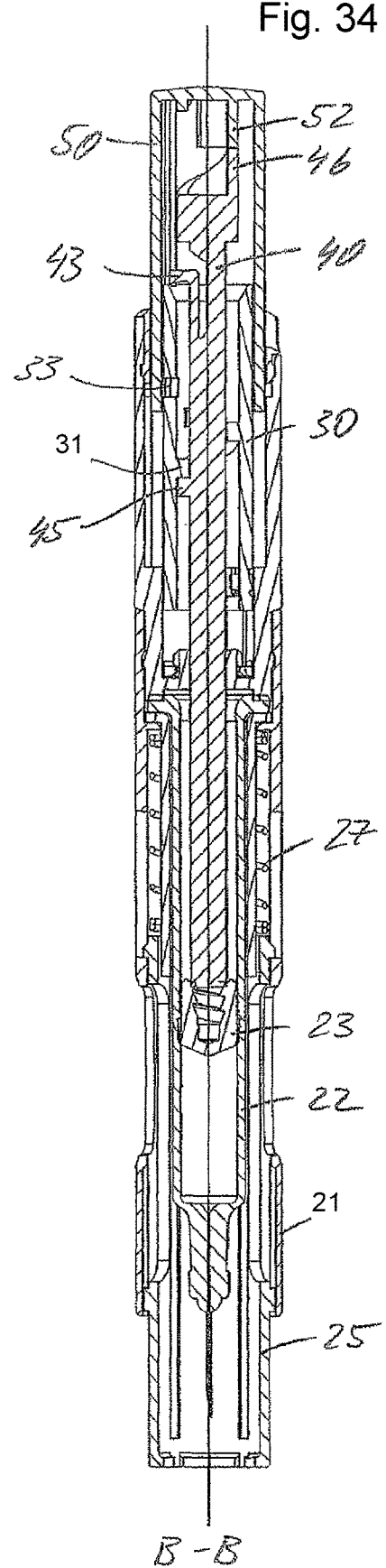

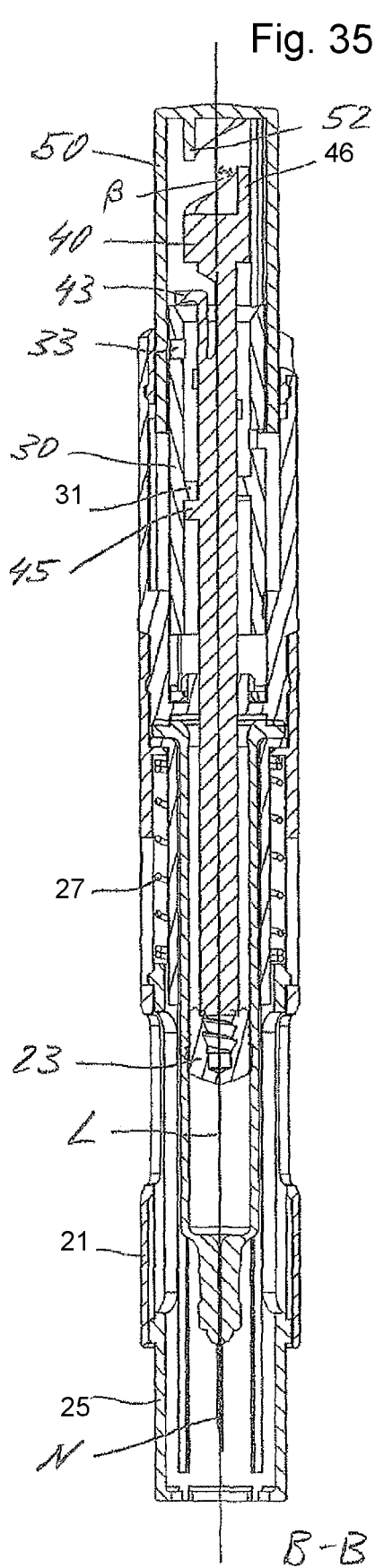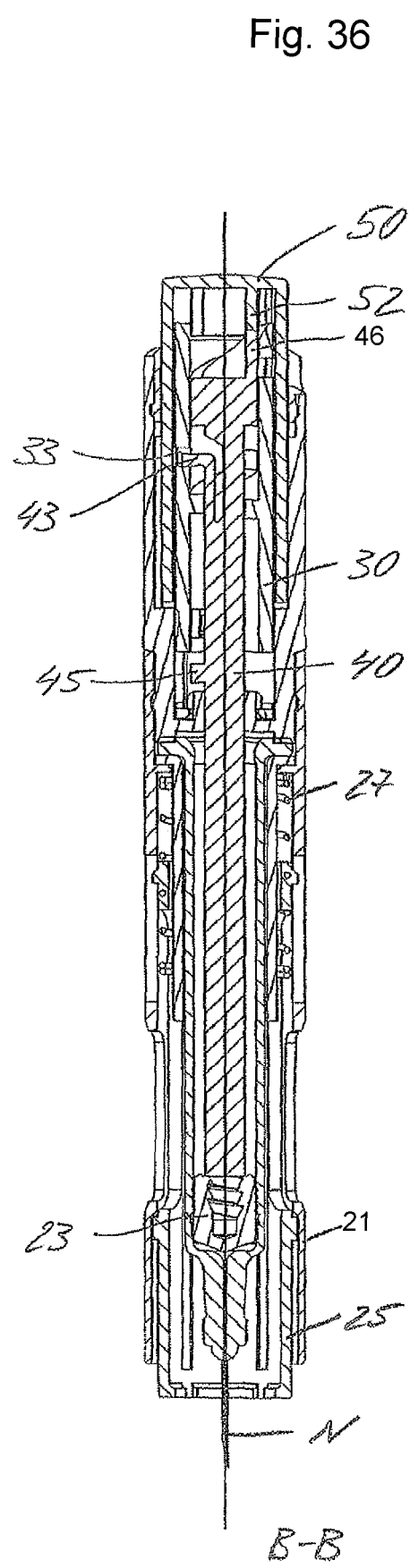

Fig. 37
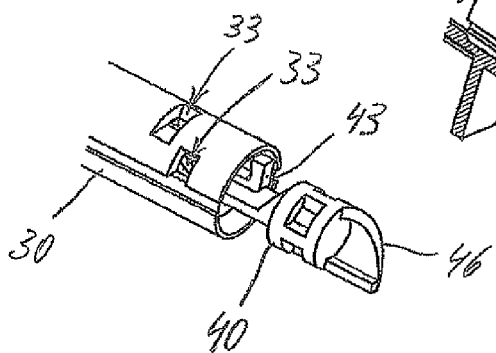
Fig. 38
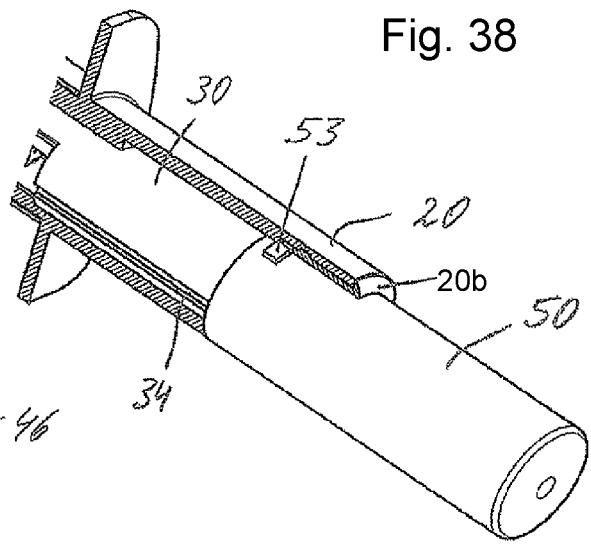
Fig. 40 VIEW E
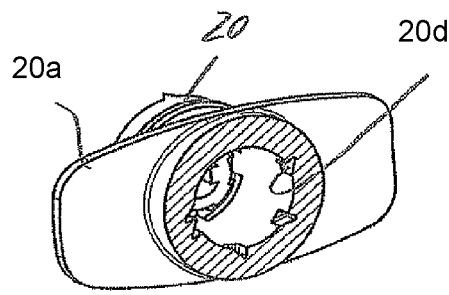
Fig. 39
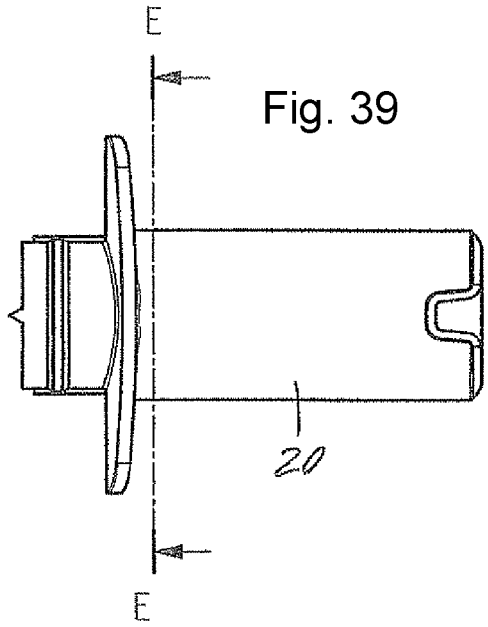
Fig. 41
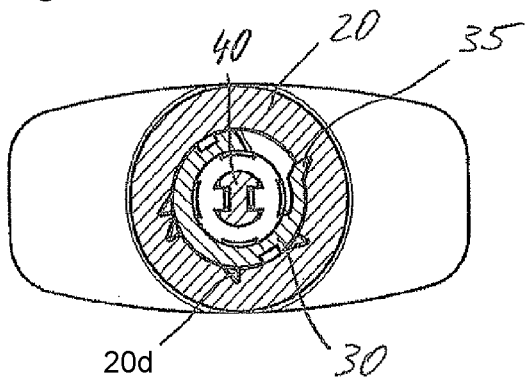
Fig. 42
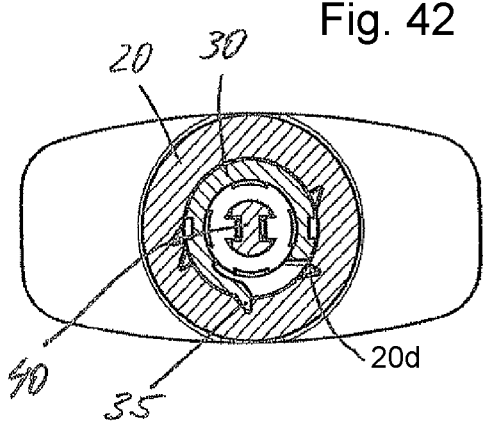

Fig. 45
Fig. 46
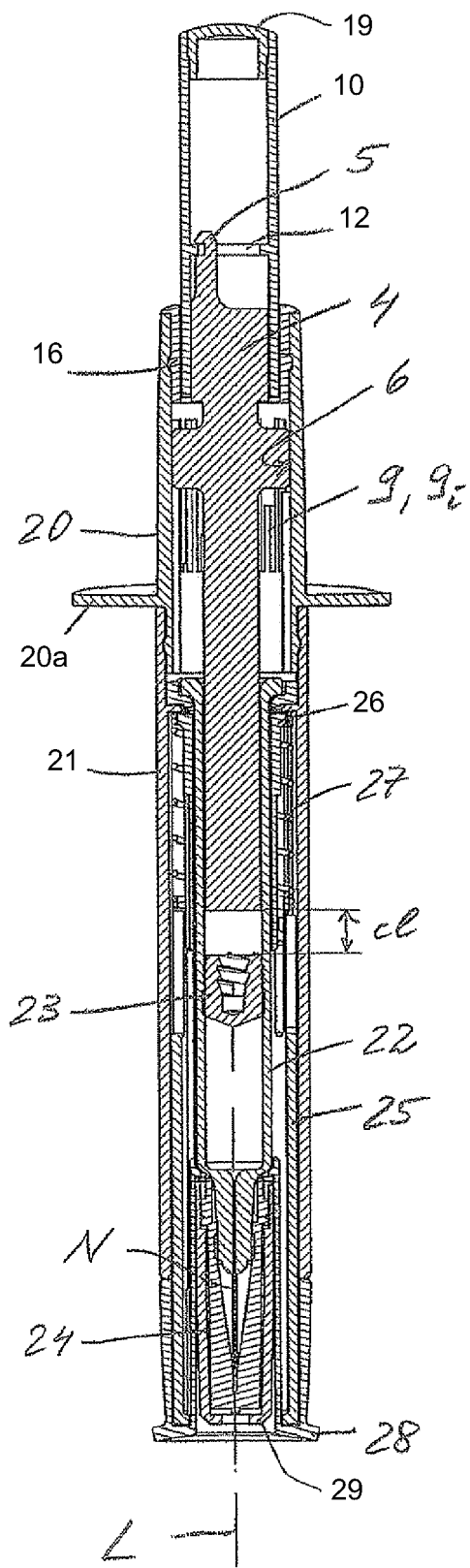
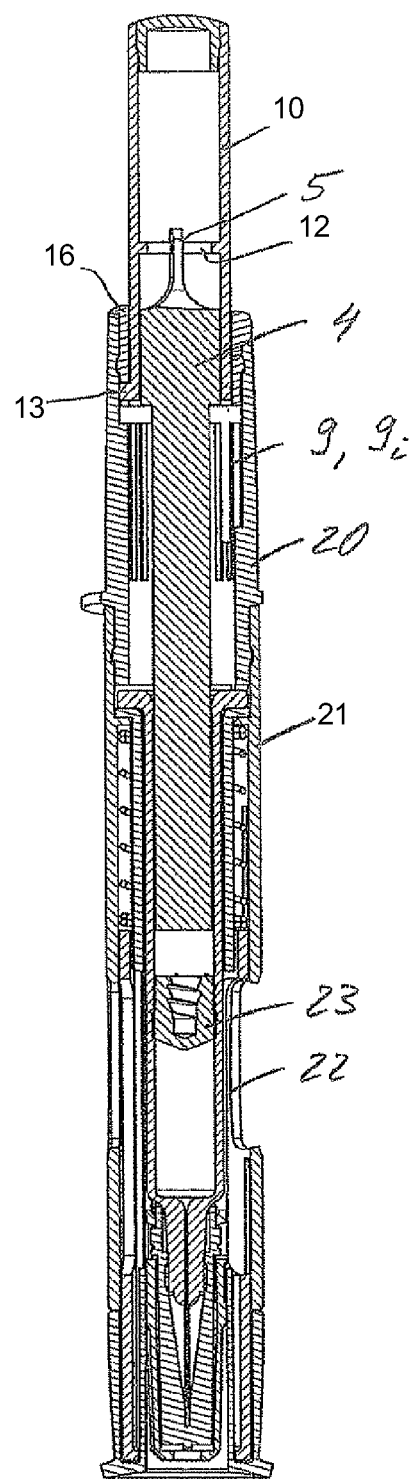

Fig. 47
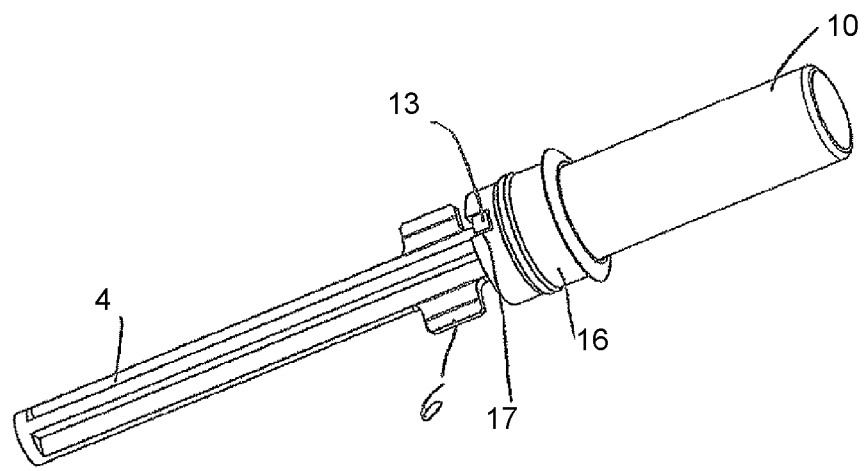
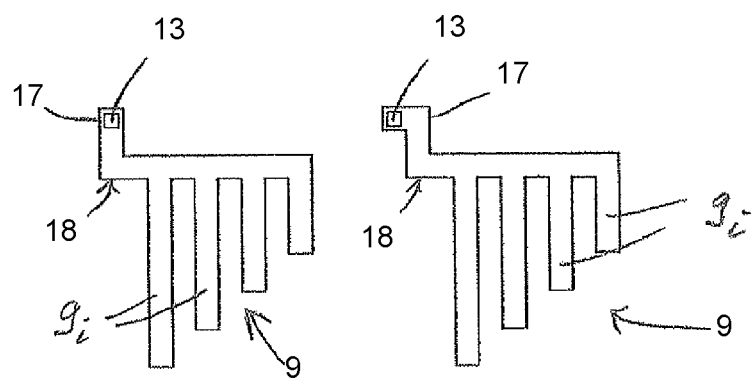
Fig. 48  Fig. 49

INJECTION DEVICE WITH DOSING CONTROL MEANS

CROSS-REFERENCE TO RELATED APPLICATIONS

This application is a continuation of U.S. patent application Ser. No. 14/664,536 filed Mar. 20, 2015, issued as U.S. Pat. No. 10,149,945 on Dec. 11, 2018, which is a continuation of International Patent Application No. PCT/EP2013/060673 filed May 23, 2013, which claims priority to Swiss Patent Application No. 01875/12 filed Oct. 8, 2012; the entire contents of each are incorporated herein by reference.

TECHNICAL FIELD

A first aspect of the invention (which is also called "Injection device with dosing control means") is directed to an injection device according to the independent apparatus claim and a method of assembling an injection device in accordance with the independent method claim.

BACKGROUND

When using an injection device for injecting a medical fluid such as a liquid drug into a patient's body, the injection device has to be primed, i.e., the reservoir in which the liquid drug is stored has to be de-aired. Otherwise, a risk of injecting air into the patient's blood vessels may arise which might lead to an embolism. Many injection devices therefore incorporate a means for priming the injection device. Such a priming means in general requires the injection device to be primed before a dose of the fluid to be injected can be selected. In such injection devices, a user may erroneously move the priming means back into a position which it had before priming or at the end of the priming operation which may lead to undesired accumulation of air in the reservoir.

SUMMARY

A problem to be solved by a first aspect of the present invention therefore is to provide an injection device which on the one hand requires a user to first prime the injection device before selecting a dose to be injected and on the other hand avoids undesired accumulation of air in the reservoir after a priming operation has been completed.

This problem is solved by the subject matter of the independent claims, wherein the dependent claims relate to preferred embodiments of the first aspect of the present invention.

The inventive injection device preferably comprises a casing which accommodates or forms a reservoir for a drug, in particular a fluid drug such as a liquid drug. The casing preferably comprises an outer structure of the injection device, i.e., a structure which comprises an outer surface of the injection device. In particular, the casing also serves as a holding means for the injection device with which a user holds the injection device for operating it. The injection device may be any one of a manually operated syringe and an injection device comprising a mechanism for automatic execution of an injection and discharge sequence (in particular, represented by an auto-injector). For example, the casing comprises a sleeve which surrounds the reservoir. Preferably, the sleeve is cylindrical and hollow in its interior in order to accommodate the reservoir. Preferably the casing comprises, in particular, accommodates a reservoir holder (e.g., a syringe holder) for holding the reservoir. According to a preferred embodiment, the casing comprises a first casing part and a second casing part (which is, in particular, different from the first casing part, i.e., is not comprised in the first casing part). The second casing part can preferably be coupled to the first casing part, in particular, such that the first casing part and the second casing part cannot move relative to each other in an axial direction of the injection device.

The axial direction of the injection device is a direction which extends in the direction of a longitudinal axis of the injection device (e.g., a cylinder axis if the injection device possesses a substantially cylindrical shape). A distal and/or forward direction of the injection device is parallel to the axial direction and points, in particular, in the direction in which the medical fluid is to be expelled (therefore, it points towards a forward and/or front and/or distal end of the injection device at which a discharge means for discharging a fluid such as a needle is disposed). A proximal and/or backward direction of the injection device also runs parallel to the axial direction and points in particular towards a backward and/or rear and/or proximal end of the injection device which lies opposite the distal end at which in particular an activation means such as an operation knob which is coupled to a plunger rod for applying a discharging force is disposed. During injection, the distal end of the injection device points in particular towards a location of the patient's body at which the injection is to be performed (i.e., an injection location).

The first casing part preferably is a part of the casing which lies further to the distal end than the second casing part which preferably lies further towards the proximal end. In a delivery state in which the injection device is delivered to the user, the first casing part and the second casing part are preferably not coupled to each other. For coupling the first and the second casing part to each other, the second casing part is for example screwed to the first casing part, each casing part therefore preferably has a corresponding screw thread. For example, both the first casing part and the second casing part have the basic geometry of a hollow cylinder, the first casing part comprises an internal thread on its interior surface at its proximal end, and the second casing part comprises a screw thread on its external surface at its distal end. The second casing part can then be screwed into the first casing part. Preferably, the first casing part and the second casing part are then coupled to each other such that they cannot move relative to each other in an axial direction. Further preferably, they are also coupled to each other such that they cannot rotate relative to each other. For example, at least one of the first and second casing parts may be provided with a coupling means embodied by, e.g., an engagement means which engages a groove on the other one of the first and second casing parts at the end of the screwing operation and which prevents unscrewing the first and second casing parts from one another. According to another embodiment of the first aspect of the invention, the first and second casing parts may be coupled to each other with a coupling means embodied for example by a snap-fit between, for example, an engagement means such as a flexible hook provided on at least one of the first and second casing parts and a corresponding holding means into which the hook is snapped when coupling the first and second casing parts.

According to a particularly preferred embodiment of the first aspect of the invention, the coupling means comprises an engagement means which takes the form of at least one circumferential rib (preferably, two circumferential ribs) on an outer surface of the second casing part which is inserted into the proximal end of the first casing part. The first casing part preferably comprises a holding means embodied by at least one circumferential notch (the number of notches being preferably equal to the number of ribs on the second casing part) in which the circumferential ribs on the second casing part are configured to lie after coupling the first casing part and the second casing part. In order to prevent a rotation of the first casing part relative to the second casing part after coupling them to each other, the injection device preferably comprises a casing rotation blocking means, which includes for example at least one axial rib on an outer surface of the second casing part which is inserted into the first casing part, and the first casing part comprises at least one axial notch (the number of notches being preferably equal to the number of axial ribs on the second casing part) in which the axial rib of the second casing part is configured to lie after coupling the first casing part to the second casing part. The coupling means comprises at least the engagement means and the holding means, preferably the holding means also comprises the casing rotation blocking means. In the case of more than one axial rib on the second casing part, the axial ribs are preferably of different axial length, and the corresponding axial notches on the first casing part are preferably of different axial length, the axial notches of different lengths each being designed to accommodate one of the axial ribs having a corresponding axial length. Furthermore, the pairs of corresponding axial ribs and axial notches are positioned in the axial direction such that, if the first casing part and the second casing part are positioned in a rotational position (in the sense of a rotation along their longitudinal axes) such that an axial rib lies in an axial notch of shorter length than the axial rib, the second casing part cannot be coupled to (in particular not fully inserted into) the first casing part. Such a configuration corresponds to a delivery state of the injection vice in which it is delivered to a user. In that configuration, preferably only one of a possible plurality of the circumferential ribs on the second casing part lies in one of the possible plurality of circumferential notches in the first casing part. In particular, the more distal circumferential ribs lies in the more proximal circumferential notch. In that configuration the second casing part and the first casing part remain detachable from one another. This configuration may therefore also be denoted as a partly coupled configuration of the coupling means.

The reservoir may be an integral feature of the casing or be present in the form of the reservoir of a syringe which is filled with a medical fluid to be injected. In particular, the reservoir is not formed integrally with the casing and may be inserted into the casing, in particular into the first casing part, before coupling the first casing part and the second casing part. During operation of the injection device, in particular when the reservoir is accommodated by the casing, further particularly during injection, the reservoir preferably rests or is stationary relative to the casing, in particular relative to the first casing part.

The injection device furthermore preferably comprises a plunger rod which can move relative to the casing in an axially forward direction to deliver the drug. The plunger rod in particular is configured to move a piston in the reservoir in particular in the distal direction in order to increase the pressure on the drug such that it is discharged from the reservoir. The plunger rod is preferably connected to an activating means such as an operating knob at its proximal end on which the user can exert for example manual pressure in order to move the plunger rod into the distal direction. The activating means and the plunger rod may be formed integrally, i.e., as one part, or as separate parts which have a preferably fixed position (in particular in an axial direction, preferably also in a rotational direction) relative to each other.

The injection device preferably also comprises a dosing means which can move in the forward direction relative to the casing in order to prime the reservoir, i.e., to de-air it. The dosing means is preferably provided on the casing, in particular the second casing part, and for example takes the form of a cylindrical hollow sleeve which is movable relative to the second casing part. For example, the dosing means is accommodated by the second casing part, in particular an outer casing part of the second casing part such as a proximal end cap of the casing which is part of the second casing part. Preferably, the dosing means can rotate relative to the casing, in particular relative to the second casing part, for selecting a dose to be injected. Furthermore, the dosing means accommodates at least part of the plunger rod and in particular also the activating means and preferably can also rotate relative to the plunger rod and/or the activating means. For example, the dosing means is provided with an internal circumferential groove in which a corresponding circumferential projection of the plunger rod and/or activating means (in particular a sum piece) is located such that an axial movement of the dosing means relative to the plunger rod and/or the activating means is prohibited.

Preferably, rotation of the dosing means relative to the casing is prevented in particular before (more particularly, until) a priming operation for priming the reservoir is completed. In particular, such a rotation of the dosing means is prevented after coupling the first casing part to the second casing part. The dosing means preferably comprises a dosing control means which is configured to prevent or enable rotation, respectively, of the dosing means. The dosing control means comprises an engagement means (for example a protrusion provided on an exterior surface of the dosing means) and engages with a rotation prevention means embodied by, e.g., a groove on the interior surface of the second casing part. The protrusion is configured to lie in the groove in particular after coupling the first casing part and the second casing part to each other. The engagement means is configured to engage the rotation prevention means in particular before (more particularly until) the priming stroke is completed. The groove preferably is open at least in a distal direction such that, upon moving the dosing means in the forward direction relative to the casing, the protrusion exits the groove in order to enable rotation of the dosing means relative to the casing, in particular relative to the second casing part. The groove is preferably dimensioned in particular in its axial direction such that the distance which the protrusion of the dosing means has to travel in order to enable its rotation (i.e., to exit the groove) is equivalent to (in particular equal) the distance which the plunger rod has to travel during a priming stroke. The dosing control means furthermore preferably comprises a deflecting means (e.g., a protrusion on its interior surface in particular at its distal end) which, in particular after coupling the first casing part and the second casing part to each other, is aligned with a rotation limitation means disposed on the casing, in particular the second casing part, and which, during forward movement of the dosing means for priming clears the rotation prevention means, in particular deflects it (preferably in a radially inward direction). The deflecting means is configured to deflect the rotation limitation means in particular at the end of the priming stroke. The rotation limitation means is configured such that it prohibits complete rotation (in particular around the whole circumference of the injection device by in particular 360°) of the dosing means relative to the casing in particular after the dosing means has been rotated out of the position which it attains at the end of the priming stroke. It is also configured such that the dosing means is allowed to rotate only partially (i.e., less than a complete rotation, i.e., less than) 360° relative to the casing in particular after the dosing means has been rotated out of the position which the dosing means attains at the end of the priming stroke. Such a rotation which is allowed for only less than 360° around the axial direction is also called a limited rotation.

For example, the second casing part comprises the aforementioned outer casing part and a plunger rod guiding means which may be formed integrally with each other or as separate structures. Preferably, the plunger rod guiding means is disposed in the interior of the outer casing part and the rotation limitation means is located on the plunger rod guiding means. For example, the plunger rod guiding means has the basic shape of a hollow cylinder, in the interior of which the plunger rod is guided, and is provided with the rotation limitation means which may be embodied for example by a spring disposed in an exterior surface of the plunger rod guiding means. Preferably, the plunger rod guiding means is disposed such that it is at least partially surrounded by the dosing means. In summary, the plunger rod guiding means is preferably at least partly surrounded by the dosing means, and the dosing means is preferably at least partly surrounded by the outer casing part.

The deflecting means preferably has a circumferential extent on the interior surface of the dosing means which covers only part, i.e., not all, of the interior circumference of the dosing means. In particular, at least a part of the interior circumference corresponding to the circumferential extent of the rotation prevention means is not covered by the deflecting means. This means, when the dosing means is rotated in a circumferential direction, the deflecting means is moved circumferentially away from the rotation prevention means which then (due to its elasticity) moves back into its position which it had before initiating the priming stroke, in particular it moves in a radially outward direction. The deflecting means comprises in particular a slanted surface at its distal end such that it can be pushed over the rotation limitation means in order to deflect the rotation limitation means in particular in a radially inward direction of the injection device. The rotation limitation means preferably is elastic such that, after moving the deflecting means in a circumferential direction away from the rotation limitation means, the rotation limitation means moves back into its position which it had before initiating the priming stroke, in particular before being deflected by the deflecting means. Since both the rotation limitation means and the deflecting means preferably have a reversal prevention means which prevents a reverse movement of the dosing means into the position which it had at the end of the priming stroke (such as side surfaces on both the deflecting means and the rotation limitation means parallel to an axial direction which run in a substantially radial direction), it will not be possible to rotate the dosing means back into the position relative to the casing which it had at the end of the priming stroke. In such a case, the axial side surface of the deflecting means would abut the axial side surface of the rotation limitation means without being able to be moved over the rotation limitation means, i.e., without being able to deflect the rotation limitation means again. The dosing control means therefore is preferably configured to prevent a rotation of the dosing means back into the position which the dosing means had at the end of the priming stroke relative to the casing. The dosing means is rotated in particular in order to select a dose of the medical fluid to be injected, the dosing control means is therefore further configured to abut the rotation limitation means as soon as the dosing means has been rotated for selecting the dose, in particular after selecting the dose.

Preferably, the dosing means comprises a dose defining means which is configured to define the dose to be injected. The dose defining means comprises for example at least one dose defining groove (in particular a plurality of grooves) disposed on the interior surface of the dosing means and running in an axial direction. The length of each dose defining groove defines the dose to be injected. The dose defining means preferably comprises a dose locking means which is constituted to lock the dosing means at the end of a discharge operation for discharging the medical fluid (in particular at the end of a discharge stroke). For example the dosing means a dose locking means which is configured to lock the dosing means in particular after discharging the medical fluid from the reservoir in particular such that the dosing means cannot move relative to the casing. For example, a dose locking means comprising a protrusion disposed at the proximal end of each dose defining groove. The dose locking means preferably comprises a dose blocking means which is disposed in particular on the casing, more particularly on the second casing part such as on the plunger rod guiding means. For example, the dose blocking means comprises an elastic member which can be depressed by the dose locking means when the plunger rod and therefore also the dosing means are moved in a distal direction and in particular at the end of the discharge operation. In particular, the protrusion of the dose locking means engage the dose blocking means in particular by snapping over the elastic member of the dose blocking means at the end of the discharge operation in such a manner that moving the dosing means in the proximal direction after completing the discharge operation is prevented. In particular, the protrusion of the dose locking means has a surface at its proximal side which runs in a substantially radial direction and the dose blocking means has a surface at its distal side which also runs in a substantially radial direction such that, if a user tries to move the dosing means in a proximal direction after completing the discharge operation, the dose blocking means and the protrusion abut each other, thereby preventing the proximal movement of the dosing means. Additionally, the dose blocking means preferably comprises a protrusion which, at completion of the discharge operation, lies distally of and abuts the protrusion of the dose locking means. This protrusion serves to limit a forward movement of the dosing means and therefore also the plunger rod to the distance necessary to discharge the selected volume (dose) of the medical fluid. According to a very preferred embodiment of the first aspect of the invention, the rotation limitation means is at least partly identical to the dose blocking means. For example, the elastic member of the dose blocking means also serves as the rotation limitation means.

Preferably, the injection device comprises a plunger rod guiding means which is in particular part of the second casing part. The plunger rod guiding means preferably has the basic shape of a hollow cylinder, in the interior and in the axial direction of which the plunger rod is able to move in particular in the distal direction in order to effect discharge of the medical fluid. The plunger rod guiding means preferably comprises at least one guide rail which engages a respective at least one axial protrusion on the plunger rod such that the plunger rod cannot rotate relative to the plunger rod guiding means. Preferably, the plunger rod guiding means comprises two such guide rails which each comprises two axial protrusions on an inner surface of the plunger rod guiding means which lie opposite both sides of the axial protrusion of the plunger rod. The axial protrusion of the plunger rod is able to move in an axial direction in the guide rail by which it is surrounded. Furthermore, the plunger rod guiding means preferably comprises at least one elastic member which is able to move in a radial direction of the injection device, i.e., in a direction perpendicular to the axial direction. The elastic member preferably serves as a rotational blocking means which is configured to block an axial movement of the plunger rod relative to the casing in particular in a proximal direction. The axial blocking means is configured to co-operate with at least one radial protrusion on the plunger rod which, during distal movement of the plunger rod, deflects the axial blocking means in a radially outward direction so as to enable movement of the plunger rod relative to the axial blocking means. If the plunger rod is then moved further in a distal direction, the axial blocking means preferably moves back into its previous position which it had before being deflected by the radial protrusion of the plunger rod. The axial blocking means and the radial protrusion on the plunger rod then lie opposite each other and in particular have respectively configured surfaces which prohibit a proximal movement of the plunger rod for example by an abutment between the axial blocking means and the radial protrusion. Preferably, the plunger rod has at least one, in particular a plurality, of such radial protrusions on one of its sides and a corresponding number of radial protrusions on a diametrically opposite side at diametrically opposite positions.

The plunger rod guiding means is preferably disposed in an outer casing part which is in particular part of the second casing part and is embodied in particular by an end cap. The plunger rod guiding means preferably comprises holding means for holding the plunger rod guiding means in the outer casing part in particular such that the plunger rod guiding means and the outer casing part are moveable relative to each other for example in an axial direction (in particular before completing coupling of the first casing part to the second casing part). It is preferred that the plunger rod guiding means and the outer casing part are moveable relative to each other before coupling the first casing part to the second casing part. For example, the plunger rod guiding means comprises hooks which are disposed on radial projections at diametrically opposite oppositions on an outer surface of the plunger rod guiding means. The outer casing part preferably comprises at least one recess (the number of recesses corresponding to the number of hooks on the plunger rod guiding means) in which the hooks may lie. The recesses are preferably dimensioned such that the hooks are able to move within the recesses in particular before completing coupling of the first casing part to the second casing part. The hooks are preferably configured to abut a distal limitation of the recess in order to prevent the plunger rod guiding means from being extracted out of the outer casing part.

Furthermore, the second casing part (in particular the plunger rod guiding means) comprises a tensioning means for tensioning the plunger rod guiding means relative to the outer casing part. The effect of such tensioning is in particular that the plunger rod guiding means is at least substantially not moveable relative to the outer casing part in an axial direction in particular after coupling the first casing part to the second casing part. The tensioning means is preferably embodied by an elastic member, for example at least one radial protrusion (further preferably two radial protrusions at diametrically opposite positions) on an outer surface of the plunger rod guiding means at advantageously its distal end. In particular the elastic member, when coupling the second casing part to the first casing part, abuts the distal circumference of the outer casing part with its radially outer end and is pressed, at its base (i.e., at the radially inner end of a protrusion forming the elastic member) in a proximal direction by a force exerted on it by the first casing part or the reservoir (for example the proximal flange of the syringe) in a proximal direction. The elasticity of the tensioning means is preferably designed such that for example syringe flanges of differing thickness may be accommodated by the inventive injection device while ensuring in co-operation with the dimensioning of the recess (or recesses, respectively) in the outer casing part and the size of the holding means of the plunger rod guiding means that the plunger rod guiding means is stably held in a fixed (in particular axial and preferably also rotational) position relative to the casing after assembling the injection device (i.e., after coupling the second casing part to the first casing part comprising the reservoir). In accordance with the aforementioned description, this is achieved by a form-force fit between the first casing part or the reservoir, the outer casing part and the plunger rod guiding means.

Preferably, the tensioning means comprises a spacing means which is configured to space the second casing part from the reservoir (for example a syringe) in particular after (if necessary) inserting the reservoir into the first casing part and more particularly after coupling the first casing part to the second casing part. The spacing means is preferably embodied by an axial protrusion on the distal end of the plunger rod guiding means. Preferably, a plurality of such protrusions is disposed in the circumferential direction of the plunger rod guiding means at its distal end.

In summary, the movability of the plunger rod guiding means relative to the outer casing part before assembling the injection device and the aforementioned form-force fit provide a multi-part injection device which may accommodate syringes of different sizes in particular while allowing easy assembly of the injection device into a mechanically stable structure.

Preferably, the dosing means comprises a ratchet means comprising recesses and protrusions which are configured to co-operate with recesses and protrusions having a fixed position relative to the plunger rod. In particular, the ratchet means comprises recesses and protrusions which are preferably disposed on the plunger rod. During rotation of the dosing means relative to the plunger rod (for example when selecting a dose to be injected), the recesses and protrusions which are alternately disposed along an inner circumference of the dosing means (for example at its proximal end) move over the recesses and protrusions on the plunger rod (which are for example disposed on the outer circumference of the activation means which is surrounded by the dosing means). The ratchet means is preferably configured such that it may be activated by manual force. Since the plunger rod preferably cannot rotate relative to the casing, the ratchet means is preferably activated by rotating the dosing means relative to the casing. This serves in particular to give the user a tactile and acoustic feedback during a dose selecting operation.

The injection device furthermore preferably comprises a needle shield which is in particular moveable in an axial direction and a needle shield biasing means configured to bias the needle shield in an axially forward direction. The needle shield is preferably embodied by a sleeve having the basic shape of for example a hollow cylinder which is disposed inside or around the casing (in particular the first casing part) substantially at its distal end. Before pressing the injection device onto an injection location at which the injection of the medical fluid is to be effected, the needle shield is in its forward position in which it preferably extends outside the casing over its distal end and surrounds a discharge means such as a needle comprised in the injection device. The needle shield is held in this position by the needle shield biasing means which is embodied by for example a spiral spring which abuts in particular at its proximal end the casing and at its distal end the needle shield. In the aforementioned forward position of the needle shield, the needle shield biasing means is in its relaxed state. When pressing the injection device onto the injection location, the needle shield is pressed against the biasing means which is then compressed (and therefore biased) and allows the needle shield to move in a proximal direction relative to the casing (i.e., into its backward position). In the backward position of the needle shield, a discharge means such as a needle connected to the reservoir is exposed. In its forward position, the needle shield surrounds the discharge means preferably along at least substantially the complete axial length of discharge means. In its backward position, the needle shield allows the discharge means to be at least partially exposed in order to for example pierce the skin of a patient.

The injection device furthermore preferably comprises a needle shield locking means which is configured to lock the needle shield in an axially fixed position in order to prohibit axial movement of the needle shield in particular in a proximal direction relative to the casing after performing an injection. In particular, such movement of the needle shield is prohibited after the needle shield has been moved into its backward position and the needle shield biasing means is at least partly relaxed. The needle shield locking means is embodied for example by a first axial locking member such as an elastic member such as a hook disposed on the needle shield and a second axial locking member such as an elastic member such as a counter-hook disposed on the casing (in particular on the first casing part and/or on a constituent of the first casing part such as a syringe holder). The hook of the first axial locking member is preferably configured to engage with, in particular snap over, the counter-hook disposed on the casing during backward movement of the needle shield. Once the user removes the injection device again from the injection location after performing an injection, the needle shield biasing means moves the needle shield back towards its forward position such that the hook and the counter-hook abut each other. Preferably, the counter-hook abuts the base of the hook disposed on the needle shield so that a repeated proximal movement of the needle shield is prohibited.

The injection device preferably comprises a needle protection means such as a protective cap (e.g., a needle cap, also called front cap) disposed at its distal end. The needle protection means preferably has the basic shape of a hollow cylinder which can be fitted preferably over or into the needle shield and further preferably, at its proximal end, abuts the distal circumference of the casing. The needle protection means is preferably provided with a removing means for removing a needle cover. The removing means is embodied in particular by an inner boot disposed in the interior of the needle protection means and for example has the basic shape of a hollow cylinder having a plurality of axial hooks (e.g., two such hooks) extending at its proximal end in an axial direction which are configured to engage behind a removable discharge means cover (e.g., a needle cover) disposed on the distal end of the reservoir (in particular a syringe). The discharge means cover serves to cover the discharge means (in particular the needle). The inner boot is configured to accommodate the needle cover. For example, a pre-filled syringe may be supplied which has to be fitted into the first casing part by the user, whereafter the injection device is assembled by coupling the first casing part to the second casing part. When fitting the syringe into the first casing part, the syringe is pushed in a distal direction into the casing, at the distal end of which the needle protection means is disposed. The distal end of the syringe (in particular a needle holder and the needle cover by a needle cover) is then pushed into the removing means, whereby the axial hook snap behind the proximal circumference of the needle cover. Once the user wishes to use the injection device, he removes the needle protection means (i.e., the end cap), and the axial hooks then take with them the needle cover and therefore serve as a removing means for removing the needle cover from the distal end of the syringe such that the needle is exposed to the atmosphere and may be used. In particular, the discharge means cover is removed simultaneously with removing the needle protection means from the injection device.

The needle protection means is preferably provided with a buffer means for buffering (in particular absorbing and/or damping) a mechanical action on (e.g., a mechanical shock applied to) in particular the distal end of the needle protection means. Thereby, for example damage to the syringe (e.g., to the reservoir) may be avoided if the injection device is for example dropped and falls onto the needle protection means which is still attached to the distal end of the injection device. The buffer means is preferably flexible, in particular elastic and is further preferably formed integrally with the needle protection means in particular at the distal end of the needle protection means. The buffer means can be embodied for example by a ring-shaped element (in particular a ring) which is fastened to the needle protection means at in particular at least two (preferably at exactly three) locations along its circumference with for example connecting elements running oblique to the axial direction of the injection device. The ring-shaped element may also be buckled in a radial direction so as to form a hyperbola in a lateral view. Alternatively, the buffer means can be embodied by at least one of an elastic hoop formed along the distal frontal surface of the needle protection means, a plurality of elastic projections (e.g., four such projections) formed at discrete and disjunct positions at e.g., 90° intervals around the distal circumference (e.g., on the distal frontal rim of the needle protection means or at positions at least substantially slightly radially inwards of the rim) of the needle protection means.

Further preferably, the needle protection means is provided with a gripping means which serves as a surface for in particular manual gripping by a user for e.g., pulling the needle protection means off in a distal direction. The gripping means for example takes the form of axial protrusions on the proximal rim of the needle protection means.

The first aspect of the invention also relates to a method of assembling an injection device which (in particular the injection device in accordance with the first aspect of the invention), comprising the following preferred steps:

a) providing an injection device comprising a first casing part and a second casing part which can be coupled to the first casing part;

b) providing a reservoir, in particular a syringe, for receiving a liquid drug;

c) inserting the reservoir into one of the first casing part and the second casing part; and d) coupling, in particular after inserting the reservoir, the first casing part and the second casing part to each other such that the first casing part and the second casing part cannot move relative to each other in an axial direction of the injection device.

Preferably, the first casing part and the second casing part then cannot rotate relative to each other and in particular cannot move relative to the one of the first casing part and the second casing part to which the reservoir was inserted.

The inventive method comprises the following further feature: the second casing part preferably comprises a plunger rod guiding means and an outer casing part and coupling the first casing part and the second casing part to each other preferably includes tensioning the plunger rod guiding means relative to the outer casing part.

The first aspect of the invention also relates to the following aspect which comprises the features defined in the following and may be claimed for separately and irrespective of the wording of the above-explained embodiments and the appended claims in particular by way of filing a divisional application or other continuation application. Any terminology used for this aspect which corresponds to the terminology used in the preceding text defines the same features which are denoted by the corresponding terminology in the above text.

A. An injection device, comprising:
  a) a casing which accommodates or forms a reservoir for a liquid drug, wherein the casing comprises a first casing part and a second casing part which can be coupled to the first casing part;
  b) a plunger rod which can move relative to the casing to deliver the drug;
  c) wherein the second casing part comprises a plunger rod guiding means for guiding the plunger rod and an outer casing part;
  d) a holding means for holding the plunger rod guiding means in the outer casing part and a tensioning means for tensioning the plunger rod guiding means relative to the outer casing part.

B. The injection device according to embodiment A, further comprising a coupling means for coupling the second casing part and the first casing part to each other.

C. The injection device according to embodiment B, wherein the coupling means is in a partly coupled state when the injection device is in a delivery state.

D. The injection device according to embodiment A, wherein the holding means comprises at least one recess provided in the outer casing and at least one engagement means on an outer surface of the plunger rod guiding means which is configured to be disposed in the recess.

E. The injection device according to any one of embodiments A, B, C and D, wherein the tensioning means comprises an elastic member disposed in a radial direction on an outer surface of the plunger rod guiding means.

F. The injection device according to any one of embodiments A to E, wherein the tensioning means comprises an abutment means disposed at a distal end of the plunger rod guiding means.

G. The injection device according to embodiment F, wherein the abutment means is configured to abut at least one of the first casing part and the reservoir.

Injection Device with Control and Entrainment Track

In the following, a second aspect of the invention is described which is also called "Injection Device with Control and Entrainment Track".

The second aspect of the invention relates to an injection device for a liquid drug. For the purpose of the second aspect of the invention, "liquid drug" is regarded as meaning not only liquids in the narrower sense but also pasty and gelatinous drugs, providing such drugs can be delivered in a way comparable to a liquid. The injection device can be one for injection by means of an infusing injection needle, e.g., a subcutaneous or intra-muscular injection, but can in principle also be an injection device for injection without a needle. Pen-shaped devices, so-called injection pens, are an advantageous choice.

Modern injection pens enable the drug to be precisely dosed, even individually by the respective patient personally. The increased flexibility due to the freely selectable dosage enables the device to be used in therapies in which the patients administer the respective drug to themselves, so-called self-administering. Self-administering in particular demands a high level of operational security and operational convenience. The devices should inherently prevent operational errors. One source of error is air trapped in the drug reservoir, another source is clearance due to manufacturing tolerances. If air is not removed and/or the clearance not eliminated before administering, there is a danger that the drug will not be administered in the dosage set but rather together with the trapped air and/or reduced by clearance elimination upon administering. The clearance is therefore eliminated and/or the drug reservoir vented or de-aerated before administering, a process which is generally known by the term "priming". In the majority of devices, priming is left to the instinct of the patient, who for this purpose sets a small dosage on a dosing member, holds the device with the needle pointing upwards, and delivers the priming volume set into the air by activating the device.

Other devices, for example a device known from EP 0 927 058 A1, are specially equipped with priming mechanisms which however entail a highly complex design and therefore significantly increased costs.

EP 1 185 322 B1 discloses an injection device with a priming mechanism formed by the interaction of a plunger rod and a casing of the device. The plunger rod is provided with a complex system of tracks on its outer circumferential surface and the casing with internal protrusions forming two sets of cam followers which interact with the tracks such that the dosage cannot be selected before the plunger rod has performed an axial priming stroke. Providing the tracks and followers exclusively at the housing and the plunger rod makes these components complicated to manufacture by plastic molding processes and the device sluggish to operate. Also, the patient can become confused because of the different operations he has to perform for priming, dosage selection and delivering of the dosage.

It is an object of the second aspect of the invention to provide an injection device which can be used in therapies involving self-injection, which is simple in design and inexpensive, but still reliably ensures that precisely the required dosage is administered, together with a level of operational convenience which is adequate for self-administration.

The second aspect of the invention proposes an injection device which comprises a casing, a reservoir for a liquid drug, a plunger rod for delivering the drug from the reservoir, and an actuating means which can be actuated by the user, e.g., the patient, to effect drug delivery or dosage selection, if the injection device allows for dosage selection.

The casing can form the reservoir directly, e.g., like a syringe. Alternatively, the reservoir can be provided as a drug container, e.g., as a carpoule or a syringe, which is or can be accommodated by the casing. The plunger rod can move relative to the casing axially, along a device axis, in a forward direction to perform a delivery stroke for delivering the drug. The actuating means can move in the forward direction relative to the casing and rotate relative to the casing and also relative to the plunger rod.

The actuating means and the plunger rod are coupled by means of a coupling which transfers a rotational movement and also an axial forward movement of the actuating means to the plunger rod such that the same is advanced in the forward direction.

The coupling comprises, under a first aspect, a curved control track and a curved entrainment track, both tracks being curved about the device axis. The control track has an inclination angle, in the following simply "inclination", which is greater than 0° and smaller than 90° with respect to the forward direction, and the entrainment track has an inclination greater than 0 and at most 90° with respect to the forward direction. The coupling furthermore comprises a control member which drivingly engages the control track to form a cam drive which couples the actuating means to the plunger rod such that a rotational movement of the actuating means forces the plunger rod into the forward direction. The control member can in particular be a cam or also an elongated track.

The coupling may comprise an entrainment member in addition to the control member. Alternatively, the control member can constitute also an entrainment member, an additional entrainment member being not required in such embodiments. The control and entrainment member or, alternatively, the additional entrainment member can be brought into engagement with or engages the entrainment track such that the actuating means, when moving in the forward direction, carries the plunger rod along in the forward direction by means of the engagement of the entrainment track with the respective member, either the control member or the additional entrainment member, if present.

An embodiment of the second aspect the invention is directed to an injection device which comprises:
  a) a casing which accommodates or forms a reservoir for a liquid drug;
  b) a plunger rod which can move relative to the casing in a forward direction of a device axis for delivering the drug;
  c) an actuating means which can rotate relative to the casing and the plunger rod to select a drug dosage to be delivered and which can move in the forward direction relative to the casing for delivering the selected dosage;
  d) an entrainment track curved about the device axis;
  e) and an entrainment member which drivingly engages the entrainment track to form a drive connection which couples the actuating means to the plunger rod such that the actuating means, when moving in the forward direction, carries the plunger rod along in the forward direction by means of the engagement with the entrainment track;
wherein the engagement of the entrainment member and the entrainment track allows for the rotational movement of the actuating means relative to the plunger rod.

Under the second aspect the cam drive formed by the engagement of the inclined control track and the control member must not be present. The cam drive disclosed previously may however be present and may be formed and arranged as described previously.

The entrainment track can under both aspects have an inclination of 90° with respect to the forward direction, i.e., be extended only in a plane which is orthogonal to the forward direction. In embodiments in which the control track or the entrainment track is/are formed threadlike, "inclination=90°-pitch angle" holds.

A plunger can under both aspects already inherently be arranged in the reservoir, i.e., arranged in the reservoir by the manufacturer and not by the patient. The plunger rod and the plunger can be formed in one piece. Alternatively, the plunger rod can be connected in a positive fit or a non-positive fit to a separately formed plunger. More preferred however the plunger rod acts during delivering only in an axial pressing contact against the rear side of the plunger in order to move it in the forward direction within the reservoir.

The actuating means and the plunger rod can be coupled indirectly via one or more additional coupling members. The one or more additional coupling members can provide the entrainment track and the entrainment member under the second aspect and can provide both tracks and the control member as well as the additional entrainment member, if the control member does not form the entrainment member already, under the first aspect. The one or more additional coupling members would be arranged movably relative to the actuating means or the plunger rod but would be coupled with the same such that the above-described coupling is established.

In preferred embodiments under both aspects, either the entrainment member or the entrainment track is arranged non-rotatably relative to the actuating means and the other one of the entrainment member and the entrainment track is arranged non-rotatably relative to the plunger rod. In addition thereto or instead of such an arrangement, either the entrainment member or the entrainment track can be arranged axially fixed relative to the actuating means and the other one of the entrainment member and the entrainment track can be arranged axially fixed relative to the plunger rod. Forming either the entrainment member or the entrainment track at the actuating means in one piece with the actuating means or forming either the entrainment member or the entrainment track at the plunger rod in one piece with the plunger rod is expedient to reduce the number of parts which have to be formed and assembled. The entrainment member can under the first aspect be formed by the control member, as mentioned.

In preferred embodiments under the first aspect, either the control member or at least one of the tracks is arranged non-rotatably relative to the actuating means and the other one of the control member and the at least one of the tracks is arranged non-rotatably relative to the plunger rod. In addition thereto or instead of such an arrangement, either the control member or at least one of the tracks can be arranged axially fixed relative to the actuating means and the other one of the control member and the at least one of the tracks can be arranged axially fixed relative to the plunger rod. Forming either the control member or at least one of the tracks at the actuating means in one piece with the actuating means or forming either the control member or at least one of the tracks at the plunger rod in one piece with the plunger rod is expedient to reduce the number of parts which have to be formed and assembled.

The injection device can feature a sequence controller which forces and in this sense controls a particular administering sequence. The actuating means can in such embodiments be blocked either in the axial or the rotational direction in a releasable priming block, in an initial state of the injection device in which the patient is preferably provided with the device, and is only released from the block at the end of a rotational or axial priming movement of the actuating means. The priming movement serves to eliminate a clearance, if present, in the drive chain from the actuating member to a plunger which directly acts on the drug, or to vent the reservoir, automatically without any additional effort by the patient, who only has to initiate the priming movement. The block for blocking the actuating means in the initial state of the injection device can be an axial block or a rotational block. The block can be formed directly between the actuating means and the casing. A rotational block, if present, is formed such that a rotational movement of the actuating means is blocked, and an axial block, if present, is formed such that an axial movement, expediently a forward movement, of the actuating means is blocked. The respective block can be formed such that it can only be released by destruction of a blocking element involved in blocking the movement of the actuating means. The respective block can alternatively be formed such that it can be overcome without destruction against a resilient blocking force. Furthermore, the actuating means can in the initial state of the injection device be blocked rotationally as well as axially, i.e., by a rotational and an axial block. In such embodiments at least one of the two blocks is formed to be releasable against a resilient blocking force. The other one of the two blocks can also be formed to be releasable against a resilient blocking force or can be formed such that it can be overcome only by destruction of at least one blocking element involved in the non-releasable block.

The second aspect of the invention is advantageous in particular with respect to injection devices which allow for dosage selection. By providing an actuating means in addition to the casing and the plunger rod a priming operation, dosage selection and dosage delivery can be accomplished by the patient smoothly and safely. It is for example no longer required that the plunger rod can also rotate about the device axis. Rather, the movability of the plunger rod can be restricted to an axial movability. Relative rotational movements would cause at least a certain amount of friction between the front end of the plunger rod and the backside of the plunger and might even result in turning the plunger. The drive coupling can be established between the actuating means and the plunger rod. The actuating means and the plunger rod can be coupled directly, one with the other, or indirectly via one or more additional coupling members, as also mentioned above. The functions of the casing can be restricted to supporting the actuating means rotatably and axially or to guiding the plunger rod axially. This includes embodiments in which the casing is supporting the actuating means rotatably and axially but is not guiding the plunger rod axially, furthermore embodiments in which the casing is guiding the plunger rod axially but does not support the actuating means rotatably and axially, and does also include embodiments in which the casing is supporting the actuating means rotatably and axially and is guiding the plunger rod axially.

The coupling can be established in a hollow space of the actuating means. The plunger rod may e.g., protrude axially into the actuating means. Alternatively, the coupling can be established in a hollow space of the plunger rod. In such embodiments, the actuating means can axially protrude into the plunger rod.

In an injection device which comprises a control track and an entrainment track, as under the first aspect, and which furthermore provides for dosage selection, the coupling of the actuating means and the plunger rod can be such that priming as well as dosage selection can be performed by turning the actuating means, wherein priming and dosage selection is sequenced by the coupling, i.e., in the engagement of the control member or the control member and the optional additional entrainment member on the one and the control track and the entrainment track on the other hand. In such embodiments, priming can in particular be accomplished by the engagement of the control member and the control track, and dosage selection by the engagement of the control member or the additional entrainment member, if the latter is present, and the entrainment track.

Advantageous features are also described in the following embodiments of the second aspect of the invention and the combinations of those embodiments (the reference signs corresponding to those used in FIGS. 22 to 49):

H. An injection device, comprising
a) a casing (1, 8; 20, 20*b*, 21; 1, 16) which accommodates or forms a reservoir (22) for a liquid drug;
b) a plunger rod (4; 40) which can move relative to the casing (1, 8; 20, 20*b*, 21; 1, 16) axially in a forward direction to deliver the drug;
c) an actuating means (10; 30, 50) which can move in the forward direction relative to the casing (1, 8; 20, 20*b*, 21; 1, 16) and rotate relative to the casing (1, 8; 20, 20*b*, 21; 1, 16) and the plunger rod (4; 40);
d) a curved control track (11; 31) having an inclination ($\alpha$) greater than 0° and smaller than 90° with respect to the forward direction;
e) a curved entrainment track (12; 52) having an inclination ($\beta$) greater than 0° and at most 90° with respect to the forward direction;
f) and a control member (5; 45) which drivingly engages the control track (11; 31) to form a cam drive (5, 11; 45, 31) which couples the actuating means (10; 30, 50) to the plunger rod (4; 40) such that a rotational movement of the actuating means (10; 30, 50) forces the plunger rod (4; 40) into the forward direction;
g) optionally an entrainment member (46);
h) wherein either the control member (5; 45) or the entrainment member (46), if present, can be brought into engagement with or engages the entrainment track (12; 52) such that the actuating means (10; 30, 50), when moving in the forward direction, carries the plunger rod (4; 40) along in the forward direction by means of the engagement with the entrainment track (12; 52).

i) The injection device according to embodiment H, wherein the control member (5; 45) engages the control track (11; 31) at an initial track location when the actuating means (10; 30, 50) is in an initial rotational position relative to the casing (1, 8; 20, 20*b*, 21; 1, 16) and travels along the control track (11; 31) towards an end of the control track (11; 31) upon rotation of the actuating means (10; 30, 50) in a first rotational direction, and wherein movement of the actuating means (10; 30, 50) in the forward direction is prevented when the actuating means (10; 30, 50) is in the initial rotational position.

J. The injection device according to any one of embodiments H and I, wherein either the control member (5; 45) or at least one of the tracks (11, 12; 31, 52) is arranged non-rotatably relative to the actuating means (10; 30, 50) and the other one of the control member (5; 45) and the at least one of the tracks (11, 12; 31, 52) is arranged non-rotatably relative to the plunger rod (4; 40).

K. The injection device according to any one of embodiments H to J, wherein either the control member (5; 45) or at least one of the tracks (11, 12; 31, 52) is arranged axially fixed relative to the actuating means (10; 30, 50) and the other one of the control member (5; 45) and the at least one of the tracks (11, 12; 31, 52) is arranged axially fixed relative to the plunger rod (4; 40).

L. The injection device according to any one of embodiments H to K, wherein either the control member (5; 45) or at least one of the tracks (11, 12; 31, 52) is formed at the actuating means (10; 30, 50) in one piece with the actuating means (10; 30, 50).

M. The injection device according to any one of embodiments H to L, wherein either the control member (5; 45) or at least one of the tracks (11, 12; 31, 52) is formed at the plunger rod (4; 40) in one piece with the plunger rod (4; 40).

N. The injection device according to any one of embodiments H to M, wherein the inclination (α) of the control track (11) is smaller than the inclination (β) of the entrainment track (12).

O. The injection device according to any one of embodiments H to N, wherein the entrainment track (12; 52) has an inclination (β) of 90° with respect to the forward direction, at least over a portion of its course, such that the actuating means (10; 50) can be rotated without causing a forward movement of the plunger rod (4) when either the control member (5) or the entrainment member (46), if present, engages the entrainment track (12; 52).

P. The injection device according to any one of embodiments H to O, wherein the actuating means (10) is coupled to the plunger rod (4) by means of the cam drive (5, 11) in which the control member (5) engages a combined track (11, 12) which comprises the control track (11) as a first track section and the entrainment track (12) as a second track section.

Q. The injection device according to embodiment P, wherein the combined track (11, 12) is continuous from an end of the control track (11) that is distant from the entrainment track (12) up to an end of the entrainment track (12) that is distant from the control track (11), the inclination increasing monotonously from the inclination (α) of the control track (11) to the inclination (β) of the entrainment track (12).

R. The injection device according to any one of embodiments H to Q, wherein a dosing means (9, 13; 33, 43) is provided which comprises a dosing member (10; 30) and a dosing counter member (1, 8; 40; 1, 16), and wherein the dosing member (10; 30) can perform a rotational dosing movement relative to the dosing counter member (1, 8; 40; 1, 16) to select a drug dosage to be delivered by moving the plunger rod (4; 40) in the forward direction.

S. The injection device according to embodiment H to R, wherein the actuating means (30, 50) comprises the dosing member (30) and an actuating member (50), and the dosing member (30) is coupled to the actuating member (50) by means of an axial guide (34, 54) which allows for an axial movement of the actuating member (50) relative to the dosing member (30) and prevents a rotational movement of the actuating member (50) relative to the dosing member (30).

T. The injection device according to embodiment S, wherein the control track (31) is arranged non-rotatable and axially fixed relative to the dosing member (30), the entrainment track (52) is arranged non-rotatable and axially fixed relative to the actuating member (50), the entrainment member (46) engages the entrainment track (52), and the entrainment track (52) is formed such that the entrainment member (46) engages the entrainment track (52) while the control member (45) engages the control track (31).

U. The injection device according to any one of embodiments H to T, wherein the control member (5; 45) loses its driving engagement with the control track (11; 31) upon rotation of the actuating means (10; 30, 50) in a first rotational direction whereby the actuating means (10; 50) is rotationally decoupled from the plunger rod (4; 40) such that a dose of the drug can be selected by rotating the actuating means (10; 30, 50) further in the first direction without causing a forward movement of the plunger rod (4; 40).

V. An injection device, comprising
a) a casing (1, 8; 20, 20b, 21; 1, 16) which accommodates or forms a reservoir (22) for a liquid drug;
b) a plunger rod (4; 40) which can move relative to the casing (1, 8; 20, 20b, 21; 1, 16) in a forward direction of a device axis (L) to deliver the drug;
c) an actuating means (10; 30, 50) which can rotate relative to the casing (1, 8; 20, 20b, 21; 1, 16) and the plunger rod (4; 40) to select a drug dosage to be delivered and which can move in the forward direction relative to the casing (1, 8; 20, 20b, 21; 1, 16) for delivering the selected dosage;
d) an entrainment track (12; 52) curved about the device axis (L);
e) and an entrainment member (5; 46) which drivingly engages the entrainment track (12; 46) to form a drive connection (5, 12; 46, 52) which couples the actuating means (10; 30, 50) to the plunger rod (4; 40) such that the actuating means (10; 30, 50), when moving in the forward direction, carries the plunger rod (4; 40) along in the forward direction by means of the engagement with the entrainment track (12; 52);
f) wherein the engagement of the entrainment member (5; 46) and the entrainment track (12; 46) allows for the rotational movement of the actuating means (10; 30, 50) relative to the plunger rod (4; 40).

W. The injection device according to any one of embodiments H to V, wherein the engagement with the entrainment track (12; 52) allows for rotation of the actuating means (10; 30, 50) without a forward movement of the plunger rod (4; 40).

X. The injection device according to embodiment V or W, further comprising
  I. a curved control track (11; 31) having an inclination (α) greater than 0° and smaller than 90° with respect to the forward direction;
  II. and a control member (5; 45) which drivingly engages the control track (11; 31) to form a cam drive (5, 11; 45, 31) which couples the actuating means (10; 30, 50) to the plunger rod (4; 40) such that a rotational movement of the actuating means (10; 30, 50) forces the plunger rod (4; 40) into the forward direction;
  III. wherein the control member (5; 45) is either provided by the entrainment member (5) or in addition to the entrainment member (45).

Y. The injection device according to any one of embodiments H to X, wherein the plunger rod (4; 45) is guided axially such that it cannot rotate relative to the casing (1, 8; 20, 20b, 21; 1, 16).

Z. The injection device according to any one of embodiments H to Y, wherein a dosing means (9, 13; 33, 43) is provided which comprises a dosing member (10; 30) and a dosing counter member (1, 8; 40; 1, 16), and wherein the dosing member (10; 30) can perform a rotational dosing movement relative to the dosing counter member (1, 8; 40; 1, 16) to select a drug dosage to be delivered by moving the plunger rod (4; 40) in the forward direction.

AA. The injection device according to embodiment H to Z, wherein the actuating means (10; 30, 50) is the dosing member (10) or comprises the dosing member (30) and furthermore an actuating member (50) which is arranged to be movable axially relative to the casing (20, 20b, 21).

BB. The injection device according to embodiments Z or AA, wherein one of the dosing member (10) and the dosing counter member (1, 8; 40; 1, 16) is provided with a first dosing element (13; 43) and the other one of the dosing member (10) and the dosing counter member (1, 8; 40; 1, 16) is provided with second dosing elements (9$_i$; 33) disposed at different circumferential positions, and wherein the dosage is selected by matching the circumferential position of the first dosing element (13; 43) with the circumferential position of one of the second dosing elements (9$_i$; 33).

CC. The injection device according to any one of embodiments H to BB, wherein either the entrainment member (5; 46) or at least one of the tracks (11, 12; 31, 52) is arranged non-rotatably relative to the actuating means (10; 30, 50) and the other one of the entrainment member (5; 46) and the at least one of the tracks (11, 12; 31, 52) is arranged non-rotatably relative to the plunger rod (4; 40).

DD. The injection device according to any one of embodiments H to CC, wherein either the entrainment member (5; 46) or at least one of the tracks (11, 12; 31, 52) is arranged axially fixed relative to the actuating means (10; 30, 50) and the other one of the entrainment member (5; 46) and the at least one of the tracks (11, 12; 31, 52) is arranged axially fixed relative to the plunger rod (4; 40).

EE. The injection device according to any one of embodiments H to DD, wherein either the entrainment member (5; 46) or at least one of the tracks (11, 12; 31, 52) is formed at the actuating means (10; 30, 50) in one piece with the actuating means (10; 30, 50).

FF. The injection device according to any one of embodiments H to EE, wherein either the entrainment member (5; 46) or at least one of the tracks (11, 12; 31, 52) is formed at the plunger rod (4; 40) in one piece with the plunger rod (4; 40).

BRIEF DESCRIPTION OF THE DRAWINGS

FIGS. 2a1, 2a2, 2b1, 2b2, 2c1 and 2c2 show the steps of assembling the inventive injection device;

FIGS. 3a and 3b show the inventive injection device in an initial state;

FIGS. 4a and 4b show a state of the injection device after removing the needle cover;

FIGS. 5a and 5b show a step of priming the inventive injection device;

FIGS. 5c1, 5c1', 5c2, 5c2', 5c3, 5c3', 5c4 and 5c4' show a sequence of injection with the injection device and withdrawing the injection device;

FIGS. 15, 16 and 17 show the rotational blocking means and the tensioning means;

FIG. 18 shows the functionality of the dose blocking means;

FIGS. 19a, 19b and 19c show the needle shield blocking means;

FIGS. 21a1 to 21f2 show further embodiments of a needle protection means;

FIG. 26 is the injection device of the first example in a side-view;

FIG. 27 is the section A-A of FIG. 26 with the injection device in the initial state;

FIG. 28 is the section A-A of FIG. 26 with the injection device after initial priming;

FIG. 30 is the injection device of the second example in an axial view;

FIG. 31 is the section A-A of FIG. 30 with the injection device in an initial state;

FIG. 32 is the section B-B of FIG. 30 with the injection device in the initial state;

FIG. 33 is the injection device of the second example of the preferred embodiment after initial priming;

FIG. 34 is the injection device of the second example after completion of priming;

FIG. 35 is the injection device of the second example after setting a small dose;

FIG. 36 is the injection device of the second example after injection;

FIG. 37 is a plunger rod and a dosing member of the second example;

FIG. 38 is an actuating means of the injection device of the second example;

FIG. 39 is a proximal casing portion of the injection device of the second example;

FIG. 40 is view E of FIG. 39;

FIG. 41 is section E-E of FIG. 39 with the dosing member in a first rotational position;

FIG. 42 is section E-E of FIG. 39 with the dosing member in a second rotational position;

FIG. 45 is an injection device of a fourth example of the preferred embodiment in a first longitudinal section;

FIG. 46 is the injection device of the fourth example in a second longitudinal section;

FIG. 47 is a plunger rod and an actuating means of the fourth example;

FIG. 48 is a schematic illustration of a dosing means of the fourth example; and FIG. 49 is a schematic illustration of a modified dosing means of the fourth example.

DETAILED DESCRIPTION

FIGS. 2a1 to 5c4' comprise pairs of axial sectional views differing in perspective by 90° of rotation of the injection device around its longitudinal axis.

Throughout the figures, the same reference signs denote the same script role features of the shown embodiment of the inventive injection device.

Figure 1:
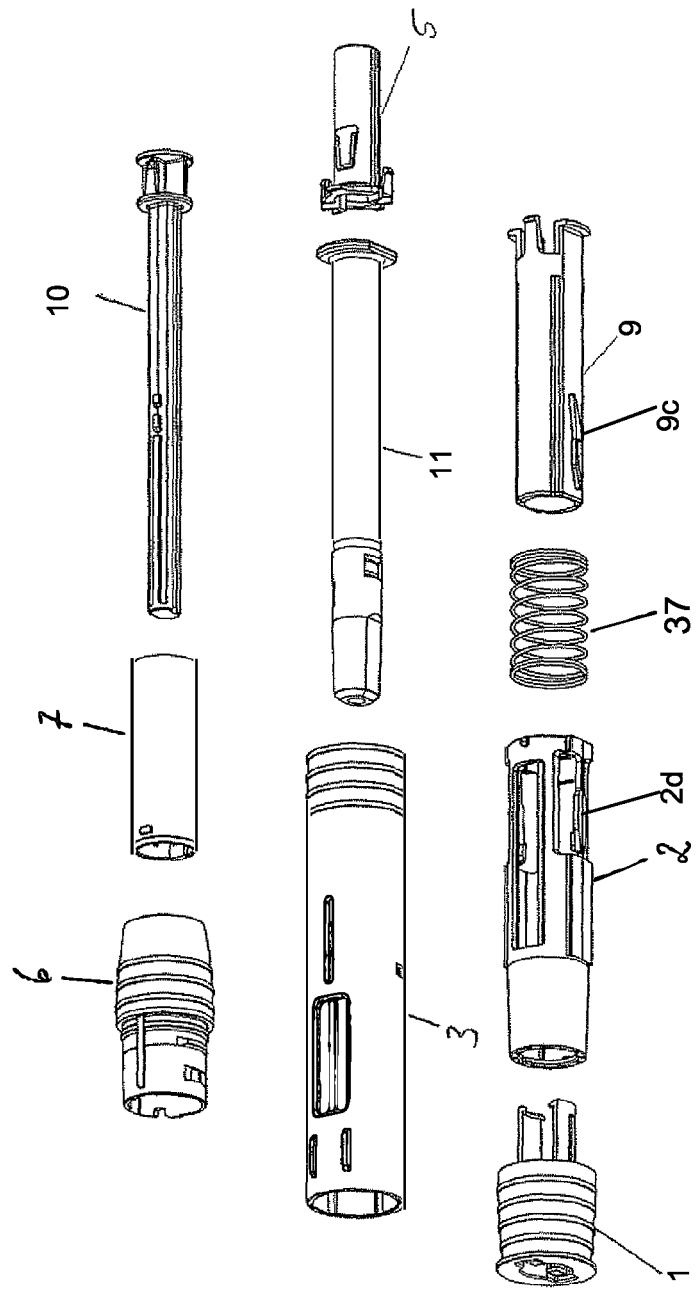
FIG. 1 shows the individual parts of the inventive injection device.
Figure 6A:
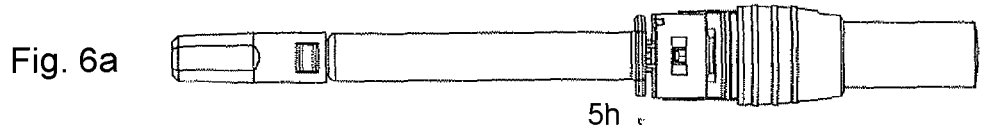
FIGS. 6a to 6d and 7 show the inventive injection device before coupling the first and the second casing parts to each other.
Figure 6B:
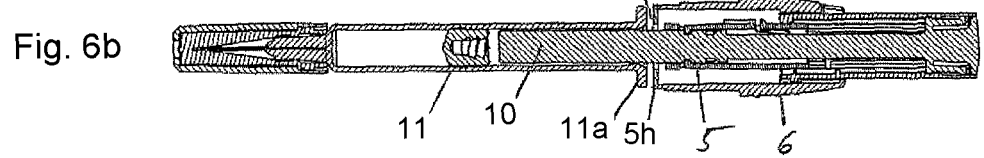
Figure 6C:
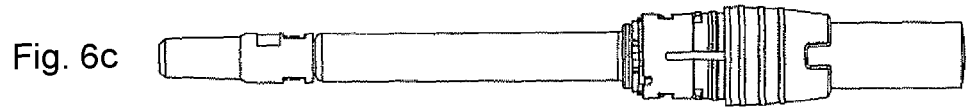
Figure 6D:
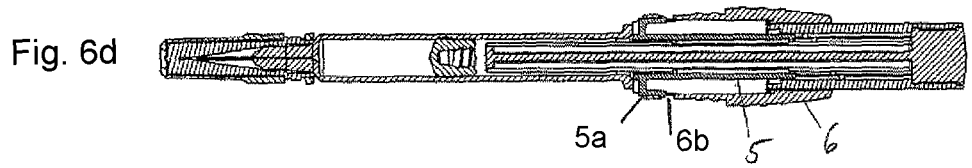

FIG. 1 gives an overview of the constituents of the inventive injection device according to a preferred embodiment. The injection device comprises a needle protection means embodied by a front cap 1, a sleeve-shaped needle shield 2, a first casing part comprising a housing 3 and a syringe holder 9, a reservoir embodied by a syringe 11, a plunger rod 10, a second casing part comprising the plunger rod guiding means 5 and an outer casing part embodied by a proximal end cap 6, and a dosing means embodied by a dosing sleeve 7. The needle shield biasing means is embodied by a spiral spring 37.

FIGS. 2a1 to 2c2 show the process of assembling the inventive injection device which is delivered to a user for example in the state shown in FIGS. 2a1 and 2a2 in which the front assembly comprising in particular the first casing part and further particularly the needle protection means 1, needle shield 2, housing 3, syringe holder 9, and spiral spring 37 is not coupled to the rear assembly comprising in particular the second casing part and further particularly the end cap 6, plunger rod guiding means 5, plunger rod 10 and dosing sleeve 7. In the state shown in FIGS. 2a1 and 2a2, in particular the first casing part comprising the housing 3 and syringe holder 9 can be engaged to the second casing part comprising the plunger rod guiding means 5 and the end cap 6 in a not proper engagement. It means that after coupling the second casing part to the first casing part the housing 3 and the end cap 6 can be detached from one another in order to insert a syringe into the housing. In the next step shown in FIGS. 2b1 and 2b2, the first casing part is detached from the second casing part and a syringe 11 is inserted into the front assembly so as to be held by the syringe holder 9 as shown in FIGS. 2c1 and 2c2. The rear assembly can then be coupled to the front assembly by pushing the distal section of the end cap 6 into the proximal section of the housing 3 when the longer casing rotation blocking rib 8b lies in the shorter rotating blocking notch 8d (more particularly described below).

The state of the injection device shown in FIGS. 2c1 and 2c2 is also represented in FIGS. 3a and 3b. FIGS. 3a and 3b show axial sections of the inventive injection device in two planes which are perpendicular to each other. The needle protection means 1 comprises a flexible snap member 1a which is configured to abut a holding rib 2a of the needle shield 2, the holding rib 2a being positioned at the distal end of the needle shield 2 on its interior surface preferably around its whole circumference so as to prevent the needle protection means is from falling out of the distal end of the injection device. The snap member 1a can be deflected into a radially inward direction by a manual force which is applied onto the needle protection means 1 in a distal direction for pulling the needle protection means 1 off the needle shield 2. To this end, the snap member 1a comprises a tapered distal end surface which may slide along the holding rib 2a. The needle protection means 1 is not rotatable relative to the needle shield 2 in the configuration shown in FIGS. 3a and 3b. For example, the inner boot comprises an axial rib on its outer surface which co-operates with an axial notch on an inner surface of the needle shield in order to prevent rotation of the two relative to one another. The needle shield 2 also comprises a proximal holding projection 2b with which it abuts the housing 3 in a distal direction and preferably engages a recess in the interior surface of the housing 3 so as to be blocked against a rotation relative to the housing 3. The spiral spring 37 abuts the housing 3 in a proximal direction and the needle shield 2 in a distal direction. The housing 3 accommodates a syringe holder 9 comprising an engagement member 9b at its proximal end which engage a holding ring 3e on the interior surface of the housing 3 so that the syringe holder 9 may not be detached from the housing 3 and in particular cannot move relative to the housing in an axial direction. The syringe holder 9 holds a syringe 11 comprising a syringe flange 11a and a piston 11b which is movable in the interior of the syringe 11 in an axial direction so as to exert pressure onto a medical fluid accommodated in the syringe. The piston 11b is moved by the plunger rod 10 if the plunger rod 10 is moved in a distal direction (for example by exerting manual pressure on an activating means embodied by the operating knob 10e disposed at the proximal end of the plunger rod 10). The plunger rod 10 is guided by a plunger rod guiding means 5 which is held by tensioning it between the syringe flange 11a and the end cap 6. The coupling means for coupling the first casing part and the second casing part to one another comprises by an engagement means comprising coupling ribs 6c, 6c' and a holding means comprising coupling notches 3g, 3g'. The coupling ribs 6c, 6c' and the coupling notches 3g, 3g' run in a circumferential direction. The end cap 6 comprises two coupling ribs 6c, 6c' on an outer surface of its distal section which are pushed into each a corresponding on of the two coupling notches 3g, 3g' on an interior surface of the housing 3 at its proximal end. Rotation of the end cap 6 relative to the housing 3 after coupling them to one another is prevented by a casing rotation blocking means comprising axial casing rotation blocking ribs 8a, 8b on an outer surface of the end cap 6 which are configured to co-operate with axial casing rotation blocking notches 8c, 8d on an interior surface of the housing 3. The casing rotation blocking ribs 8a, 8b have different lengths which are designed to correspond to the length of the corresponding one of the casing rotation blocking notches 8c, 8d such that the casing rotation blocking ribs 8a, 8b can be fully accommodated in the respectively corresponding rotation blocking notch 8c, 8d after coupling the end cap 6 to the housing 3. In a delivery state of the injection device, the longer one (8b) of the casing rotation blocking ribs lies in the shorter one (8c) of the casing rotation blocking notches, and the coupling rib 6c lying further in a distal direction lies in the coupling notch 3g' lying further in the proximal direction. In that configuration, the housing 3 and the end cap 6 are not properly coupled to each other and can be detached from one another in order to insert the syringe 11 into the housing 3. In FIGS. 3a and 3b the first casing part and second casing part are axially and rotationally fixed to each other since the longer casing rotation blocking rib 8b lies in the longer rotation blocking notch 8d and the coupling rib 6c' of the end cap is coupled to the coupling notch 3g' of the housing 3.

The plunger rod guiding means 5 comprises a holding means embodied by holding arms 5g which lie in recesses 6b in the interior surface of the end cap 6. The plunger rod guiding means 5 is tensioned by abutment of the spacing means 5i of the plunger rod guiding means 5 on the syringe flange 11a, engagement of the holding arms 5g into the recesses 6b and biasing the elastic tensioning members 5h which are disposed in a radial direction at the distal end of the plunger rod guiding means 5. The elastic tensioning members 5h are biased because they are pressed by the distal circumference of the outer casing part 6 into the distal direction.

The axial blocking means which is configured to block movement of the plunger rod 10 relative to the casing 3 is embodied by elastic abutment members 5*b* on the plunger rod guiding means 5 which comprise abutment surfaces on their distal side which run in a substantially radial direction. Furthermore, the axial blocking means comprises blocking wings 10*g* which have a tapered distal surface for deflecting the elastic abutment members 5*b* in a radially outward direction during this movement of the plunger rod 10 in a distal direction. The blocking wings 10*g* furthermore comprise abutment surfaces on their proximal side which run in a substantially radial direction so as to abut the elastic abutment members 5*b* from the distal side after even further distal movement of the plunger rod 10. By this abutment, the plunger rod 10 is prevented from moving in the proximal direction. The plunger rod furthermore comprises rotational blocking surfaces 10*b* which are moveable on guide rails 5*c* of plunger rod guiding means and abut the guide rails 5*c* in a rotational direction. The guide rails 5*c* and the rotational blocking surfaces 10*b* together form the above-described rotational blocking means which prevents the plunger rod 10 from being rotated relative to the plunger rod guiding means 5 and the casing 3. The dosing sleeve 7 surrounds the plunger rod 10 at its proximal end and in particular also surrounds the operating knob 10*e*. The dosing sleeve 7 comprises an inner circumferential groove 7*c* in which a circumferential rib 10*c* of the plunger rod 10 lies so as to prevent movement of the dosing sleeve 7 in an axial direction relative to the plunger rod 10.

FIGS. 2*a*2, 3*a*, 4*a* and 4*b* show the functionality of the removing means embodied by axial hooks 1*b* on the proximal end of an inner boot 1*c* of the needle protection means 1. The needle protection means 1 is pulled off from the needle shield 2 in a distal direction, whereby the snap member 1*a* overcome the abutting resistance provided by the holding rib 2*a*. The front cap 1 can therefore be separated from the needle shield 2. The axial hooks 1*b* engage behind the proximal circumference of a discharge means cover embodied by a needle cover 12. The axial hooks 1*b* may have a beveled proximal surface which allows insertion of the syringe 11 fitted with the needle cover 12 into the inner boot 1*c* in an axial direction when inserting the syringe 11 into the injection device as shown in FIGS. 2*b* and 2*c*. In particular, the axial hooks 1*b* can be deflected in a radially outward direction during such a movement and, when the syringe 11 and the needle cover 12 are pushed further distally, can snap behind the proximal circumference of the needle cover 12. When pulling the needle protection means 1 off the needle shield 2, the axial hooks 1*b* then serve to take the needle cover 12 along with the needle protection means 1. Thereby, the front cap 1 and the needle cover 12 can be removed in a single operating step. Furthermore, this feature of the front cap 1 also reduces the user's risk of injury since the user does not need to manipulate the needle cover 12 directly which might lead to accidently pricking himself on the tip of the (hollow) needle 11*c* which embodies the discharge means.

FIGS. 5*a* and 5*b* show the configuration of the injection device after priming. In this configuration, the plunger rod 10, the piston 11*b* and the dosing sleeve 7 have been moved in a distal direction relative to the casing by a predetermined distance (also called priming distance) corresponding to the distance between a first axial blocking notch 10*a* and a second axial blocking notch 10*d* formed in the plunger rod 10 which are configured to accommodate the abutment members 5*b* disposed at diametrically opposite sides of the plunger rod guiding means 5. The abutment members 5*b*, the axial blocking notches 10*a*, 10*d* and the axial blocking wings 10*g* together form the axial blocking means. The axial abutment members 5*b* are configured to be moved in a radially outward direction by a force exerted by the tapered distal surfaces of the blocking wings 10*g* if the plunger rod is moved in a distal direction relative to the casing. As noted, the piston 11*b* is also moved by a corresponding distance into the distal direction, thereby decreasing the volume available in the syringe 11 for accommodating the medical fluid and air. During priming, the injection device is preferably held with its distal end pointing upward in a vertical direction so that during the priming movement of the plunger rod 10 and the piston 11*b* in a distal direction relative to the casing, the air will be present at the distal end of the syringe volume of the syringe 11 and will then be discharged from the syringe during the priming stroke. The priming stroke in particular involves the distal movement of the plunger rod 10 and the piston 11*b* by the aforementioned predetermined distance. By a predetermined distance which is suitable to de-air the syringe 11. After the priming movement, the proximal surface of a blocking wing 10*g* which runs in a substantially radially direction abuts the distal surface of the abutment 5*b* which also runs in a substantially radial direction. Due to this abutment, it will not be possible to move the abutment member 5*b* in a distally outward direction, rather a proximal movement of the plunger rod 10 relative to the casing will be prevented by the abutment. FIG. 5*b* also shows that, compared to the configuration shown in for example FIG. 4*b*, the dosing sleeve 7 was moved in the distal direction by the priming distance. The plunger rod guiding means 5 remains at a fixed position relative to the casing (in particular relative to the housing 3 and the end cap 6) during the priming stroke. The dosing sleeve 7 then moves in a distal direction by the priming distance relative to the plunger rod guiding means 5 during the priming stroke. The deflecting means 7*d* of the dosing control means then lies over the rotational limitation means 5*e*. In particular, the deflecting means 7*d* abuts the rotation limitation means 5*e* in a radially inward direction and deflects the rotation limitation means 5*e* in the radially inward direction. The deflecting means 7*d* takes the form of a projection on an inner surface of the dosing sleeve 7, and the rotation limitation means 5*e* is embodied by a flexible tongue having a tapered proximal surface so that the deflecting means 7*d* can be pushed in a distal direction onto the rotation limitation means 5*e* at least at the end of the priming stroke. In particular, the dosing sleeve 7, the plunger rod 10, the position of the blocking wings 10*g* and the axial blocking notches 10*a*, 10*d* on the plunger rod 10 and the rotation limitation means 5*e* on the plunger rod guiding means 5 are dimensioned such that the distance which the plunger rod 10 travels during the priming stroke corresponds to the distance which the deflecting means 7*d* has to travel in order to move from its position shown in FIG. 4*b* to its position shown in FIG. 5*b*, in particular in order to deflect the rotation limitation means 5*e*.

FIGS. 5*c*1 to 5*c*4' shows a sequence of operation of the injection device in pairs of sectional views representing perspectives from directions perpendicular to one another. FIGS. 5*c*1 and 5*c*1' show the state of the injection device after the first casing part and the second casing part have been coupled to one another and after the injection device has been primed. Furthermore, the needle 11*c* is extending distally out from the needle shield 2 because the injection device has been pressed onto the injection location such that the needle is inserted into the injection location and the needle shield 2 is pushed proximally into its retracted position inside the housing. The subsequent operational step is illustrated by FIGS. 5*c*2 and 5*c*2'. In these figures, the needle shield still is in its retracted position and the piston 11*b* is in its most a distal position, i.e., the medical fluid contained in the syringe 11 has been (completely) discharged. FIGS. 5*c*3 to 5*c*4' (i.e., 5*c*3, 5*c*3', 5*c*4 and 5*c*4') show the state of the injection device after lifting it off from the injection location so that the needle shield 2 extends into its forward position in order to surround the needle 11*c*. In this state, the needle shield 2 is, as described herein, prevented from being pushed in the proximal direction again.

In FIGS. 6*a*, 6*b*, 6*c*, 6*d* and 7, the functionality of the tensioning means comprising an elastic member 5*h* of the plunger rod guiding means 5 is explained. It is to be noted that FIGS. 6*a* to 9 do not show the front assembly. However, it is assumed that the syringe 11 has been inserted into the front assembly and that the rear assembly has not yet been coupled to the front assembly. In this configuration, the elastic members of the tensioning means 5*g* run in a substantially radial direction. The elastic members 5*h* are, as also shown in FIG. 16, formed as part of the plunger rod guiding means 5 and are disposed on a circumferential ring substantially at the distal end of the plunger rod guiding means 5 and proximal of the axial protrusion 5*i* which constitute the spacing means for spacing the plunger rod guiding means from the syringe flange 11*a*. In the configuration shown in FIGS. 6 and 7, the holding arms 5*g* lie in the recesses 6*b* of the end cap 6. In particular, engagement members formed at the ends of the holding arms 5*g* abut the distal limitation of the recesses 6*b*.

Figure 7:
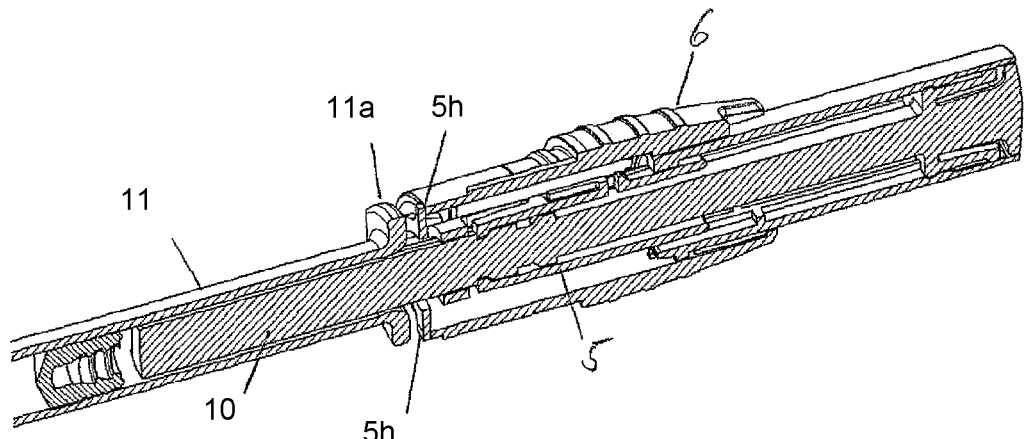
Figure 8A:
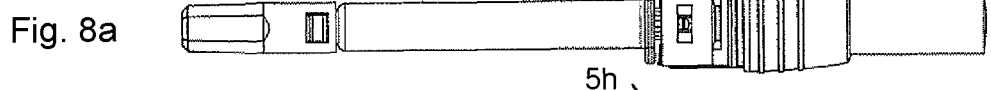
FIGS. 8a to 8d and 9 show the inventive injection device after coupling the first and second casing parts to each other.
Figure 8B:
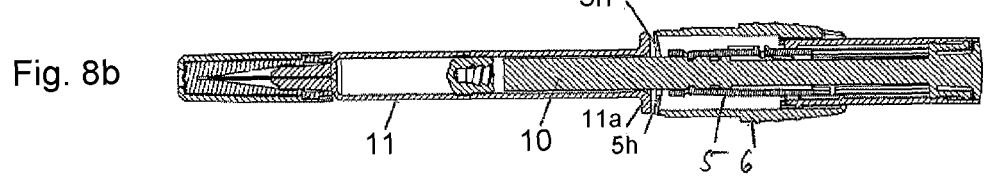
Figure 8C:
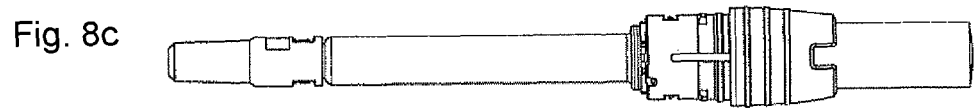
Figure 8D:
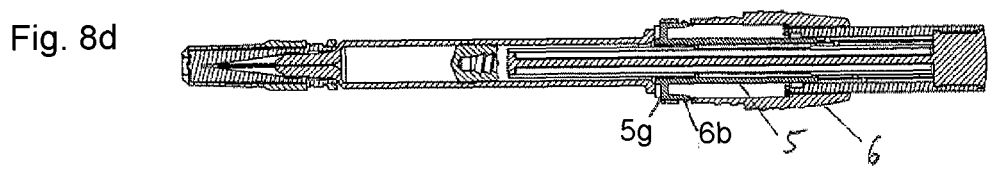
Figure 9:
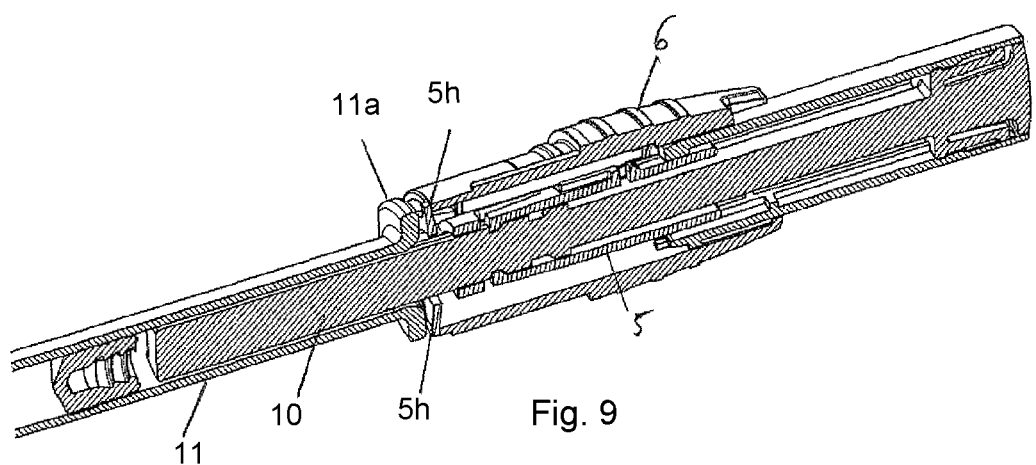

FIGS. 8*a*, 8*b*, 8*c*, 8*d* and 9 show the features also shown in FIGS. 6 and 7 in the configuration in which the reassembly has been coupled to the front assembly. The holding arms 5*g* now abut the proximal limitations of the recesses 6*b* in the end cap 6. By interaction of the threads formed on the end cap 6 and the housing 3, the syringe flange 11*a*, the axial protrusions 5*i* (not shown in FIGS. 6 to 9 but visible in FIG. 16) and the distal end circumference of the end cap 6, the tensioning means 5*h* are deformed and biased. The bases of the elastic members of the tensioning means 5*h* are pushed in a proximal direction compared to the configuration shown in FIGS. 6 and 7, while their outer radial ends abut the distal circumference of the end cap 6 and substantially remain in the position which they had in the configuration shown in FIGS. 6 and 7. Thereby, the plunger rod guiding means 5 is tensioned relative to the casing, in particular relative to the end cap 6, and by the abutment between the holding arms 5*g* and the recesses 6*b* remains in an axially fixed position relative to the end cap 6.

Figure 10A:
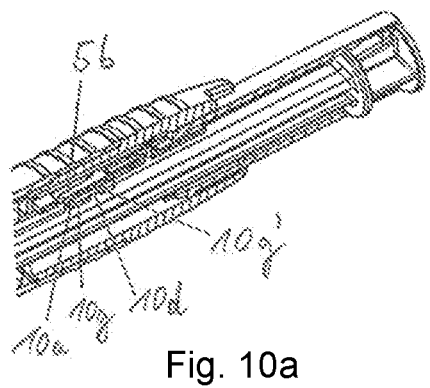
FIGS. 10a and 10b show the functionality of the axial blocking means.
Figure 10B:
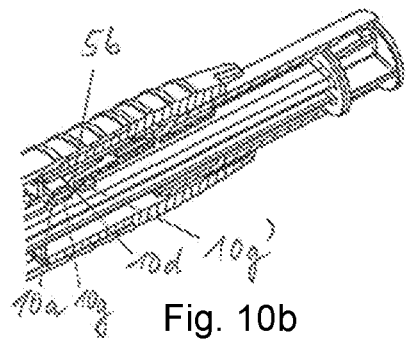

FIG. 10*a* and FIG. 10*b* show a further detail of how the axial blocking means functions. Before priming, the abutment member lies in the first axial blocking notch 10*a* and distally of a first blocking wing 10*g* (compare FIG. 10*a*). FIG. 10*b* shows the configuration after priming, in which the abutment member 5*b* lies in the second axial blocking notch 10*b* at a position which is proximal relative to the first blocking wing 10*g* and distal relative to a second axial blocking wing 10*g*'.

Figure 11A:
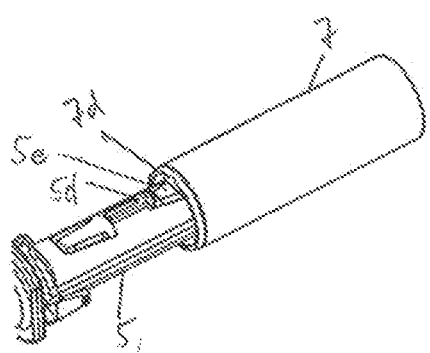
FIGS. 11a, 11b, 12a and 12b show the functionality of the dosing control means.

FIG. 11*a* shows the position of the deflecting means 7*d* relative to the rotation limitation means 5*e* before priming. The deflecting means 7*d* lies radially further outward relative to the rotation limitation means 5*e* and at a position proximal of the rotation limitation means 5*e*.

Figure 11B:
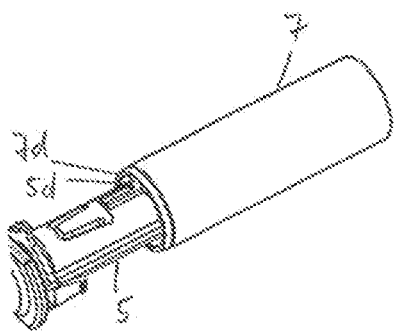

FIG. 11*b* shows the situation at the end of the priming stroke, when the deflecting means 7*d* lies radially further outward than the rotation limitation means 5*e* and at substantially the same axial position as the rotation limitation means 5*e*. In this situation, the deflecting means 7*d* depresses the rotation limitation means 5*e* in a radially inward direction. Furthermore, the deflecting means 7*d* abuts the distal projection 5*d* of the dose blocking means in a distal direction.

Figure 12A:
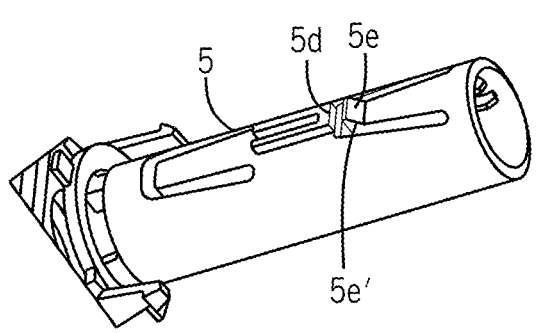
Figure 12B:
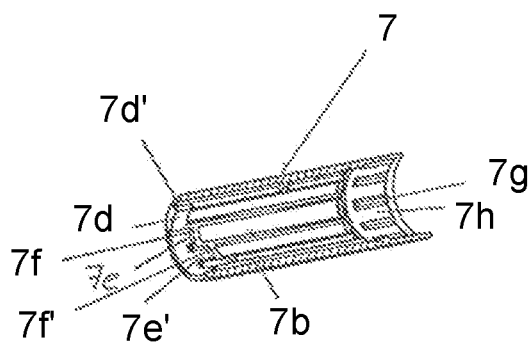

FIG. 12*a* shows a further perspective of the plunger rod guiding means 5, the rotation limitation means 5*e* and the distal projection 5*d* of the dose blocking means. FIG. 12*b* shows a perspective axial section of the dosing sleeve 7. A dose to be injected is defined by rotating the dosing sleeve 7 relative to the casing, in particular relative to the plunger rod guiding means so that the rotation limitation means is axially aligned with a dose defining groove 7*e*, 7*e*'. The plunger rod 10 and the dosing sleeve 7 can then be moved in the distal direction so that the projection formed on the distal end of the rotation limitation means 5*e* can move in an axial direction relative to the dosing sleeve 7 within the selected dose defining groove 7*e*, 7*e*'. The plunger rod is therefore able to move by a distance which corresponds to the distance between the distal end surface of the deflecting means 7*d* and the proximal end of the respective dose defining groove 7*e*, 7*e*'. Since the amount by which the plunger rod 10 is allowed to travel in the distal direction governs the amount of medical fluid which is discharged, the length of the selected dose defining groove 7*e*, 7*e*' governs the amount of medical fluid which can be discharged, i.e., the dose to be injected. In particular, the plunger rod 10 can be moved in the distal direction relative to the casing until the projection 7*f*, 7*f* located at the proximal end of the selected dose defining groove 7*e*, 7*e*' abuts the distal projection 5*d* of the dose blocking means. Then, further distal movement of the plunger rod 10 is possible and the projection at the distal end of the rotation limitation means 5*e* snaps in a radially outward direction such that it abuts the respective projection 7*f*, 7*f* at its proximal side and therefore serves as a part of the dose locking means. It then is no longer possible to move the dosing sleeve 7 back in the proximal direction relative to the casing. Thus, the plunger rod 10 cannot be moved back in the proximal direction once the selected dose to be injected has been completely injected and re-using the inventive injection device is therefore prevented. The inventive injection device therefore preferably constitutes a single-use injection device.

Figure 13:
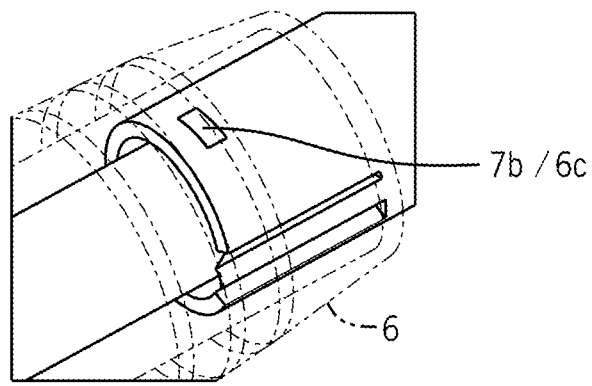
FIGS. 13 and 14 show the functionality of the rotation prevention means.
Figure 14:
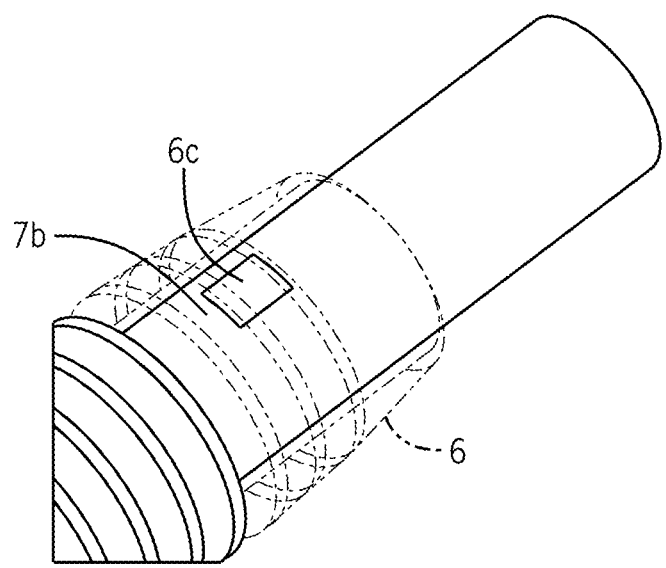

The dosing sleeve 7 has on its interior surface axial dose defining grooves 7*e*, 7*e*' which at their proximal ends comprise circumferential projections and 7*f*, 7*f* which belong to the dose locking means. Furthermore, the dosing sleeve 7 comprises the deflecting means 7*d*, the axial surfaces 7*d*' of which co-operate with the axial surfaces 5*e*' of the rotation limitation means 5*e* in order to function as part of the dosing control means which prevents a rotation of the dosing sleeve back into the position which the dosing sleeve had (for example the position shown in FIG. 11*b*) in particular relative to the casing (more particularly, relative to the plunger rod guiding means 5) at the end of the priming stroke. Furthermore, the dosing sleeve 7 comprises on its interior surface a projection 7*b* which together with an axial notch 6*c* on an interior surface of the end cap 6 as shown in FIGS. 13 and 14 co-operates to function as a means for preventing rotation of the dosing sleeve 7 relative to the casing before (in particular until) a priming operation (i.e., a priming stroke) for priming the reservoir (in particular the syringe 11) is completed. In particular, the axial notch 6*c* is open in at least one axial direction, in particular in the distal axial direction (i.e., at its distal end). At the end of the priming stroke, the projection 7*b* of the rotation prevention means has to travel a distance corresponding to the priming stroke in order to exit the axial groove 6*c* in a distal direction, whereby a rotation of the dosing sleeve 7 relative to the end cap 6 and the plunger rod guiding means 5 is allowed.

FIG. 13 shows the position of the projection 7b in the axial groove 6c before the priming stroke, and FIG. 14 shows the position of the projection 7b at the end of the priming stroke 6c, i.e., after the priming stroke has been completed.

According to FIGS. 12b and 18, the dosing sleeve 7 also comprises a part of a ratchet means. In this embodiment, the ratchet means comprises projections 7g which run substantially parallel to the axial direction and recesses 7h between the projections 7g which also run substantially parallel to the axial direction. Projections 7g and recesses 7h are provided at the proximal end of the dosing sleeve 7 on its interior surface which lies opposite an exterior surface of the plunger rod 10, in particular of the operating knob 10e. At its proximal end section, the plunger rod 10 comprises ratchet springs 10i which are able to elastically move in a radial direction and during the rotation of the dosing sleeve 7 for aligning a dose defining groove 7e, 7e' with the dose blocking means 5e, 5d co-operate with the projections 7g and the recessed 7h to function as a ratchet means. In particular, the ratchet springs 10i move over the projections 7h, whereby the ratchet springs 10i are mechanically excited so as to emit a tactile and acoustic vibration which indicates the dosing operation to the user.

FIG. 15 shows the general structure of the dosing sleeve 7, the end cap 6, the plunger rod 10 and the plunger rod guiding means 5. Details of how the plunger rod 10 is guided in the plunger rod guiding means 5 are also shown in FIG. 17. The plunger rod 10 comprises a rotational blocking means embodied by rotational blocking surfaces 10b which substantially run in an axial direction and are in form-fit with guide rails 5c on the interior surface of the plunger rod guiding means 5. The rotational blocking surfaces 10b and the guide rails 5c support stable axial movement of the plunger rod 10 and prevent the plunger rod 10 from being rotated relative to the casing (in particular relative to the plunger rod guiding means 5) in particular in the configuration in which the front assembly has been coupled to the rear assembly. The rotational blocking surfaces 10b and the guide rails 5c therefore serve as a rotational blocking means which is configured to block a rotation of the plunger rod 10 relative to the casing. The plunger rod guiding means 5 is held in the end cap 6 and is at least partly surrounded by the dosing sleeve 7. The plunger rod 10 is at least partly accommodated by the plunger rod guiding means 5, as shown in FIG. 15.

The above-mentioned rotational blocking means embodied by the rotational blocking surfaces 10b may also serve as an axial stabilizing means. The axial stabilizing means is in particular configured to stabilize the plunger rod while coupling the first casing part to the second casing part and while moving the plunger rod in a distal direction during priming and fluid discharge.

FIGS. 19a to 19c explain the functionality of the needle shield blocking means. FIG. 19a shows the configuration of the needle shield blocking means in an initial state of the injection device which is in particular a delivery state. The syringe holder 9 comprises a second axial locking member embodied by an elastic latch 9c on an exterior surface of the syringe holder 9 (FIG. 1), the elastic latch 9c extending in the proximal direction. The latch 9c is fastened with its base at the distal end of the latch 9c to the interior surface of the syringe holder 9 and comprises at its proximal end a hook having a tapered surface pointing in the proximal direction.

The needle shield 2 comprises a first axial locking member embodied by an elastic latch 2d extending in the distal direction which is configured to lie at the substantially same axial position as the latch 9c and is fastened with its base at the proximal end of the latch 2d to the needle shield 2. At its distal end, the latch 2d comprises a counter-hook which is generally configured to engage with the hook on the latch 9c. The needle shield blocking means is constituted in particular by the hook latches 2d, 9c. FIG. 19a shows an initial state of the needle shield blocking means which is for example a delivery state. In that state, the latch 2d on the needle shield 2 is configured to lie on the latch 9c of the syringe holders 2 so that the hook and the counter-hook are not engaged. When the injection device is pressed onto the injection location, the needle shield 2 is moved in a proximal direction relative to the casing and relative to the syringe holder 9. This leads to the latch 2d being moved away from the latch 9c such that the two latches essentially lie opposite each other in an axial direction. In particular, the two latches do not overlap anymore. This state is shown in FIG. 19b. When the injection has been completed and the injection device is lifted off from the injection location, the needle shield 2 is pushed in the distal direction relative to the casing by the spiral spring 37 such that the latch 2d on the needle shield 2 is pushed under the latch 9c on the syringe holder 9 such that the hook and the counter-hook, respectively, on the two latches 2d, 9c engage with each other. In order to support such a movement of the latches 2d, 9c relative to each other, at least one of the two latches has a tapered surface. In the example shown in FIGS. 19a and 19c, the latch 9c has a tapered surface along which the counter-hook on the latch 2d is able to move in order to engage with the hook on the latch 9c. Due to the engagement of the hook and the counter-hook, the latch 2d is limited in its distal movement by the base of the latch 9c which in the end leads to blocking the axial movement of the needle shield 2 relative to the syringe holder 9 and relative to the casing. In particular, the latch 2d is rested by the latch 9c in those axial directions.

Figure 20B:
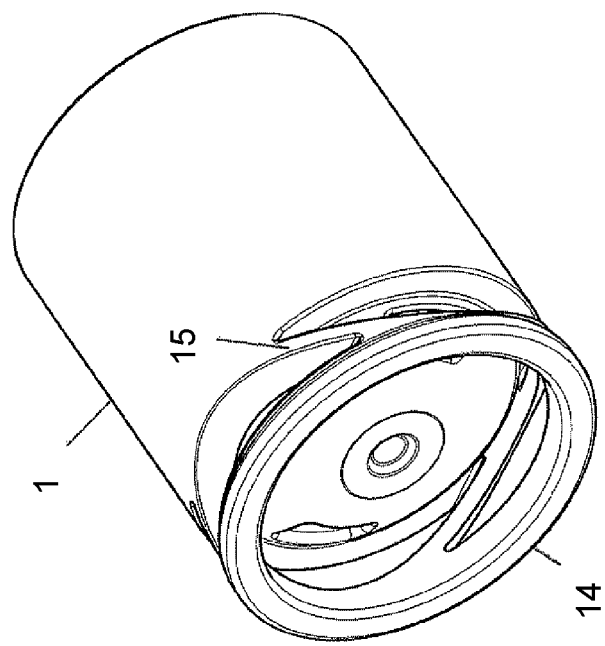
FIGS. 20a and 20b show an embodiment of a needle protection means.
Figure 20A:
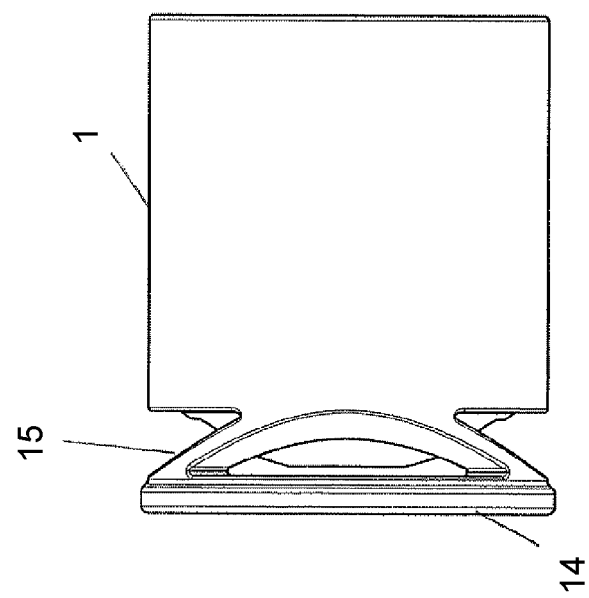

FIGS. 20a and 20b show two perspectives of a front cap 1 having a buffer means 14 at its distal end. The buffer means 14 is embodied by a circular ring which is fastened to the front cap 1 with connector elements (buffer connectors) 15 embodied by buffer connectors which run in an oblique direction relative to the axial and the circumferential direction of the front cap 1 or the injection device, respectively. FIGS. 21a1 to 21e2 show further embodiments of a front cap 1 having a buffer means 14. These embodiments also each comprise a gripping means 16 embodied by two rounded projections located at diametrically opposite positions on the proximal end circumference (i.e., the proximal rim) of the front cap 1. In FIGS. 21a1 and 21a2, the buffer means 14 takes the form of four projections which are bent in a radially outward direction and are provided spaced by 90° at positions on the distal end circumference (i.e., the distal rim) of the front cap 1. In FIGS. 21b1 and 21b2, the buffer means 14 is embodied by an elastic hoop running parallel to a diameter of the distal front surface of the front cap 1 and connected to the distal front surface with a connector element (buffer connector) 15 at each end of the hoop. In FIGS. 21c1 and 21c2, the buffer means 14 is embodied by two rounded axial projections which project out of the distal front surface of the front cap 1, in this case no connector elements are required to connect the buffer means 14 to the remainder of the front cap 1. In FIGS. 21d1 and 21d2, the buffer means 14 is embodied by a circular ring provided on a central connector element 15. The circular ring carries rounded axial projections. In FIGS. 21e1 and 21e2, the buffer means 14 is embodied by a buckled circular ring which is connected to the front cap 1 with buffer connectors 15 located on the axis around which the circular ring is buckled. In a side view of the front cap 1 along this axis, the buffer means 14 (the buckled circular ring) looks like a hyperbola. FIGS. 21/1 and 21/2 contains further views of the buffer means 1 shown in FIGS. 20a and 20b combined in a front cap 1 with a gripping means 16.

In the following, a preferred embodiment of the second aspect of the invention is described with reference to FIGS. 22 to 49. This embodiment is to be understood as a mere example without limiting the second aspect of the invention to the features shown in the Figures. Reference signs used to denote the features shown in and/or described in the context of FIGS. 22 to 49 exclusively apply to the features shown in and/or described in the context of FIGS. 22 to 49. They do not apply to features shown in and/or described in the context of other Figures.

FIGS. 22 to 25 each show a longitudinal section of an injection device of a first example embodiment of the preferred embodiment of the second aspect of the invention. The injection device is an elongated injection pen designed for single use, for a single injection of a liquid drug.

Figure 22:
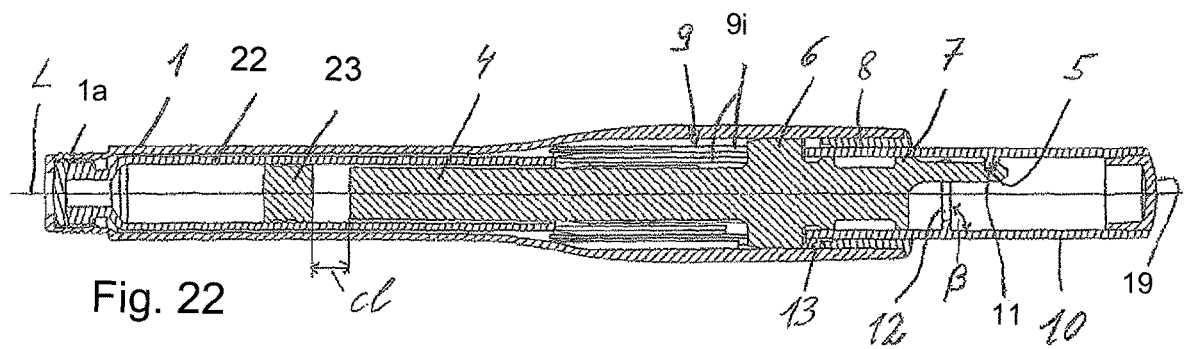
FIG. 22 is an injection device of a first example of the preferred embodiment in an initial state.

FIG. 22 shows the injection device in an initial state before use. The patient is provided with the device in this state. The device comprises a sleeve-shaped casing 1, comprising a distal casing portion in which a reservoir 22 is accommodated which contains the drug, and a proximal casing portion which accommodates a plunger rod 4 and an actuating means 10. The actuating means 10 protrudes out of the casing 1 in the proximal direction at the proximal end.

The reservoir 22 is a carpoule in which the drug is contained in a sterile condition between a septum which sterilely seals a distal outlet of the reservoir 22 and a plunger 23 which sterilely seals the reservoir 22 to the rear. In order to administer the drug, the patient connects a needle unit comprising an injection needle to a distal connecting portion 1a of the casing 1 immediately before administering. As the needle unit is connected, a proximal needle portion of the injection needle pierces the septum. Once the septum has been pierced, the drug is connected to the environment via the injection needle and can be administered by moving the plunger 23 in the forward direction towards the distal end of the reservoir 22. The plunger rod 4 forms a plunger rod. It is only in an axial pressing contact with the plunger 23, i.e., when the device is actuated, the plunger rod 4 presses the plunger 23 in a loose pressing contact in the forward direction, axially towards the outlet of the reservoir 22.

The plunger rod 4 is drivingly coupled with the actuating means 10 by a direct coupling of the plunger rod 4 and the actuating means 10. The plunger rod 4 is guided axially such that it can move in the axial direction, along a device axis L, and prevented from rotation about the axis L. An axial guide is constituted directly by an axial guiding portion 6 of the plunger rod 4 and an axial guiding structure of the casing 1 which blocks the plunger rod 4 against rotation. The plunger rod 4 protrudes into the hollow actuating member 10 and is provided there with a second axial guiding portion 7 which stabilizes the plunger rod 4 by guiding it axially. The guiding engagement with the actuating means 10 allows however for relative rotational movements between the plunger rod 4 and the actuating means 10. The plunger rod 4 can be formed in one piece, e.g., by plastic injection molding. It can alternatively also be formed as an assembled member.

The actuating means 10 can perform a rotational movement, about the device axis L, relative to the casing 1 and also relative to the plunger rod 4. It is furthermore accommodated to perform an axial movement in the forward direction relative to the casing 1. In the initial state, in which the actuating means 10 is in an initial rotational position, the actuating means 10 may however be prevented from being moved in the forward direction, expediently by means of an axial block, such that in the initial state the actuating means 10 can only be rotated. Rotation can furthermore be allowed in a first direction of rotation and prevented in the other. The axial block, if present, is released once the actuating means 10 has been rotated out of its initial rotational position by a predetermined rotation angle. The actuating means 10 is formed as a single actuating member composed of a sleeve-shaped main part and a cap 19 fixedly connected with the main part. The actuating means 10 can at least in principle also be formed in one piece e.g., by plastic injection molding.

The coupling which couples the plunger rod 4 to the actuating means 10 comprises a control member 5, a control track 11 and an entrainment track 12. The control track 11 and the entrainment track 12 are joint track sections of a single continuous combined track 11, 12. Both tracks 11 and 12 are curved about the device axis L. The combined track 11, 12 and the control member 5 together form a cam drive in which the control member 5 is acting as a cam follower.

The control member 5 is formed directly at the plunger rod 4. It is provided on a protrusion which protrudes from a main portion of the plunger rod 4 in the proximal direction. The specific geometry of the control member 5 as such and in relation to the rest of the plunger rod 4 is not important as long as it can perform its function as a cam follower. The continuous combined track 11, 12 is formed directly at the actuating means 10 as a curved shoulder protruding from an inner circumferential surface of the actuating means 10. In a modification, the combined track 11, 12 could be provided in the form of a curved recess and the control member 5 as a radial protrusion which protrudes into the recess. In the example, a proximal portion of the plunger rod 4 protrudes into the sleeve-shaped actuating means 10 to form the coupling inside the actuating means 10. In a further modification, the plunger rod 4 may be provided with a hollow proximal end portion, and the actuating means 10 may protrude in the forward direction into the hollow end portion to form a coupling similar to that of the example embodiment but within the modified plunger rod 4. In yet a further modification the combined track 11, 12 can be formed at the plunger rod 4, and the control member 5, which acts as a cam follower, can be formed at the actuating means 10.

FIGS. 27 and 28 illustrate the injection device of the first example in the inclined sectional view A-A indicated in FIG. 26. In FIG. 27 the initial state is illustrated, i.e., the actuating means 10 is in the initial rotational position as in FIG. 22. FIG. 28 shows the injection device in a state in which the actuating means 10 is in a second rotational position which it takes relative to the casing 1 and the plunger rod 4 after having been rotated about a certain angle from the initial rotational position. The second angular position of the actuating means 10 and, hence, the state of the injection device is the same as in FIG. 23.

The control track 11 and the entrainment track 12 are joined to form the continuous combined track 11, 12, as already mentioned. The control track 11 is inclined with respect to the forward direction at an inclination angle α greater than 0° and smaller than 90°. It has a course which is curved or wound about the device axis L like a turn or partial turn of a screw thread. The inclination α can in particular be selected from the range of 30° and 95°. An inclination of at least 50° and at most 95° is even more advantageous. The inclination α is constant all over the course of the control track 11, but can vary in modifications. The control track 11 has a greater pitch than track 12. The entrainment track 12 of the example is formed as a ring or partial ring having a constant inclination β of 90° with respect to the forward direction, i.e., its pitch is zero. The tracks 11 and 12 are in abutment in a joining region. The inclination of the combined track 11, 12 changes over its course from the inclination α of the control track 11 to the inclination β of the entrainment track 12 monotonously. The inclination changes however abruptly from the inclination α of the control track 11 to the constant inclination β of the entrainment track 12. In a modification, the combined track 11, 12 can have an elongated joining region in which the inclination α is varied smoothly from an inclination smaller than 90° of the control track 11 to an inclination of 90° of the entrainment track 12. In further modifications, the inclination α of the control track 11 can smoothly be increased towards the end of the control track 11, at which the tracks 11 and 12 abut one another, with still an abrupt change of inclination directly at the abutment to the inclination β of the entrainment track 12. The combined track 11, 12 is nevertheless continuous, i.e., uninterrupted. The control member 5 is shaped to compensate for an abrupt transition from the inclination of the control track 11, which is smaller than 90°, to the inclination of the entrainment track 12, and follows the course of the combined track 11, 12 while maintaining the engagement with the combined track 11, 12 continuously.

The injection device provides for dosage selection by the patient. The actuating means 10 also forms a dosing member and together with the casing 1 a dosing means. The dosage is set i.e., selected, by rotating the actuating means 10 into a certain angular position relative to the casing 1. In order to fulfill the dosing function, the actuating means 10 comprises a first dosing element 13, and the casing 1 is provided with a dosing structure 9 of a plurality of second dosing elements $9_i$ When the dosage is being set, the first dosing element 13 co-operates with the plurality of second dosing elements which are arranged in a distribution about the device axis L and formed in a dosing portion of the casing 1 on its inner surface area. The dosing elements $9_i$, where $i$=1, 2, 3, n, are axial guides for the first dosing element 13 which co-operates as an engaging element with said guides $9_i$ The dosing elements $9_i$ exhibit different axial lengths, wherein these lengths each correspond to a dosage which can be set. The dosing elements $9_i$ are for example formed as axial blind grooves on the inner circumference of the casing 1. The blind grooves are open at their proximal ends, such that the first dosing element 13 can move in the forward direction into one of these dosing elements $9_i$ in accordance with the rotational angular position of the actuating means 10 and be moved in the forward direction in the course of a delivery stroke in the dosing element $9_i$ in question, up to the distal end of the respective one of the dosing elements $9_i$. The dosing element 13 forms a delivery abutment by moving into axial abutting contact against a delivery abutment of the casing 1, formed in the example by the distal end of the respective blind groove. The length of the delivery stroke does correspond to the length of the second dosing element $9_i$ which co-operates with the first dosing element 13 in accordance with the dosage set.

The first dosing element 13 can also form, in a dual function, a blocking element of the axial block, already mentioned previously, for blocking the actuating means 10 in the initial state of the injection device, i.e., in the initial rotational position of the actuating means 10. The casing 1 can form a blocking counter element of the axial block, e.g., by means of a circumferential shoulder which extends over a certain angle about the device axis L such that the actuating means 10 is blocked against a forward axial movement until it has been rotated into the second rotational position. In yet a further function the dosing element 13 can serve as a retaining element by which the actuating means 10 is retained in the casing 1 by blocking it against a movement in the proximal direction. The casing insert 8 can for example form the retaining counter element for retaining the actuating means 10 in the casing 1.

The actuating means 10 can furthermore form a dosing latching means with the casing 1 or the casing insert 8. A dosing latching structure can extend around the device axis L and can be formed on the actuating means 10. When the actuating means 10 is rotationally moved, an elastically flexible dosing latching element in the form of a radially flexible snapper which is formed on the casing 1, 8 slides over the dosing latching structure. The dosing latching structure can be formed e.g., in the manner of an outer toothing of the actuating means 10 and can correspond in its circumferential tooth separation to the separation of the second dosing elements $9_i$ such that the dosing latching element respectively engages with a recess of the dosing latching structure when the first dosing element 13 is exactly axially flush with one of the second dosing elements $9_i$. In a reversal of the arrangement, the dosing latching structure could also be formed on the inner surface area of the casing 1, 8 and an elastically flexible dosing latching element could be formed on the actuating means 10.

The patient is provided with a device in the initial state illustrated in the FIGS. 22 and 27. The control member 5 engages the control track 11 and is near an end of the track 11 which is distant from the entrainment track 12. The plunger rod 4 may already contact the plunger 3 in the forward direction, or an axial clearance cl may exist between the plunger 3 and the plunger rod 4. The clearance cl, if present at all, depends on tolerances at which the components of the injection device can be manufactured cost-efficiently. The clearance cl is also affected by the accuracy of the axial position of the plunger 23 in the reservoir 22.

For administration, the patient connects the injection needle to the reservoir 22 by plugging or screwing the needle holder onto the connecting portion 1a of the casing 1.

The clearance cl, if present, is eliminated and the reservoir 22 vented, i.e., de-aerated, by gripping the injection device in the initial state and turning the actuating means 10 in the first rotational direction. The rotational movement of the actuating means 10 causes the control track 11 to move relative to the control member 5. The inclination of the control track 11 is such that the control track 11 exerts an axial forward force onto the control member 5. The plunger rod 4 is accordingly moved axially forward, towards and against the plunger 23, if a clearance cl is present. Once in pressing contact the plunger 23 is also moved forward. The injection device is expediently held during this clearance elimination and de-aeration stroke with the needle pointing upwards to expel air which may be present in the reservoir 22.

The injection device forces such an initial priming step to at least eliminate any axial clearance cl and, preferably, to de-aerate the reservoir 22 at least partially. A dosage cannot be set and delivered until after this initial priming step. Prematurely setting and delivering the dosage is prevented by a blocking engagement between a blocking element of the actuating means 10 and an axial abutment of the casing 1. The blocking element of the actuating means 10 can, for example, be constituted by the dosing element 13, as described already previously. The axial abutment of the casing 1 extends in the circumferential direction over an angle which corresponds to the angle of rotation the actuating means 10 has covered during its initial rotational movement so far. Once the actuating means 10 has accomplished the initial rotational priming movement the blocking engagement is released and the actuating means 10 can now be moved in the forward direction. The actuating means 10 can also be rotated further to select a dosage which is smaller than the dosage which corresponds to the rotational position the actuating means 10 has directly at the end of the initial priming step.

At the end of the initial priming step the control member 5 still engages the control track 11. The inclination of the control track 11 is such that the actuating means 10 would carry the plunger rod 4 in the forward direction if the actuating means 10 would now be pressed forward. The amount of liquid drug present in the reservoir 22 at the end of the initial priming step is accordingly the maximum dosage which can be administered. Turning the actuating means 10 further in the first direction will cause the plunger rod 4 to move forward until the control member 5 is clear of the control track 11 and engages the entrainment track 12. Patients who do not need the maximum dosage will hold the injection device with the needle upward to expel the residual air which might still be present after the initial priming step.

Figure 23:
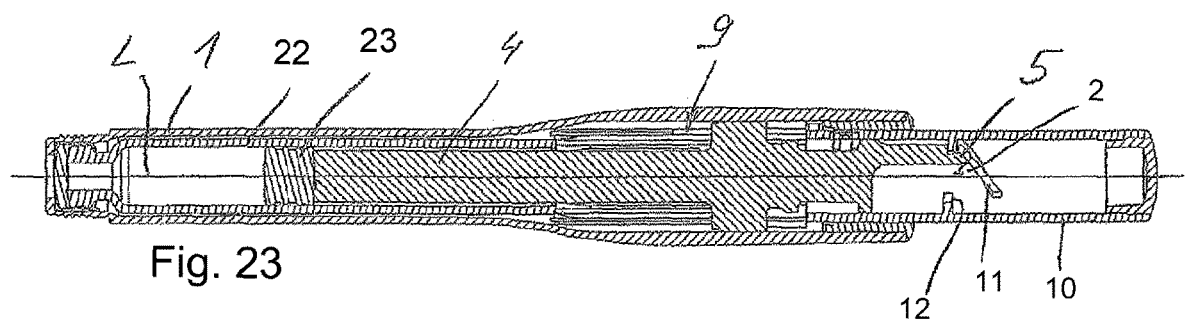
FIG. 23 is the injection device of the first example after initial priming.

FIG. 23 shows the injection device in a state after initial priming by which any clearance cl, if present, has been eliminated. If there did not exist a substantial clearance cl in the initial state entrapped air would also have been removed from the reservoir 22, i.e., the priming of the injection device would have been accomplished. The plunger 23 is in an axial position corresponding to a now predetermined initial internal volume of the reservoir 22, let's say 0.5 ml. This initial volume corresponds to the maximum dosage which can be selected and administered.

Figure 24:
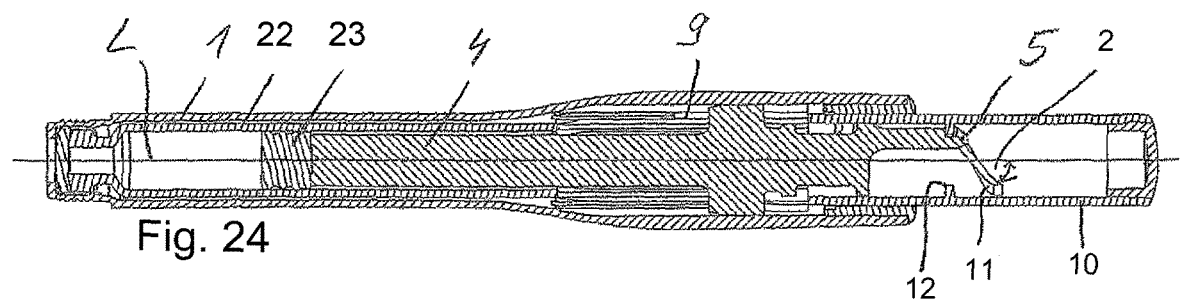
FIG. 24 is the injection device of the first example after completion of priming.
Figure 25:
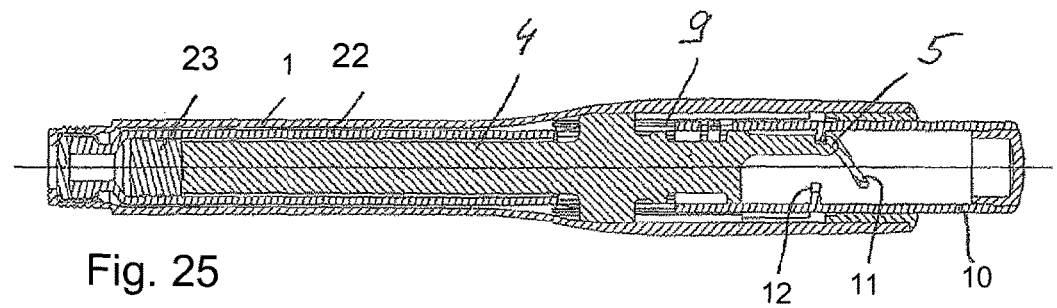
FIG. 25 is the injection device of the first example after injection.

FIG. 24 shows the injection device after completion of any priming operation. The control member 5 now engages the entrainment track 12 which has an axial level course. Turning the actuating means 10 further in the first rotational direction will therefore not cause any further axial movement of the plunger rod 4. In this state the patient can select any dosage predetermined by the arrangement of the second dosing elements $9_i$ as described previously. The entrainment track 12 can extend almost over 360° about the device axis L thereby allowing almost a complete turn of the actuating means 10 to select the desired dosage. The dosage is displayed in a dosage display window 51 which is provided as a recess at the proximal end of the casing 1, 8. Dosage numbers which correspond to the selectable dosages are provided on the actuating means 10.

Once the dosage has been selected the patient presses the actuating means 10 into the forward direction. While moving forward the actuating means 10 carries the plunger rod 4 via engagement of the control member 5 and the entrainment track 12 also in the forward direction. The plunger 23 is accordingly moved forward towards the outlet of the reservoir 22 whereby the selected dosage of the drug is expelled and administered.

Figure 29:
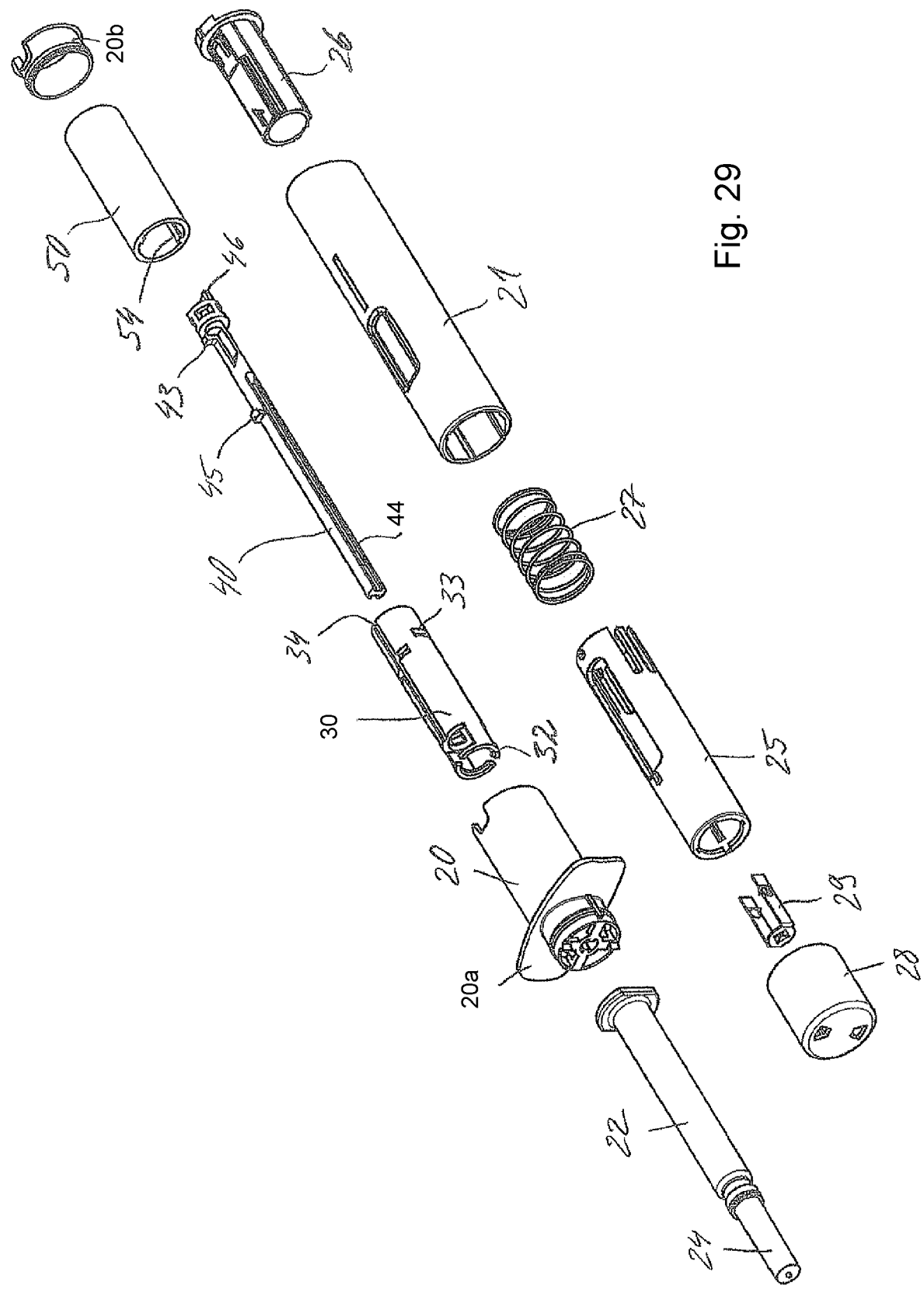
FIG. 29 is an exploded view of an injection device of a second example embodiment.

FIG. 29 is a perspective, exploded view of an injection device of a second example of the preferred embodiment. The injection device comprises a proximal housing portion 20 with a pair of wings 20a and a distal housing portion 21 which can be fixed, one to the other, to form a casing together with a casing insert 20b which, in the assembled state, is positioned at the proximal end of the proximal casing portion 20, axially and rotationally fixed to the casing portion 20.

A reservoir 22 which is prefilled with a liquid drug is accommodated in the distal housing portion 21. The reservoir 22 of the second example of the preferred embodiment is a syringe having an injection needle already mounted such that it protrudes from the distal end of the reservoir 22 in the forward direction. The needle is not visible, it is covered by a needle cap 24. A needle cover sleeve 25 is accommodated in the distal housing portion 21 such that it can move axially backward, in the proximal direction, against the restoring force of a cover sleeve spring 27. The needle cover sleeve 25 surrounds the syringe 22 and in particular the injection needle in the assembled state of the injection device. A cap remover 28 with a remover insert 29 is mounted at the distal end of the distal housing portion 21. A reservoir holder 26 which is arranged in the distal housing portion 21 serves to accommodate the reservoir 22. In the assembled state, which is shown e.g., in FIGS. 31 and 32, the reservoir 22 is axially held in position between the reservoir holder 26 and a distal surface of the proximal casing portion 20.

The proximal casing portion 20 serves as a mechanism holder. It accommodates a plunger rod 40 which can be moved axially, along the device axis L, but is prevented from rotation about the axis L. The plunger rod 40 is provided with one or more axial guiding elements 44 e.g., one or more axial grooves, which interact with an axial guide of the casing portion 20 to guide the plunger rod 40 axially and block it against rotation. The plunger rod 40 comprises a first dosing element 43 which is provided at the plunger rod 40 such that it can be moved radially against a resilient restoring force. The first dosing element 43 can in particular be formed, as in the example of the preferred embodiment, as a radial protrusion at an axially extending arm which can be bent resiliently. A further protrusion of the plunger rod 40 serves as a control member 45 of the second example of the preferred embodiment. An entrainment member 46 is in addition to the control member 45 formed at the plunger rod 40. In the example of the preferred embodiment the entrainment member 46 is formed as an axial protrusion protruding in the proximal direction from a proximal end of the plunger rod 40.

The proximal casing portion 20 furthermore accommodates an actuating means composed of a dosing member 30 and an actuating member 50. Both members 30 and 50 can in particular be sleeve-shaped as in the example of the preferred embodiment.

FIG. 30 shows the injection device of the second example of the preferred embodiment in an axial view in which the sectional planes of the longitudinal sections illustrated in the FIGS. 31 and 32 are indicated.

As can be seen in the FIGS. 31 and 32, the dosing member 30 is axially secured to the casing portion 20 by the engagement of connecting elements 32 of the dosing member 30 with an internal retaining structure 20c of the proximal casing portion 20. When the device components are assembled the connecting elements 32 snap-fit behind the retaining structure 20c to secure the dosing member 30 to the casing portion 20. This securement prevents axial movements of the dosing member 30 which can however freely rotate relative to the casing 20, 20b, 21.

The actuating means 50 can perform a rotational movement relative to the casing 20, 20b, 21 and also relative to the plunger rod 40. It can furthermore perform an axial movement in the forward direction relative to the casing 20, 20b, 21. It is connected to the dosing member 30 secured against rotation but axially movable by means of the engagement of one or more axial guiding elements 34 of the dosing member 30 and one or more axial guiding elements 54 of the actuating member 50 (see e.g., FIG. 29). The one or more guiding elements 34 and 54 are provided as one or more axially extending grooves and co-operating ribs. In the assembled state, the dosing member 30 protrudes into the sleeve-shaped actuating member 50 such that the guiding elements 34 and 54 engage thereby preventing relative rotational movements between the dosing member 30 and the actuating member 50 but allowing for relative axial movements of the actuating member 50.

The plunger rod 40 is drivingly coupled with the actuating means 30, 50 by a direct coupling. The coupling comprises the control member 45 and the additional entrainment member 46 at the side of the plunger rod 40 and a control track 31 which is provided at the dosing member 30 and an entrainment track 52 which is provided at the actuating member 50. Both tracks 31 and 52 are curved about the device axis L and inclined with respect to the forward direction. The control track 31 is formed at an inner circumferential surface of the dosing member 30 as a curved shoulder. The entrainment track 52 is a forward facing surface of a sleeve-shaped structure which protrudes from a distal bottom of the actuating member 50 in the forward direction towards the entrainment member 46.

The control member 45 of the plunger rod 40 engages the control track 31. The engagement of the control track 31 and the control member 45 can be seen e.g., in FIG. 32. The control track 31 and the control member 45 constitute a cam drive, similar to the first embodiment, in which the control member 45 is acting as a cam follower. A forward facing surface of the control track 31 pushes axially in the forward direction against the control member 35 to move the plunger rod 40 in the forward direction when the dosing member 30 is turned about the device axis L.

The entrainment member 46 and the entrainment track 52 each have a course which is adapted to the course of the control track 31 such that the entrainment member 46 stays in axial contact with the entrainment track 52 when the actuating member 50 performs a rotational movement and the plunger rod 40 an axial movement relative to the actuating member 50. In the example of the preferred embodiment the control track 31 and the entrainment track 52 have corresponding inclinations with respect to the forward direction. The inclination is greater than 0° and smaller than 90° and can in particular be at least 30° and at most 95° and even more advantageous be at least 50° and at most 95°.

The entrainment member 46 can best be seen in FIG. 37. It extends over approximately 180° about the device axis L and ascends axially over its course to form a curved ramp. The entrainment track 52 extends over 360° about the device axis L. It is composed of a curved ramp section, which corresponds in shape and extension to the entrainment member 46, and a shell section of a constant axial length. In a modification, the geometry can be reversed, i.e., the entrainment member 46 be composed of a curved ramp and a shell section of constant length and the entrainment track 52 be formed as the curved ramp. In another modification, an entrainment track can be formed like track 52 at one of the members 40 and 50 and an entrainment member as a simple cam at the other one of the members 40 and 50.

The injection device of the second example of the preferred embodiment provides for dosage selection by the patient. The dosing means of the second example of the preferred embodiment is formed by the dosing member 30 and the plunger rod 40. The dosage can be set, i.e., selected, by rotating the actuating member 50 and therewith the dosing member 30 into a certain angular position relative to the plunger rod 40 which is prevented from rotation relative to the casing 20, 21, 20b, as already mentioned. In order to fulfill the dosing function, the dosing member 30 comprises a plurality of second dosing elements 33 which are arranged in a distribution about the device axis L and formed at the circumference of the dosing member 30. The dosing elements 33 are recesses which are formed as passages through the circumference of the dosing member 30. The dosing elements 33 must however not necessarily be formed as passages, they can instead be formed e.g., as pockets in the inner circumferential surface of the dosing member 30. The second dosing elements 33 can best be seen in the perspective view of FIG. 37. The second dosing elements 33 are located at different axial heights, wherein the axial positions of the dosing elements 33 correspond each to a dosage which can be set. When the plunger rod 40 is moved forward during a delivery stroke the first dosing element 43 engages that one of the second dosing elements 33 which has been brought axially flush with the first dosing element 43 during the dosage setting operation. The engagement of the first dosing element 43 with the selected one of the second dosing elements 33 terminates the delivery stroke of the plunger rod 40.

The actuating member 50 is blocked in the initial state against forward movement. The axial blocking engagement can be released by turning the actuating means 50 from its initial rotational position into a first direction over a certain angle to a second rotational position which is predetermined by the blocking engagement. The blocking engagement can e.g., be established as illustrated in FIG. 38. In the example of the preferred embodiment the blocking engagement is established by means of a blocking element 53 formed at the outer circumference of the actuating member 50 and a corresponding blocking shoulder or recess which is formed at an inner circumferential surface of the proximal casing portion 20. The recess could alternatively be formed in an inner circumferential surface of the casing insert 20b. The blocking member 53 can furthermore serve the purpose to retain the actuating member 50 within the casing 20, 21, 20b.

FIGS. 31 and 32 show the injection device in an initial state before use. The patient is provided with the device in this state. The actuating member 50 is in the initial rotational position in which the control track 31 contacts the control member 45 and the entrainment track 52 contacts the entrainment member 46 each in the forward direction. In the initial rotational position the ramp section of the entrainment track 52 is in circumferential overlap with the entrainment member 46. The needle cover 25 is in a forward position in which it surrounds the needle N which is still covered by the needle cap 24. The cap remover 28 is mounted and the remover insert 29 grips behind or clamps the needle cap 24.

To inject the drug, the patient pulls off the cap remover 28 and therewith the needle cap 24.

In the next step, the device is primed to eliminate any axial clearance cl, if present at all, within the drive chain which reaches from the actuating member 50 up to the plunger 23 and also to de-aerate the reservoir 22. For priming the patient holds the injection device with the needle N pointing upward and turns the actuating member 50 and therewith the dosing member 30 about the device axis L in the first rotational direction. The rotational movement of the actuating means 30, 50 causes the control track 31 to turn relative to the control member 45. The inclination of the control track 31 is such that the control track 31 exerts an axial forward force onto the control member 45 such that the plunger rod 40 is pushed axially forward, towards and against the plunger 23, if a clearance cl is present. Once in pressing contact the plunger 23 is also moved forward.

The injection device of the second example of the preferred embodiment forces such an initial priming step to at least eliminate any axial clearance cl and, preferably, to de-aerate the reservoir 22 at least partially. A dosage cannot be set and delivered until after this initial priming step. Prematurely setting and delivering the dosage is prevented by the blocking engagement between a blocking element, e.g., the blocking element 53 (FIG. 38) of the actuating member 50 and an axial abutment of the casing 20, 20b, 21. The axial blocking element and the abutment of the casing extends in the circumferential direction over an angle which corresponds to the angle of rotation the actuating member 50 has covered during its initial rotational movement so far. Once the actuating member 50 and the dosing member 30 have accomplished the initial rotational priming movement the blocking engagement is released and the actuating member 50 can now be moved in the forward direction. The rotational unit of actuating member 50 and dosing member 30 can also be rotated further to select a dosage which is smaller than the dosage which corresponds to the rotational position the actuating member 50 and dosing member 30 have arrived at directly at the end of the initial priming step.

FIG. 33 shows the injection device of the second example of the preferred embodiment directly after completion of the initial priming step.

At the end of the initial priming step the control member 45 still engages the control track 31. Furthermore, the entrainment track 52 is in axial contact with the entrainment member 46. If one would depress the actuating member 50 the plunger rod 40 would be pushed in the forward direction by the axial force exerted to the plunger rod 40 via the contact of the entrainment track 52 and the entrainment member 46, and also via the contact of the control track 31 and the control member 45. The amount of liquid drug present in the reservoir 22 at the end of the initial priming step is the maximum dosage which can be administered.

FIG. 33 shows the injection device in a state in which any clearance cl, if present previously, has been eliminated. If there did not exist a substantial clearance cl in the initial state, entrapped air will also have been removed from the reservoir 22, i.e., de-aeration of the injection device would have been accomplished, at least partially. The plunger 23 is in an axial position corresponding to a now predetermined initial internal volume of the reservoir 22, let's say 0.5 ml. This volume corresponds to the maximum dosage. The dosage is displayed, as in the first example of the preferred embodiment, in a dosage display window of the casing 20, 20b, 21 (FIG. 29).

Turning the actuating member 50 and therewith the dosing member 30 further into the first rotational direction will also cause the plunger rod 40 to move forward until the control member 45 comes clear of the control track 31. Patients who do not need the maximum dosage will hold the injection device with the needle N upward to expel residual air which might still be present after the initial priming step.

FIG. 34 shows the injection device after completion of any priming operation. The control member 45 has reached the end of the control track 31 or, to be more precise, the end of the control track 31 has reached the control member 45. The engagement of the control member 45 and the control track 31 has been released thereby. A further rotational movement of the dosing member 30 will not cause any further axial movement of the plunger rod 40. In this state the patient can select any dosage predetermined by the arrangement of the second dosing elements 33, as described previously. During such further rotational movement the entrainment member 46 is still in axial contact with the entrainment track 52.

FIG. 35 shows the injection device in a state in which the actuating means 30, 50 has been turned about an angle greater than the maximum rotational angle provided for priming such that a small dosage has been set, as can be seen from the small axial distance between the first dosing element 43 and the second dosing element 33 which has been brought in axial alignment with the first dosing element 43 by the rotational movement of the actuating means 30, 50.

To inject the selected dosage the injection device is positioned at the injection site. The patient holds the injection device and presses the same axially against the skin. Under the axial pressing force exerted the needle cover sleeve 25 moves backwards against the force of the cover sleeve spring 27 and the injection needle N penetrates the skin until a depth is reached which is predetermined by the axial position into which the needle cover sleeve 25 can move relative to the distal casing portion 21.

Once the injection needle N is placed e.g., subcutaneously the selected dosage can be administered by depressing the actuating member 50. The axial pressing force is transmitted via the engagement of the entrainment track 52 and the entrainment member 46 onto the plunger rod 40 which is accordingly carried along by the actuating member 50 in the forward direction. The plunger rod 40 pushes the plunger 23 in the forward direction such that the selected dosage is delivered at the injection site.

FIG. 36 shows the injection device after completion of the delivery stroke. As can be seen in comparison with FIG. 35, a larger dosage has been selected. During the delivery stroke the dosing element 43 has been moved into the sleeve-shaped dosing member 30 and forced to resiliently yield such that it snaps back outwardly in the radial direction and into the recess provided by the selected second dosing element 33 of the dosing member 30. The provision of the second dosing elements 33 as recesses in the circumference of the dosing member 30, in the example of the preferred embodiment as passages, has as an advantage that the engagement does not only terminate the delivery stroke but prevents the plunger rod 40 from being retracted. The plunger rod 40 is blocked against a backward movement by the engagement of the first dosing element 43 and the selected one of the second dosing elements 33.

Once dosage delivery has been completed, the injection device is retracted from the injection site. The cover sleeve spring 27 forces the needle cover sleeve 25 forward to cover again the injection needle N. The forward movement of the needle cover sleeve 25 causes a needle cover block to be activated such that the needle cover sleeve 25 will become blocked in its forward position.

FIGS. 39 to 42 illustrate a dosing latching means of the second example of the preferred embodiment. The dosing latching means is formed by a dosing latching structure of the proximal casing portion 20 and a resilient dosing latching element 35 of the dosing member 30. The dosing latching structure comprises a plurality of latching counter elements 20d each formed as a recess at an inner circumference of the casing portion 20 and spaced apart from one another in the circumferential direction. FIG. 40 shows the casing portion 20 in the view E indicated in FIG. 39. The cross-sections E-E of the FIGS. 41 and 42 show the dosing latching means in two different states. In FIG. 41 the dosing member 30 is in the second rotational position which corresponds with the position it takes when only the initial priming step has been performed. It engages the latching counter element 20d of the dosing latching structure which is located in the 2 o'clock position in FIG. 41. The next latching counter element 20d in counter-clockwise direction is the recess for latching the dosing member 30 in the initial rotational position. By turning the dosing member 30 in the clockwise direction, during initial priming, the dosing member 30 has been moved into the second rotational position it takes in FIG. 41. The second rotational position may correspond e.g., to a dosage of 0.5 ml, as mentioned previously. Turning the dosing member 30 further in the clockwise direction the dosing latching element 35 engages in either one of the next three latching counter elements 20d which correspond to let's say, 0.4, 0.3 and 0.2 ml, which are the dosages which can be selected. In FIG. 42, in which the dosing latching element 35 is engaged in the 6 o'clock position a dosage of 0.3 ml, would accordingly have been selected, if we stay in the dosage example.

Figure 44:
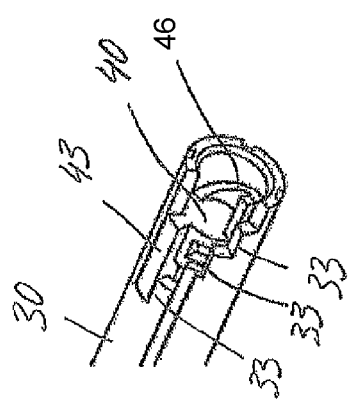
FIG. 44 is a dosing member and a plunger rod of the third example.
Figure 43:
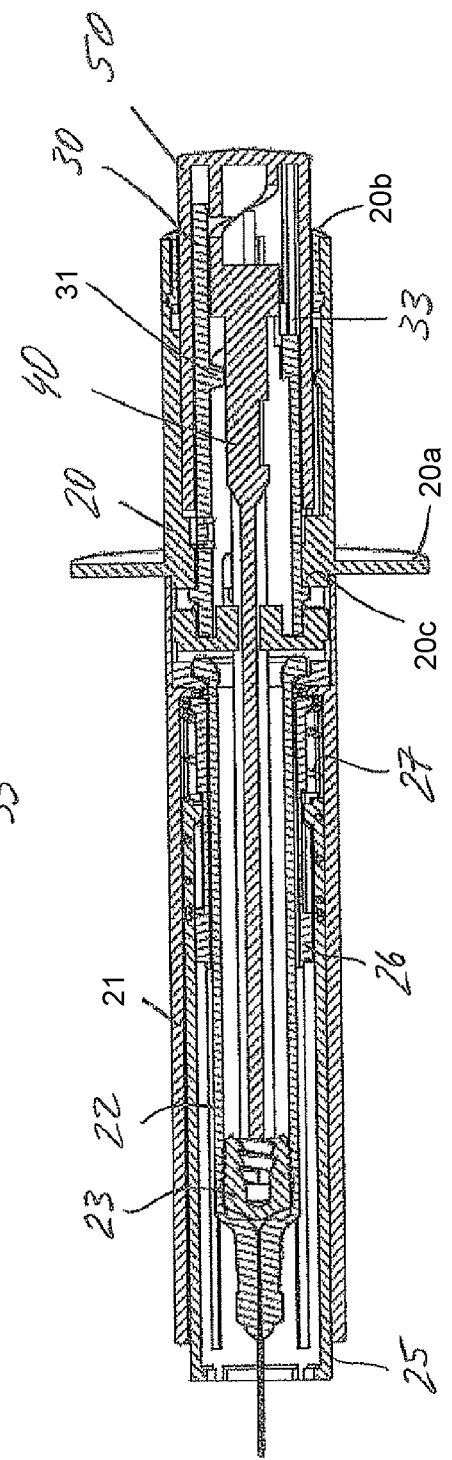
FIG. 43 is an injection device of a third example of the preferred embodiment.

The FIGS. 43 and 44 illustrate an injection device of a third example of the preferred embodiment which comes close to the second example of the preferred embodiment. It differs from the second example of the preferred embodiment only with respect to the dosing means which is formed by a dosing member 30 and a plunger rod 40 which are modified with respect to the second example of the preferred embodiment only in that the dosing structure of the dosing member 30 is no longer formed by passages or pockets in the circumference of the dosing member 30. The dosing elements 33 of the modified dosing member 30 are provided by means of a staircase-like recess in the circumference of the dosing member 30, each dosing element 33 being formed as a step of this recess. The first dosing element 43 is no longer a resilient snapper, it is formed as a rigid outward protrusion of the modified plunger rod 40. The interaction of the first dosing element 43 and the dosing structure composed of the second dosing element 33 can easily be grasped from the perspective view of FIG. 44.

The modified dosing means 33, 43 does not provide for a retraction block. Retraction of the plunger rod 40 when having performed the delivery stroke is prevented otherwise, if desired, e.g., by a blocking engagement of the actuating member 50 with e.g., the proximal casing portion 20 or the casing insert 20b.

FIGS. 45 and 46 show an injection device of a fourth example of the preferred embodiment, in an initial state before use, in two different longitudinal sections. The injection device comprises a proximal housing portion 20 and a distal housing portion 21 which are fixedly connected one to the other. The distal housing portion 21 accommodates a reservoir 22 with a plunger 23 and a forwardly protruding injection needle N, furthermore a reservoir holder 26, a needle cover sleeve 25 and a cover sleeve spring 27. The needle N is covered with a needle cap 24 which can be removed by means of a cap remover 28 which comprises a remover insert 29. The components mentioned so far and their interactions can be regarded to be identical to those of the second and third examples of the preferred embodiments.

The proximal casing portion 20 serves as a mechanism holder. It accommodates a plunger rod 4 such that the plunger rod 4 can be moved axially, along the device axis L, but is prevented from rotation by blocking the plunger rod 4 in a guiding portion 6 of the same. The casing portion 20 is furthermore provided with a dosing structure 9 which comprises a plurality of dosing elements $9_i$ which are distributed over an inner circumference of the casing portion 20. With respect to the axial guidance of the plunger rod 4 and further details of the dosing structure 9, reference is made to the first example of the preferred embodiment.

The proximal casing portion 20 furthermore guides an actuating means 10 axially. The actuating means 10 can furthermore perform rotational movements relative to the casing portion 20 and also relative to the plunger rod 4. The actuating means 10 is a single actuating member comprising a sleeve-shaped main part and a cap 19 which is fixedly secured to the main part.

The plunger rod 4 is drivingly coupled to the actuating means 10 by direct engagement of the two members 4 and 10. The coupling is formed by the engagement of an entrainment member 5 and an entrainment track 12. The entrainment member 5 is formed at the plunger rod 4, and the entrainment track 12 is formed at the actuating means 10. The entrainment track 12 is ring-shaped and can in particular be extended over the full 360° about the device axis L. It has over its course a constant inclination of 90° with respect to the forward direction. The entrainment track 12 is in axial forward contact with the entrainment member 5, such that the actuating member 10, when moved in the forward direction, carries the plunger rod 4 along to perform a delivery stroke. In a modification, the arrangement could be reversed, i.e., an entrainment track like track 12 could be formed at the plunger rod 4 and an entrainment member at the actuating means 10.

The actuating means 10 can be identical to the actuating means 10 of the first example of the preferred embodiment except for the control track of the first example of the preferred embodiment which is not present in the fourth example of the preferred embodiment. There is no cam drive which would transmit a rotational movement of the actuating means 10 into an axial translational movement of the plunger rod 4 in the forward direction. The actuating means 10 is rotationally decoupled from the plunger rod 4. The plunger rod 4 and the actuating means 10 constitute however a unit with respect to axial translational movements, namely via the coupling provided by the engagement of the entrainment member 5 and the entrainment track 12. The entrainment member 5 engages the entrainment track 12 with respect to both axial directions in that it is provided with a recess into which the entrainment track 12 protrudes, as in the first example of the preferred embodiment. In a modification, the entrainment member 5 can abut the entrainment track 12 with a free end, as a simple cam. The same holds for the first example of the preferred embodiment.

The actuating means 10 is provided with a first dosing element 13, as in the first example of the preferred embodiment. The first dosing element 13 interacts for dosage selection with the second dosing elements as already described for the first example of the preferred embodiment.

The fourth example embodiment differs from the first example of the preferred embodiment furthermore in that the actuating means 10 is blocked against rotation in the initial state of the injection device. The rotational block is provided by the engagement of the first dosing element 13 and the device casing, in the fourth example of the preferred embodiment with a blocking counter element formed at the casing insert 16.

FIG. 47 shows the arrangement of plunger rod 4, actuating means 10 and casing insert 16 in a perspective view and in a state which corresponds to the initial state of the assembled injection device. The blocking counter element 17 of the casing insert 16 is formed as a recess which is open towards a distal rim of the casing insert 16 such that the dosing element 13 can be moved out of the blocking engagement with the blocking counter element 17 by a relatively short forward priming stroke of the actuating means 10.

The actuating means 10 can be blocked releasably from moving in the forward direction. Such a releasable axial block can be established e.g., by friction or, more expediently, by a form fit which can be overcome against a resilient blocking force. The releasable axial block can in particular be formed by means of the casing 16, 20, 21 and the dosing element 13. The casing can, for example, be provided with an inward protrusion just in front of the dosing element 13. The dosing element 13 can be moved axially over such a protrusion if the casing portion 20, or alternatively the casing insert 16, would resiliently yield such that the dosing element 13 can pass the protrusion.

In FIG. 48 the dosing means of the fourth example of the preferred embodiment is schematically illustrated. The illustration can be regarded as a development or projection of the inner circumference of the casing insert 16 and the proximal casing portion 20 in the axial region where the blocking counter element 17 and the dosing structure 9 are formed.

FIG. 49 illustrates schematically a development of a casing 16, 20 which is modified with respect to the blocking counter element 17 which differs from the element 17 of FIG. 48 in that the counter blocking element 17 of the casing, here of the casing insert 16, is no longer formed as only an axially straight recess, but is L-shaped with an axial and a circumferential section thereby preventing that the actuating means 10 can be moved forward in the initial state of the injection device. Rather, the actuating means 10 must first be rotated slightly and can only thereafter be pushed forward up to an axial abutment 18 which is formed, as in FIG. 48, at the proximal casing portion 20. When the blocking and dosing element 13 has left the blocking counter element 17 and reached the abutment 18, the actuating means 10 can be rotated relative to the casing portion 20 to select the dosage. The actuating means 10 can furthermore be blocked releasably in its initial rotational position, i.e., in the rotational position it takes in FIG. 49. The releasable rotational block can for example be formed by an inward protrusion formed at the casing portion 20 or the casing insert 16 and an radially outward protrusion of the actuating means e.g., by the dosing element 13. A protrusion of the casing 16, 20 would be formed such that it can resiliently yield and the counter protrusion e.g., the dosing element 13 pass the protrusion of the casing in the circumferential direction in order that the actuating means 10 can be rotated out of its initial rotational position. Provision of such an additional releasable rotational block would more securely prevent that the user might impair the dosing element 13 in the attempt to rotate the actuating means 10 beyond the non-releasable rotational block established by the interaction of the dosing element 13 and the blocking counter element 17.

For injecting the drug the user takes the injection device of the fourth example of the preferred embodiment and removes the needle cap 24, as explained previously in connection with the second example of the preferred embodiment. In the next step, the actuating means 10 is pushed forward (FIG. 48) or turned and then forward (FIG. 49), against the abutment 18, thereby eliminating any axial clearance cl (FIG. 45), if present, and de-aerating the reservoir 22. Once this priming operation has been completed, with the needle N pointing upwards, the dosage can be selected. The dosage selection operation is the same as described already under the first example of the preferred embodiment. Once the dosage has been selected the patient places the device at the injection site with the needle N pointing to the skin, exerts axial pressure such that the casing and the needle advance while the cover sleeve 25 is moved backwards. When the tip of the needle N has been placed in or under the skin the patient exerts axial pressure onto the actuating means 10, thereby pushing the same in the forward direction together with the plunger rod 4 to perform the delivery stroke and administer the selected dosage.

The short priming stroke and also the delivery stroke are effected by means of the drive coupling formed by the engagement of the entrainment member 5 and the entrainment track 12.

While the present disclosure has been described with reference to various embodiments, it will be understood that these embodiments are illustrative and that the scope of the disclosure is not limited to them, and variations, modifications, additions, and improvements are possible. More generally, embodiments in accordance with the present disclosure have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. An injection device, comprising:
   a casing which accommodates or forms a reservoir for a liquid drug;
   a plunger rod which can move relative to the casing in a distal direction to deliver the drug;
   a needle shield which is movable in an axial direction relative to the casing such that the needle shield moves in a proximal direction from an initial state to an injection position, and in the distal direction from the injection position to a blocking position;
   a spiral spring configured to bias the needle shield in the distal direction; and
   a needle shield locking means configured to lock the needle shield such that the needle shield cannot move axially relative to the casing in the blocking position after the injection device performs an injection,
   wherein the needle shield locking means comprises a first axial locking member disposed axially along the needle shield and a second axial locking member disposed axially along the casing,
   wherein in the initial state of the needle shield, the first axial locking member is deflected axially away from a longitudinal axis of the device in a first direction by a first side of the second axial locking member,
   wherein upon movement of the needle shield to the injection position, the first axial locking member and the second axial locking member lie opposite each other in the axial direction such that the first axial locking member is no longer axially deflected by the second axial locking member and the first axial locking member is not engaged with the second axial locking member, and
   wherein during movement of the needle shield to the blocking position, the first axial locking member is deflected axially away from the longitudinal axis by a second side of the second axial locking member, and upon reaching the blocking position, the first axial locking member engages with the second axial locking member on the second side to thereby prevent the needle shield from moving axially.

2. The injection device of claim 1, wherein the first axial locking member moves along a surface of the second axial locking member during movement from the injection position to the blocking position such that the first axial locking member is deflected axially away from the longitudinal axis by the second side of the second axial locking member.

3. The injection device of claim 1, wherein the casing comprises a syringe holder and the second axial locking member is disposed on the syringe holder.

4. The injection device of claim 1, wherein at least one of the first axial locking member and the second axial locking member comprises an elastic hook and the other of the first axial locking member and the second axial locking member comprises an elastic counter-hook.

5. The injection device of claim 4, wherein the hook is configured to engage with the counter-hook during a proximal movement of the needle shield.

6. The injection device of claim 5, wherein once the injection device is removed from an injection location after performing the injection, the spiral spring moves the needle shield in the distal direction towards the initial state that the hook and the counter-hook abut each other.

7. The injection device of claim 6, wherein the counter-hook abuts a base of the hook such that an axial movement of the needle shield is prohibited in the blocking position.

8. The injection device of claim 4, wherein the hook is disposed on a latch of the needle shield or the casing and the counter hook is disposed on a latch of the other of the needle shield or the casing.

9. The injection device of claim 8, wherein in the initial state of the needle shield locking means prior to use of the injection device, the latch on the needle shield is configured to overlap and lie on the latch of the casing such that the hook and the counter-hook are not engaged.

10. The injection device of claim 9, wherein when the injection device is pressed onto an injection location in the injection position, the needle shield is moved in the proximal direction relative to the casing such that the latch of the needle shield is moved away from the latch of the casing and the latches lie opposite each other in the axial direction and no longer overlap.

11. The injection device of claim 10, wherein when the injection has been completed and the injection device is lifted off from the injection location, the needle shield is pushed in the distal direction relative to the casing by the spiral spring such that the latch of the needle shield is pushed under the latch of the casing and causes the hook and the counter-hook to engage with each other in the blocking position.

12. The injection device of claim 8, wherein least one of the latches has a tapered surface extending in the axial direction.

13. The injection device of claim 12, wherein the counter-hook is configured to move along the tapered surface until the counter-hook engages with the hook to thereby lock the needle shield.

14. The injection device according to claim 1, further comprising a dosing sleeve which can move in the proximal direction relative to the casing to prime the reservoir and which can rotate relative to the casing for selecting a dose to be injected, wherein rotation of the dosing sleeve relative to the casing is prevented until a priming operation for priming the reservoir is completed.

15. The injection device according to claim 14, wherein the dosing sleeve comprises a projection on an internal surface configured to engage a notch disposed on the casing to enable rotation of the dosing sleeve at the end of a priming stroke of the priming operation for selecting the dose.

16. The injection device according to claim 15, wherein the dosing sleeve further comprises a protrusion on an interior surface at a distal end of the dosing sleeve, the protrusion configured to deflect a flexible tongue disposed on the casing at the end of the priming stroke to prevent a rotation of the dosing sleeve back into a position which the dosing sleeve had at the end of the priming stroke relative to the casing.

17. The injection device according to claim 14, wherein the dosing sleeve comprises at least one dose defining groove configured to define the dose to be injected.

18. The injection device according to claim 17, the dosing sleeve further comprising at least one circumferential projection configured to lock the dosing sleeve after discharging the liquid drug from the reservoir.

19. The injection device according to claim 14, wherein the dosing sleeve further comprises a ratchet means which is configured to be activated by rotating the dosing sleeve relative to the casing, the ratchet means comprising recesses and protrusions configured to co-operate with recesses and protrusions associated with the plunger rod.

20. The injection device according to claim 1, wherein the casing comprises a first casing part and a second casing part which can be coupled to the first casing part such that the first casing part and the second casing part cannot move relative to each other in the axial direction and cannot rotate relative to each other.

21. The injection device according to claim 1, further comprising a plunger rod guiding sleeve for guiding the plunger rod therein, and an outer casing part, wherein the plunger rod guiding sleeve comprises a holding arms for holding the plunger rod guiding sleeve in the outer casing part.

22. The injection device according to claim 21, wherein the plunger rod guiding sleeve further comprises one or more radially extending elastic members for tensioning the plunger rod guiding sleeve relative to the outer casing part.

23. The injection device according to claim 21, wherein the plunger rod guiding sleeve further comprises an axial blocking means which is configured to block movement of the plunger rod relative to the casing in an axially backward direction, wherein the axial blocking means comprise elastic abutment members with abutment surfaces on their distal side which run in a substantially radial direction.

24. The injection device according to claim 21, wherein the plunger rod guiding sleeve further comprises a guide rail for engaging with the plunger rod and blocking a rotation of the plunger rod relative to the casing.

25. The injection device according to claim 1, further comprising a needle protection cap provided with at least one of the following:
   a) axially extending hooks for removing a needle cover for covering a needle of the injection device; or
   b) a buffer for buffering a mechanical action on the needle protection cap, the buffer comprising one or more of: a ring coupled to a distal end of the needle protection cap, projections bent in a radially outward direction, an elastic hoop running parallel to a diameter of a distal front surface of the needle protection cap, or axial projections projecting from the distal front surface of the needle protection cap.

26. A method of assembling an injection device, comprising:

providing an injection device comprising a first casing part and a second casing part which can be coupled to the first casing part;

providing a reservoir for receiving a liquid drug;

inserting the reservoir into one of the first casing part and the second casing part; and after inserting the reservoir, coupling the first casing part and the second casing part to each other such that the first casing part and the second casing part cannot move relative to each other in an axial direction of the injection device and cannot rotate relative to each another such that the reservoir cannot move relative to the one of the first casing part and the second casing part into which the reservoir was inserted, wherein one of the first or the second casing part comprises:
- a needle shield which is movable in an axial direction relative to the casing parts such that the needle shield moves in a proximal direction from an initial state to an injection position, and in a distal direction from the injection position to a blocking position;
- a spiral spring configured to bias the needle shield in the distal direction; and
- a needle shield locking means configured to lock the needle shield such that the needle shield cannot move axially relative to the casing in the blocking position after the injection device performs an injection,
- wherein the needle shield locking means comprises a first axial locking member disposed axially along the needle shield and a second axial locking member disposed axially along the casing,
- wherein in the initial state of the needle shield, the first axial locking member is deflected axially away from a longitudinal axis of the device in a first direction by a first side of the second axial locking member,
- wherein upon movement of the needle shield to the injection position, the first axial locking member and the second axial locking member lie opposite each other in the axial direction such that the first axial locking member is no longer axially deflected by the second axial locking member and the first axial locking member is not engaged with the second axial locking member, and
- wherein during movement of the needle shield to the blocking position, the first axial locking member is deflected axially away from the longitudinal axis by a second side of the second axial locking member, and upon reaching the blocking position, the first axial locking member engages with the second axial locking member on the second side to thereby prevent the needle shield from moving axially.

27. An injection device, comprising:

a casing which accommodates or forms a reservoir for a liquid drug;

a plunger rod which can move relative to the casing in a distal direction to deliver the drug;

a needle shield which is movable in an axial direction relative to the casing such that the needle shield moves in a proximal direction from an initial state to an injection position, and in the distal direction from the injection position to a blocking position;

a spiral spring configured to bias the needle shield in the distal direction; and a needle shield locking means configured to lock the needle shield such that the needle shield cannot move axially relative to the casing in the blocking position after the injection device performs an injection, wherein the needle shield locking means comprises a first axial locking member disposed axially along the needle shield and a second axial locking member disposed axially along the casing, wherein in the initial state of the needle shield, the first axial locking member is deflected axially away from the longitudinal axis of the device in a first direction by a first side of the second axial locking member, wherein upon movement of the needle shield to the injection position, the first axial locking member and the second axial locking member lie opposite each other in the axial direction such that the first axial locking member is no longer axially deflected by the second axial locking member and the first axial locking member is not engaged with the second axial locking member, and wherein during movement of the needle shield to the blocking position, the first axial locking member moves along a surface of the second axial locking member and is deflected axially away from the longitudinal axis, and upon reaching the blocking position, the first axial locking member engages with a second side of the second axial locking member to thereby prevent the needle shield from moving axially.

* * * * *